US009610225B2

(12) United States Patent
Maeda et al.

(10) Patent No.: US 9,610,225 B2
(45) Date of Patent: Apr. 4, 2017

(54) MEDICAL TABLET, AND MANUFACTURING METHOD AND MANUFACTURING APPARATUS FOR MEDICAL TABLET

(71) Applicants: OTSUKA PHARMACEUTICAL CO., LTD., Tokyo (JP); OMORI MACHINERY CO., LTD., Koshigaya-shi, Saitama (JP)

(72) Inventors: Etsuhiro Maeda, Koshigaya (JP); Yasutoshi Kohata, Koshigaya (JP)

(73) Assignees: Otsuka Pharmaceutical Co., Ltd., Chiyoda-Ku, Tokyo (JP); Omori Machinery Co., Ltd., Koshigaya-shi, Saitama (JP)

( * ) Notice: Subject to any disclaimer, the term of this patent is extended or adjusted under 35 U.S.C. 154(b) by 0 days.

(21) Appl. No.: 14/652,380

(22) PCT Filed: Dec. 19, 2013

(86) PCT No.: PCT/JP2013/084015
§ 371 (c)(1),
(2) Date: Jun. 15, 2015

(87) PCT Pub. No.: WO2014/098166
PCT Pub. Date: Jun. 26, 2014

(65) Prior Publication Data
US 2015/0328150 A1 Nov. 19, 2015

(30) Foreign Application Priority Data

Dec. 19, 2012 (JP) ................ 2012-277458
Dec. 19, 2012 (JP) ................ 2012-277459
Dec. 19, 2012 (JP) ................ 2012-277460
Aug. 28, 2013 (JP) ................ 2013-177383

(51) Int. Cl.
A61K 9/20 (2006.01)
A61J 3/10 (2006.01)
B30B 11/00 (2006.01)
G08B 1/08 (2006.01)
A61K 9/00 (2006.01)
B30B 11/08 (2006.01)
B30B 11/34 (2006.01)

(52) U.S. Cl.
CPC .............. A61J 3/10 (2013.01); A61K 9/0097 (2013.01); A61K 9/2095 (2013.01); B30B 11/007 (2013.01); B30B 11/08 (2013.01); B30B 11/34 (2013.01); A61J 2205/60 (2013.01); A61K 9/2072 (2013.01)

(58) Field of Classification Search
None
See application file for complete search history.

(56) References Cited

U.S. PATENT DOCUMENTS

| 4,440,355 A | 4/1984 | Mori et al. |
| 6,068,465 A | 5/2000 | Wilson |
| 6,425,422 B1 | 7/2002 | Trebbi |
| 2006/0145876 A1* | 7/2006 | Kimura ................ A61B 5/073 340/573.1 |
| 2008/0020037 A1 | 1/2008 | Robertson et al. |
| 2008/0284599 A1 | 11/2008 | Zdeblick et al. |
| 2009/0009332 A1 | 1/2009 | Nunez et al. |
| 2009/0082645 A1 | 3/2009 | Hafezi et al. |
| 2010/0069717 A1 | 3/2010 | Hafezi et al. |
| 2010/0185055 A1 | 7/2010 | Robertson et al. |
| 2010/0298668 A1 | 11/2010 | Hafezi et al. |
| 2011/0306852 A1 | 12/2011 | Hafezi et al. |
| 2012/0007734 A1 | 1/2012 | Berkman et al. |
| 2012/0011699 A1 | 1/2012 | Hafezi et al. |
| 2012/0018844 A1 | 1/2012 | Hafezi |
| 2012/0059257 A1 | 3/2012 | Duck et al. |
| 2012/0116188 A1 | 5/2012 | Frank et al. |
| 2012/0116359 A1 | 5/2012 | Hafezi et al. |
| 2012/0319328 A1 | 12/2012 | Ando et al. |
| 2015/0164746 A1* | 6/2015 | Costello ................ A61B 5/07 264/112 |

FOREIGN PATENT DOCUMENTS

| JP | S57140000 | 8/1982 |
| JP | S6212521 | 1/1987 |
| JP | H02160450 | 6/1990 |
| JP | H04272026 | 9/1992 |
| JP | H06115687 A | 4/1994 |
| JP | 2002-326177 | 11/2002 |
| JP | 4549504 B2 | 9/2010 |
| JP | 4591758 B2 | 12/2010 |
| JP | 4666951 B2 | 4/2011 |
| JP | 2012514798 A | 6/2012 |
| WO | WO2010/080765 | 7/2010 |
| WO | WO2011/068963 | 6/2011 |
| WO | WO2011/108648 | 9/2011 |
| WO | WO2011/127252 | 10/2011 |
| WO | WO2012/071280 | 5/2012 |
| WO | WO 2012/149466 | 11/2012 |
| WO | WO 2014/018454 | 1/2014 |
| WO | WO 2014/144738 | 9/2014 |
| WO | WO 2015/112604 | 7/2015 |
| WO | WO 2015/119911 | 8/2015 |

OTHER PUBLICATIONS

International Search Report for International Application No. PCT/JP2013/084015, mailed Mar. 18, 2014.

(Continued)

Primary Examiner — H. Sarah Park

(57) ABSTRACT

An object is to provide a tablet manufacturing apparatus capable of supplying an IC chip to a desired position of pharmaceutical powder with a high accuracy and suppressing a positional displacement. The IC chip is supported by a positioning guide with a chip main body in a downward manner, and is held in a state of being positioned above pharmaceutical powder filled in a die hole before compression. The IC chip is supplied by a pusher.

20 Claims, 48 Drawing Sheets

(56) References Cited

OTHER PUBLICATIONS

Japanese Office Action mailed Aug. 16, 2016 for Japanese Application No. 2012-277459.

* cited by examiner

FIG.7A    FIG.7B
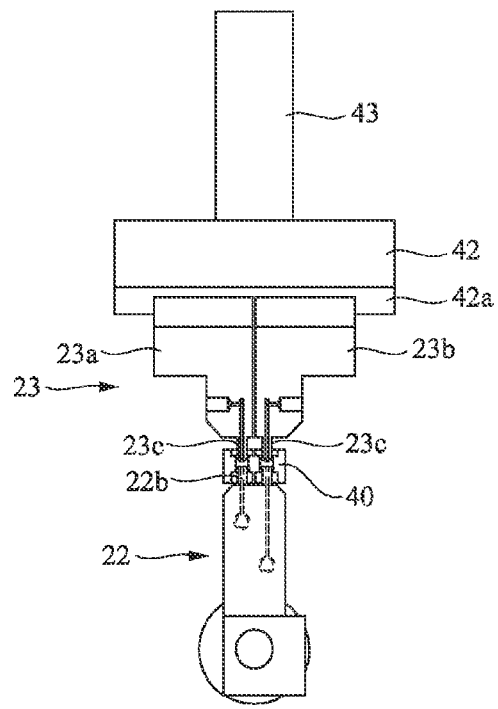
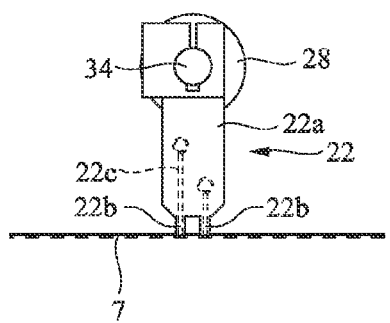

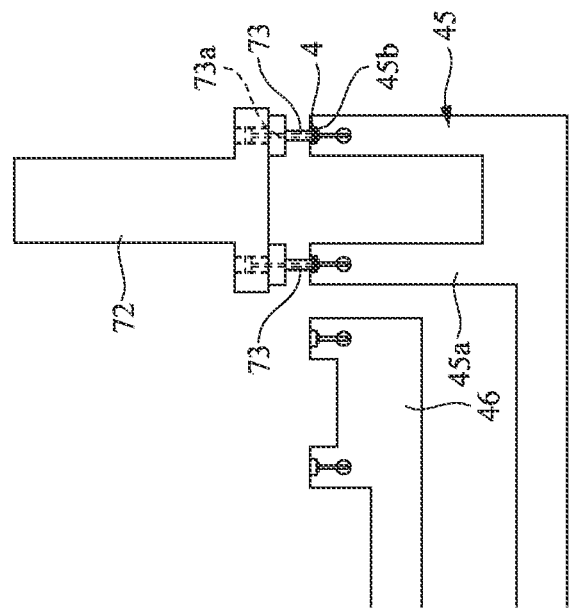
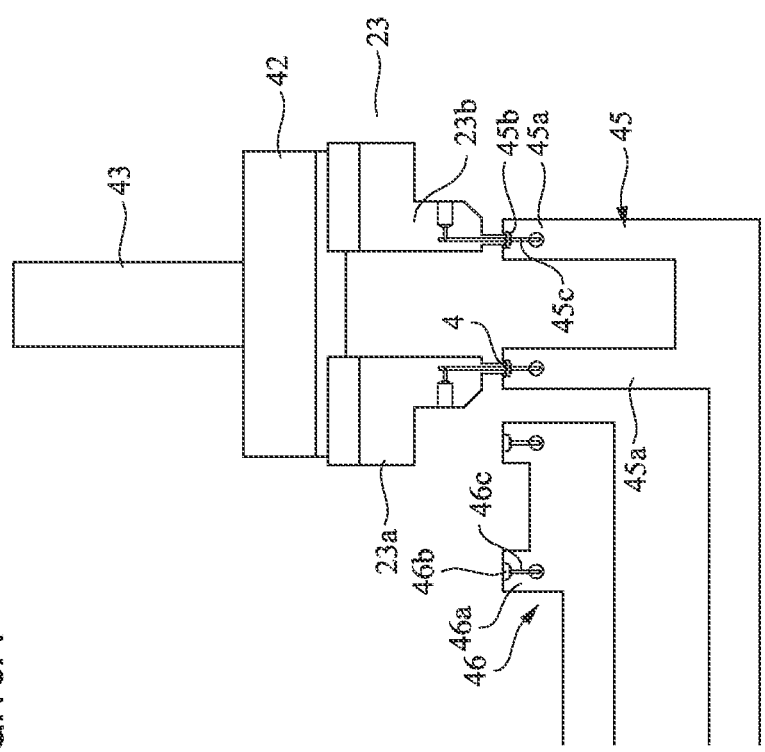
FIG.10A
FIG.10B

FIG.27A    FIG.27B
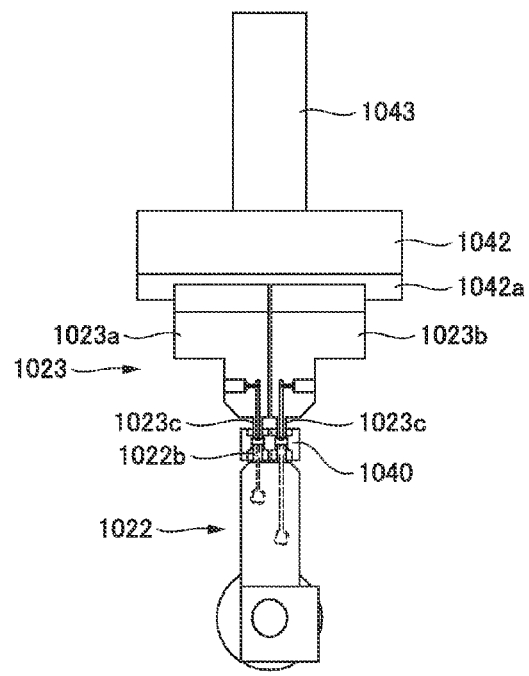
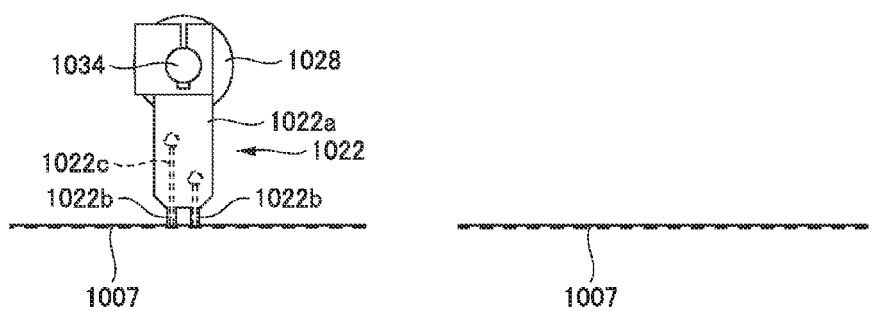

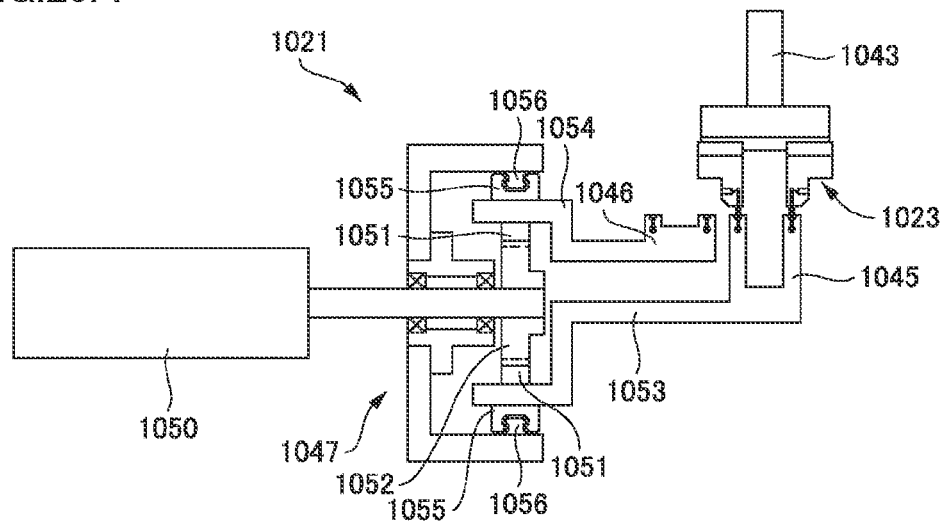
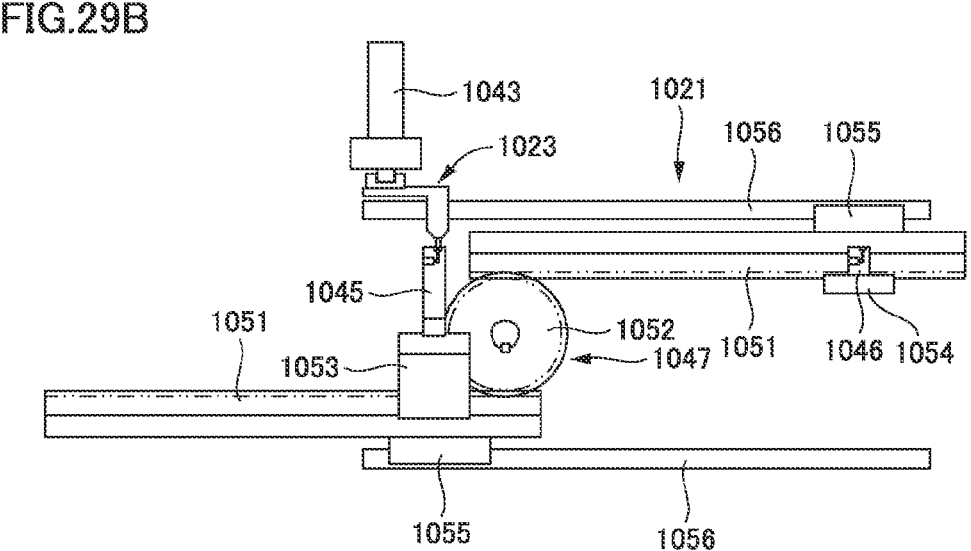

FIG.47A
FIG.47B
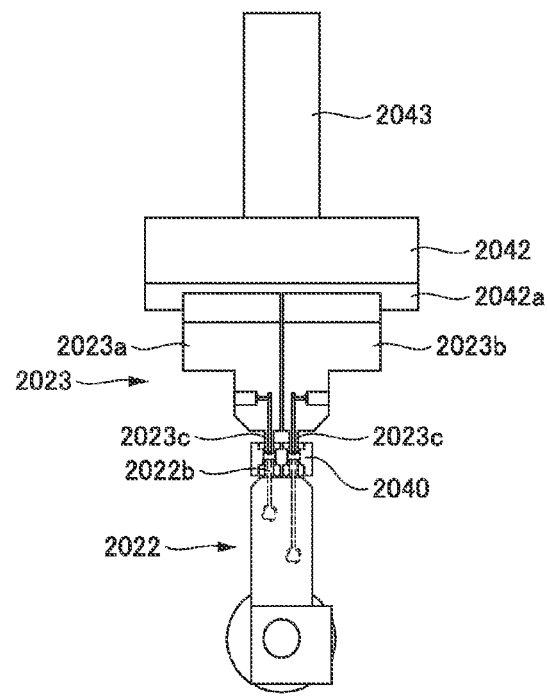
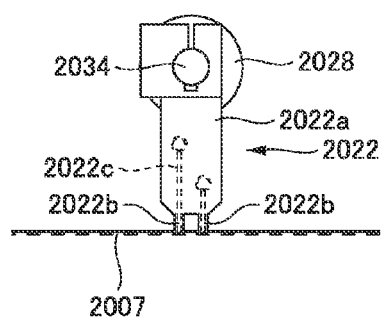

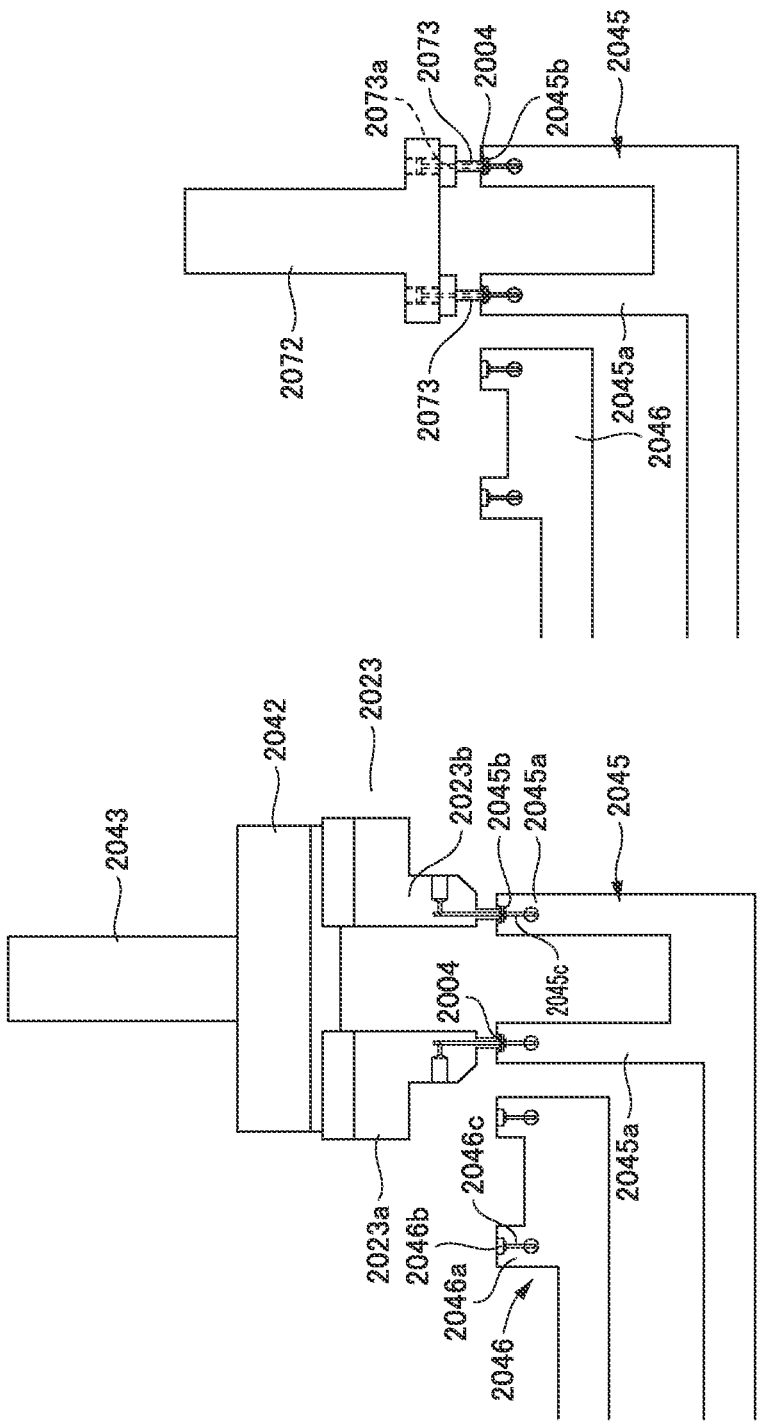

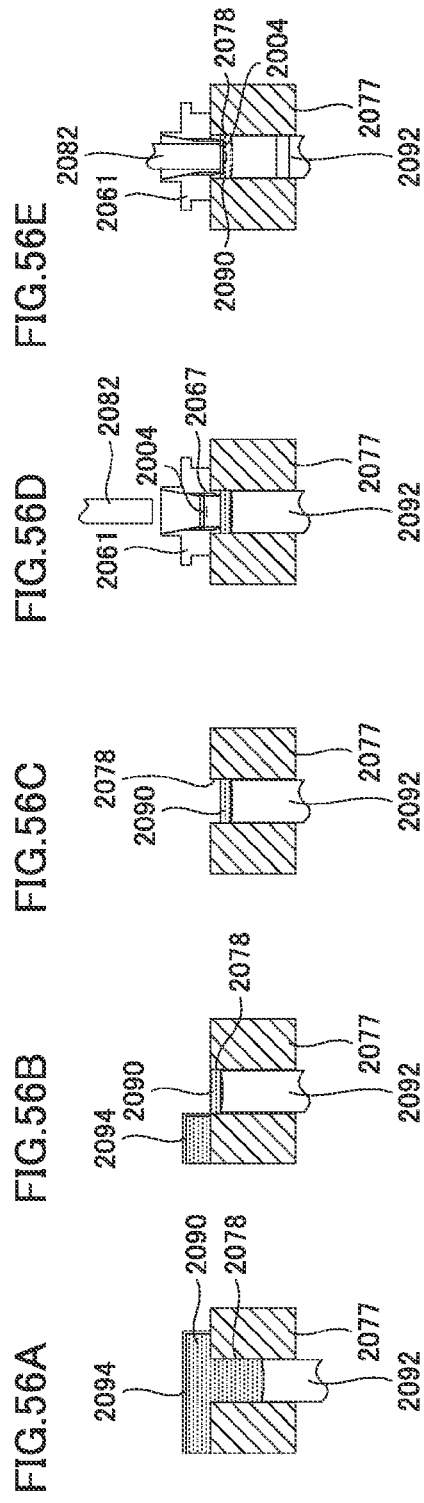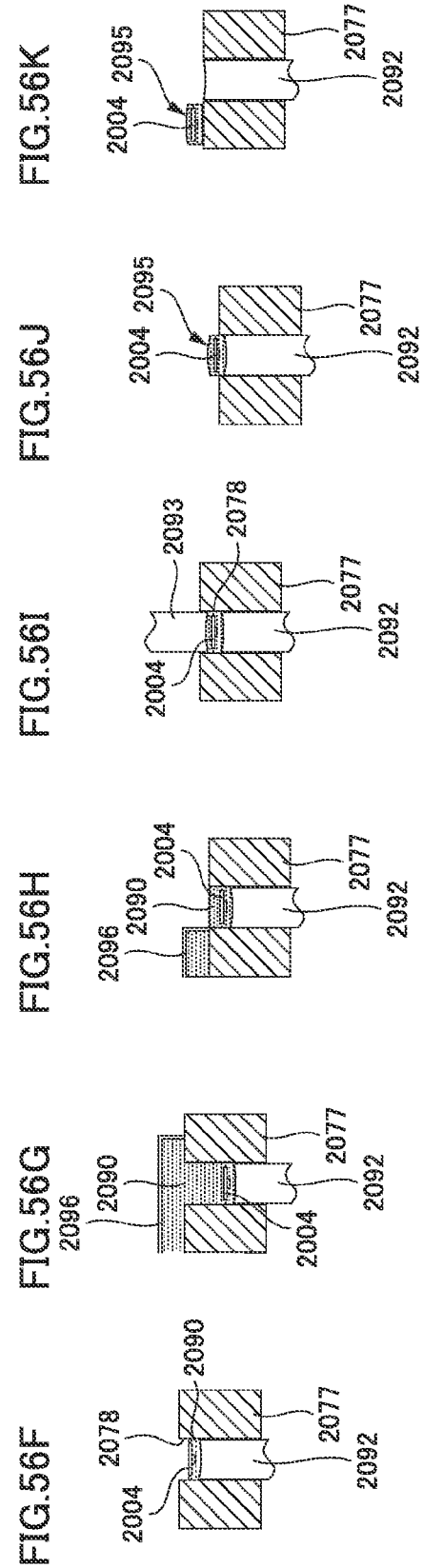

MEDICAL TABLET, AND MANUFACTURING METHOD AND MANUFACTURING APPARATUS FOR MEDICAL TABLET

CROSS-REFERENCE TO RELATED APPLICATIONS

This application is a US National Stage Entry of PCT Application No. PCT/JP2013/084015, filed Dec. 19, 2013, which claims priority to Japanese Patent Application No. 2013-177383, filed Aug. 8, 2013, Japanese Patent Application No. 2012-277460, filed Dec. 19, 2012, Japanese Patent Application No. 2012-277459, filed Dec. 19, 2012 and Japanese Patent Application No. 2012-277458.

TECHNICAL FIELD

The present invention relates to a medical tablet, and a manufacturing method and a manufacturing apparatus for a medical tablet. More specifically, it relates to a medical tablet containing an IC chip, and a manufacturing method and manufacturing apparatus for the medical tablet.

BACKGROUND ART

There is a core-containing tablet as a kind of a tablet for use in a medicine and the like. This core-containing tablet includes a nucleated tablet and a covering portion in a periphery thereof. Generally, a nucleated tablet and a covering portion are composed of different kinds of medicines or pharmaceutical compositions each other, and a nucleated tablet is buried in a tablet center. When a nucleated tablet is not located at a center of a tablet, not only a loss or crack may occur in a covering portion, but also expression of an expected efficacy is disturbed, or an unexpected side reaction may occur. As described above, the positioning of the nucleated tablet may greatly affect a quality of a core-containing tablet. As a tablet manufacturing apparatus which manufactures this kind of core-containing tablet, there is for example a rotational core-containing tablet manufacturing machine as disclosed in PTD 1.

This rotational core-containing tablet manufacturing machine has a basic configuration to fill pharmaceutical powder into a plurality of die holes provided at predetermined intervals on a circumference along an outer edge portion of a rotating disk rotating at a high speed, supply a nucleated tablet onto pharmaceutical powder, further fill pharmaceutical powder onto the nucleated tablet, and thereafter compress and shape these pharmaceutical powders and nucleated tablet by means of a lower pestle and an upper pestle.

In the apparatus disclosed in PTD 1, a supplying apparatus which supplies a nucleated tablet is devised for the purpose of positioning a nucleated tablet at a tablet center. A plurality of plate springs (23) are radially or diagonally radially mounted on a transfer disk (14), and a nucleated tablet insertion pin (27) is attached to the free end thereof and located above a nucleated tablet holding portion (15) of transfer disk (14). A push-down roller (39) is provided which comes into contact with a head (29) of nucleated tablet insertion pin (27) and pushes down the same when nucleated tablet holding portion (15) of transfer disk (14) and die hole (4) of a rotating disk (5) overlap each other. The nucleated tablet is forced by nucleated tablet insertion pin (27) at a predetermined timing and then dropped and supplied. As illustrated above, an operation timing of nucleated tablet insertion pin (27) is set to be a timing of overlapping nucleated tablet holding portion (15) and die hole (4), so that the dropped nucleated tablet is dropped onto a center of pharmaceutical powder already filling die hole (4). It should be noted that the numbers in parenthesis are reference characters disclosed in the publication of the patent document.

CITATION LIST

Patent Documents

PTD 1: Japanese Patent No. 4549504
PTD 2: Japanese Patent Laying-Open No. 6-115687
PTD 3: Japanese Patent No. 4591758

SUMMARY OF INVENTION

Technical Problem

Now, an IC chip-containing tablet having an IC chip buried in a tablet is considered. The IC chip-containing tablet has a medicine at an outer peripheral wall of the IC chip. Assuming that this IC chip is a nucleated tablet, it is supposed that an IC chip is supplied so as to be positioned at a center of a tablet with use of the above-described conventional apparatus. In that case, it was indeed difficult to supply an IC chip with a high accuracy to a center within appropriately filled powder due to the following reasons.

In other words, for example, as disclosed in paragraph [0023] of PTD 1 " . . . nucleated tablet C is dropped onto pharmaceutical powder first layer P1 filled in said die hole 4" or paragraph [0024] "a failure is less likely to occur in a dropping mechanism itself, so that accuracy and reproducibility of the dropping position of nucleated tablet C are improved," a nucleated tablet is dropped and supplied to pharmaceutical powder. Therefore, when a nucleated tablet is replaced with an IC chip, there is a likelihood that the IC chip is not dropped smoothly and is dropped at a position displaced from a center.

Moreover, for example, when a form of an IC chip to be buried is not configured as a single body of a rectangular chip main body but is configured such that the chip main body is mounted to a film having a predetermined shape, a resistance applied to a film at the time of dropping may become greater, and the chip may not fall while maintaining a horizontal state, so that it may be set on a surface of pharmaceutical powder in a slanted state. Moreover, in the case of the IC chip of a type having a film in such a manner, even when the IC chip is appropriately dropped to a center of a surface of pharmaceutical powder, the chip may slip on the surface of pharmaceutical powder during the subsequent movement and therefore is likely to cause a positional displacement.

On the other hand, the present inventor was conceived of supplying an IC chip in a downward manner to pharmaceutical powder. However, since this kind of IC chip is provided such that it is set in an accommodation portion provided in a carrier tape, in an upward manner with a chip main body facing upward, and is accommodated in an accommodation tape in which an opening side of the accommodation portion is covered with a top tape, the IC chip is in an upward manner when the top tape is peeled off to open. Therefore, since the IC chip cannot be directly supplied to pharmaceutical powder in a downward manner, it is necessary to reverse upside down on the course.

For example, PTDs 2 and 3 disclose the invention of a reversing apparatus for an electronic component. The apparatus disclosed in PTD 2 has rotatable suction means arranged to face each other and passes items in a state where suction portions thereof face each other. However, the apparatus disclosed in PTD 2 needs a separate transfer mechanism for reversing the item. Therefore, the configuration is complicated.

PTD 3 reverses an item by rotation of a head provided with upper and lower cover members which are slidable in a forward and backward direction. However, since the cover member needs to open/close and slide, it is not suitable for a high-speed processing. Further, in the case of a fine electronic component of, for example, several millimeters, holding by suction means cannot be performed firmly. Therefore, since the passing cannot be performed smoothly, an item is likely to be dropped.

Moreover, in the case of a type provided with the above-described film, outside dimensions become greater, so that a difference with respect to dimensions of a tablet becomes smaller. Therefore, even a slight displacement of a supply position to pharmaceutical powder may cause an IC chip to be forced out of a tablet. Higher accuracy in the supply position is required as a problem.

Moreover, the rotational core-containing tablet manufacturing machine disclosed in PTD 1 employs a configuration in which a tabletting machine measuring pharmaceutical powder, placing a desired quantity of the pharmaceutical powder in a die, pressing the pharmaceutical powder placed in the die from above and below to form a predetermined shape of the tablet is integrated with a nucleated tablet supply apparatus supplying a nucleated tablet with respect to pharmaceutical powder, and, above a rotating plate equipped with the die, the nucleated tablet supply apparatus rotating together with rotation of the rotating plate is arranged. On the other hand, when a nucleated tablet supply apparatus is provided separately from a tabletting machine, a region in which an IC chip can be supplied into the die of the tabletting machine having pharmaceutical powder placed therein may be limited. Consequently, it is necessary to supply an IC chip appropriately with use of a narrow space, and there is a likelihood that a space for mounting a inspection apparatus which performs inspection on whether or not an IC chip is located at a center of pharmaceutical powder cannot be reserved. In such a case, there is a problem that it would be necessary to supply the IC chip at a center position with higher accuracy.

Solution to Problem

A manufacturing apparatus for medical tablets manufactures an IC chip member-containing tablet manufactures by supplying an IC chip member equipped with an IC on pharmaceutical powder willed in a die hole, thereafter filling pharmaceutical powder onto the IC chip member, and compressing these pharmaceutical powder and the IC chip member from above and below. The IC chip member has a base plane, and a convex portion protruding more on one side than the other side with respect to the base plane, and the manufacturing apparatus for medical tablets comprises a supply portion which holds the IC chip member convex portion in a downward manner with the convex portion facing downward, and supplies the IC chip member on the pharmaceutical powder.

Preferably, the IC chip member is set in an accommodation portion provided in a carrier tape, in an upward manner with the convex portion facing upward, and is accommodated in an accommodation tape in which an opening side of the accommodation portion is covered with a top tape, and the IC chip member in said upward manner is taken out of said accommodation portion, the taken-out IC chip member is reversed upside down and changed to said downward manner, and thereafter the supply portion supplies the IC chip member.

A manufacturing apparatus for medical tablets manufactures an IC chip member-containing tablet by supplying an IC chip member equipped with an IC on pharmaceutical powder filled in a die hole, thereafter filling pharmaceutical powder onto the IC chip member, and compressing these pharmaceutical powder and the IC chip member from above and below. The manufacturing apparatus for medical tablets comprises a first suction member which suctions and holds the IC chip member; a second suction member which suctions the IC chip member held by said first suction member, from a side opposite to said first suction member; and guide member provided with a through-hole into which the IC chip member is to be inserted. A suction portion of said first suction member is inserted from one side of said through-hole, and a suction portion of said second suction member is inserted from the other side of said through-hole, and the IC chip member is passed from said first suction member to said second suction member within said through-hole.

Preferably, inner shape dimensions of said through-hole are formed to be wide at end portions on said one side and the other side, and to be narrow at an intermediate position, and the IC chip member is passed at said intermediate position.

Preferably, the IC chip member is accommodated in a carrier tape, and said first suction member suctions and holds the IC chip member within the carrier tape, rotates by a set angle, and inserts the IC chip member into said through-hole in said guide member.

Preferably, said guide member includes a plurality of moving guide members, and a drive mechanism which causes the plurality of moving guide members to come close to or separate from each other, and the plurality of moving guide members come close to each other to form said through-hole.

A manufacturing apparatus for medical tablets, which manufactures an IC chip member-containing tablet by supplying an IC chip member on pharmaceutical powder filled in a die hole, further filling pharmaceutical powder onto the IC chip member, and compressing these pharmaceutical powder and the IC chip member from above and below. The manufacturing apparatus for medical tablets comprises a positioning guide which has a through-hole penetrating up and down, and holds the IC chip member within the through-hole; and push-out portion arranged above the positioning guide for pushing out said IC chip member downward. A plurality of protrusions protruding toward a center are provided on an inside of said through-hole, and said IC chip member is held by the protrusions.

Preferably, said plurality of protrusions are convex threads extending along an axial direction of said through-hole.

Preferably, said convex threads are formed to a lower end of said through-hole.

Preferably, said positioning guide is provided to a rotation member, and the IC chip member is pushed from above into said positioning guide located at a receiving position and the IC chip member is held by said protrusions, and, in a state where said positioning guide holding the IC chip member rotates and moves together with rotation of said rotation member and is located above said die hole of a tabletting machine, the held IC chip member is supplied into said die hole by said push-out portion.

A manufacturing method for medical tablets comprises the steps of holding an IC chip member, which has a base plane and a convex portion protruding more on one side than on the other side with respect to the base plane, in a downward manner with the convex portion facing downward, and supplying the IC chip member in the downward manner on pharmaceutical powder filled in a die hole, and manufacturing a tablet containing said IC chip by filling pharmaceutical powder onto said IC chip member, and compressing these pharmaceutical powder and said IC chip member from above and below.

A manufacturing method for medical tablets comprises the steps of a first suction member suctioning and holding an IC chip member, inserting a suction portion of said first suction member from one side of a through-hole, inserting a suction portion of a second suction member from the other side of said through-hole, passing said IC chip member from said suction member to said second suction member within said through-hole to hold said IC chip member, and thereafter supplying said IC chip member on pharmaceutical powder filled in a die hole, and manufacturing a tablet containing said IC chip member by filling pharmaceutical powder onto said IC chip member, and compressing these pharmaceutical powder and said IC chip member from above and below.

A manufacturing method for medical tablets comprises the steps of holding an IC chip member with a plurality of protrusions protruding toward a center provided on an inside of a through-hole in a positioning guide, supplying said IC chip member held within said through-hole on pharmaceutical powder filled in a die hole, and manufacturing a tablet containing said IC chip member by filling pharmaceutical powder onto said IC chip member, and compressing these pharmaceutical powders and said IC chip member from above and below.

Preferably, the manufacturing method for medical tablets further comprises the step of pushing said IC chip member from above into said positioning guide located at a receiving position. The step of supplying said IC chip member includes supplying held said IC chip member into said die hole by a push-out portion, in a state where said positioning guide holding said IC chip member rotates and moves together with rotation of a rotation member and is located above said die hole of a tabletting machine.

A medical tablet including an IC chip member equipped with an IC therein has a first surface and a second surface spaced from each other in an up/down direction. An engraved stamp or cleavage line is formed in said first surface. An engraved stamp or cleavage line is not formed or an engraved stamp or cleavage line shallower than that in said first surface is formed in said second surface. The IC chip member has a base plane and a convex portion protruding more on one side than on the other side with respect to said base plane, and the convex portion is arranged within the medical tablet to face the second face.

BRIEF DESCRIPTION OF DRAWINGS

FIG. 7A is a diagram for explaining an effect and explaining taking out an IC chip 4 from an accommodation tape 7.
FIG. 7B is a diagram for explaining an effect and explaining passing of a reversed IC chip.
FIG. 10A is a diagram for explaining passing of an IC chip from a second suction and hold member to a conveying apparatus.
FIG. 10B is a diagram for explaining passing of an IC chip from a conveying apparatus to a third suction nozzle portion.

FIG. 27A is a diagram for explaining an effect and explaining taking out of an IC chip 1004 from an accommodation tape 1007.

FIG. 27B is a diagram for explaining an effect and explaining passing of a reversed IC chip.

FIG. 29A is a side view representing a conveying apparatus 1021.

FIG. 29B is a front view representing a conveying apparatus 1021.

FIG. 47A is a diagram for explaining an effect and explaining taking out an IC chip 2004 from an accommodation tape 2007.

FIG. 47B is a diagram for explaining an effect and explaining passing of a reversed IC chip.

FIG. 50A is a diagram for explaining passing of an IC chip from a second suction and hold member to a conveying apparatus.

FIG. 50B is a diagram for explaining passing of an IC chip from a conveying apparatus to a third suction nozzle portion.

FIG. 56A is a diagram for explaining a function of a tabletting machine main body 2076.

FIG. 56B is a diagram for explaining a function of a tabletting machine main body 2076.

FIG. 56C is a diagram for explaining a function of a tabletting machine main body 2076.

FIG. 56D is a diagram for explaining a function of a tabletting machine main body 2076.

FIG. 56E is a diagram for explaining a function of a tabletting machine main body 2076.

FIG. 56F is a diagram for explaining a function of a tabletting machine main body 2076.

FIG. 56G is a diagram for explaining a function of a tabletting machine main body 2076.

FIG. 56H is a diagram for explaining a function of a tabletting machine main body 2076.

FIG. 56I is a diagram for explaining a function of a tabletting machine main body 2076.

FIG. 56J is a diagram for explaining a function of a tabletting machine main body 2076.

FIG. 56K is a diagram for explaining a function of a tabletting machine main body 2076.

DESCRIPTION OF EMBODIMENTS

Figure 1:
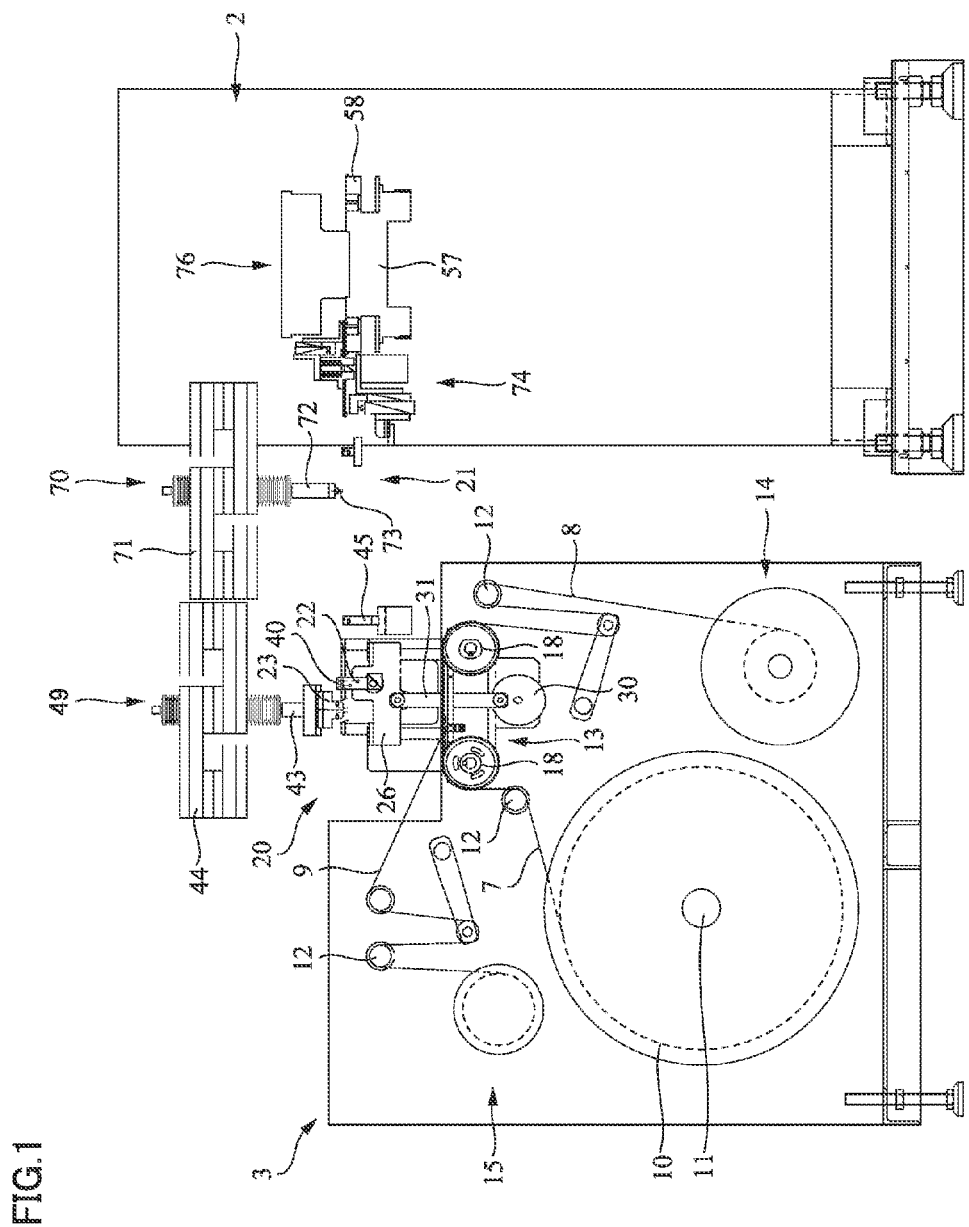
FIG. 1 is a front view representing a favorable one embodiment of a tablet manufacturing apparatus according to the present invention.
Figure 2:
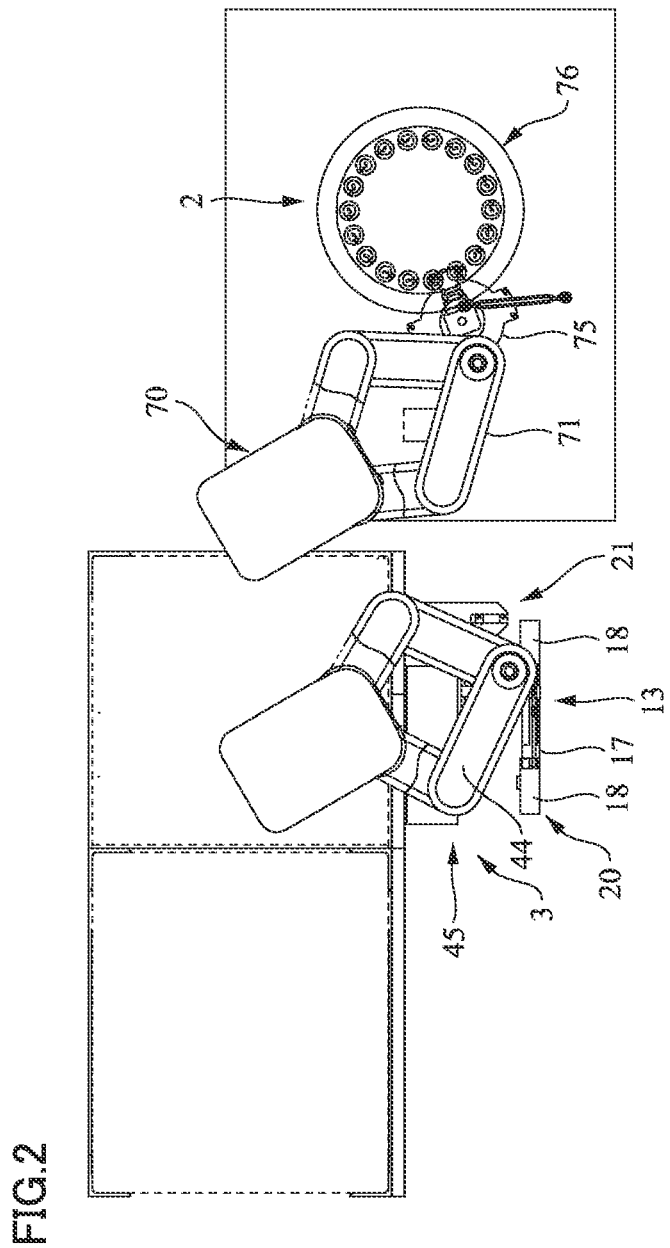
FIG. 2 is a plan view thereof.
Figure 3:
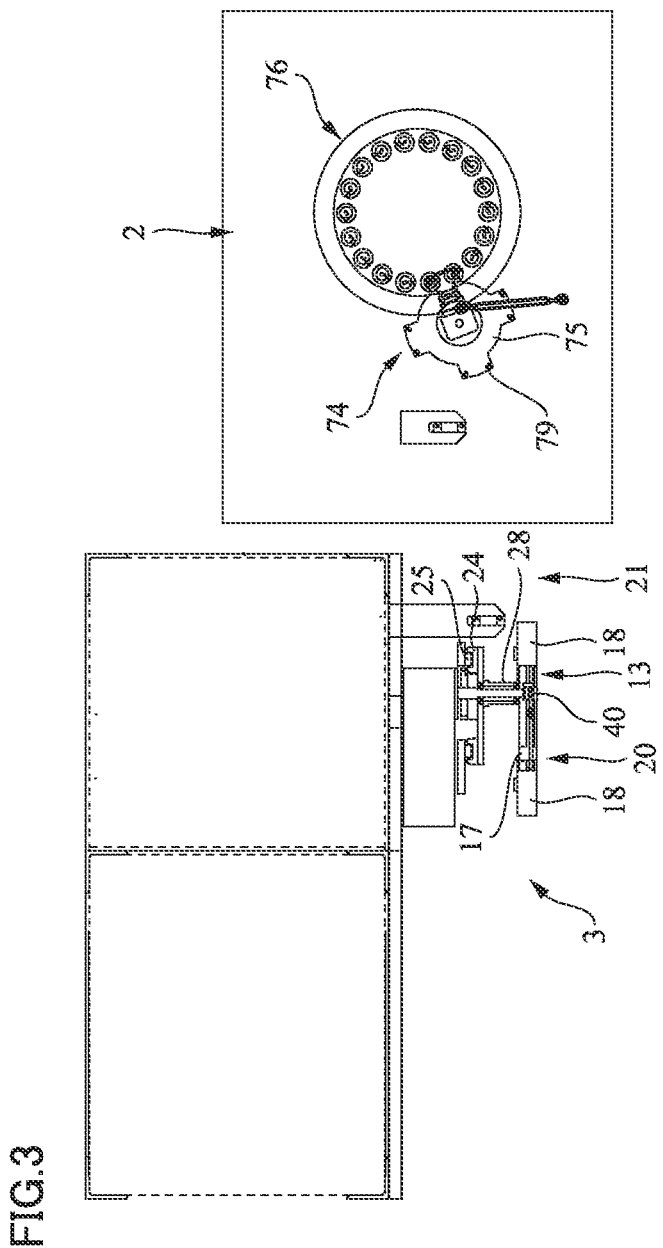
FIG. 3 is a plan view omitting illustration of a robot.
Figure 4A:
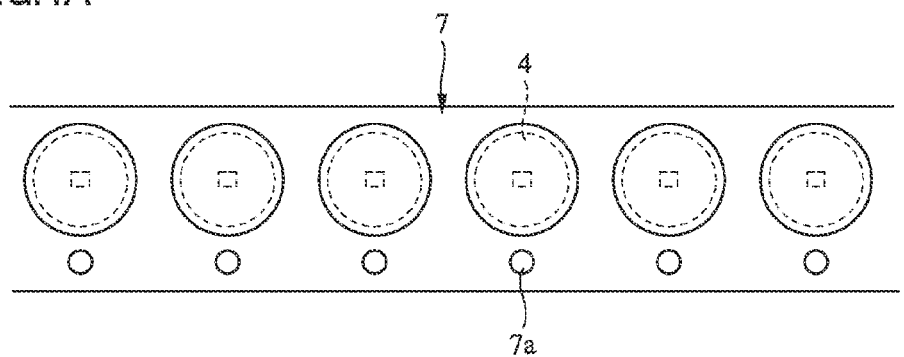
FIG. 4A is a diagram for explaining an IC chip to be supplied.
Figure 4B:
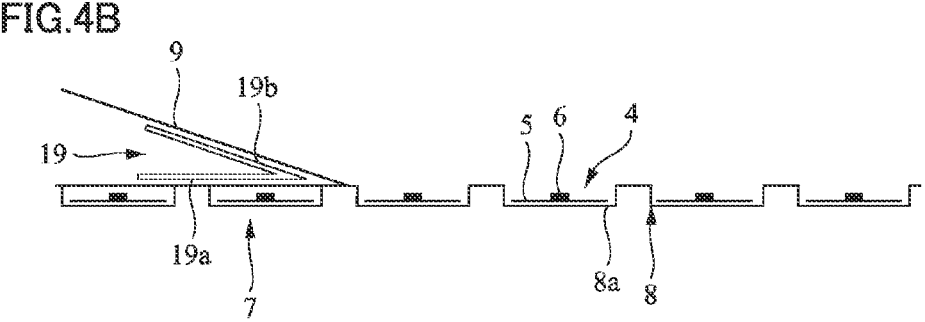
FIG. 4B is a diagram for explaining an IC chip to be supplied.
Figure 4C:
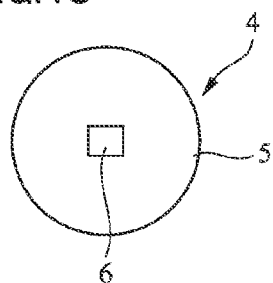
FIG. 4C is a diagram for explaining an IC chip to be supplied.

FIG. 1 is a front view representing a favorable one embodiment of a tablet manufacturing apparatus according to the present invention. FIGS. 2 and 3 are plan views thereof. FIGS. 4A to 4C are diagrams for explaining an IC chip to be supplied in the present embodiment. Drawings subsequent to FIG. 4A are enlarged views of each portion of the apparatus and diagrams for explaining an effect.

As shown in FIGS. 1 to 3, tablet manufacturing apparatus according to the present embodiment includes a tabletting machine 2, and a supply apparatus 3 which conveys and supplies an IC chip to tabletting machine 2. An IC chip 4 conveyed and supplied by the present embodiment has a form in which a chip main body 6 is mounted at a center position of a circular base film 5 as shown in FIGS. 4A to 4C. Base film 5, for example, has a disk-like outer diameter of 3.5 mm, and, for example, includes a function for supporting chip main body 6, an antenna function for communicating information with outside, and the like. Chip main body 6, for example, has a rectangular outer shape of 1 mm square, and an electronic circuit is incorporated therein. Chip main body 6 includes, for example, a storage portion for storing information specifying a tablet into which IC chip 4 is buried, a function for transmitting information stored in the storage portion at a predetermined timing, and the like.

As shown in FIGS. 4A and 4B, IC chips 4 having the above-described configuration are arranged in one line with predetermined intervals on a belt-like accommodation tape 7. Accommodation tape 7 includes a carrier tape 8 having accommodation recesses 8a formed at predetermined intervals and a top tape 9 covering an upper surface carrier tape 8. IC chip 4 is accommodated in accommodation recess 8a. In FIG. 4B, as illustrated on the right side, an upper part of accommodation recess 8a is opened by peeling top tape 9 from carrier tape 8, so that accommodated IC chip 4 can be taken out. IC chip 4 is accommodated in accommodation recess 8a in a state of being in an upward manner where chip main body 6 is located above. Further, accommodation tape 7 has feed holes 7a formed at even pitches along one side edge. This accommodation tape 7 is reeled up by a supply reel 10.

Supply apparatus 3 includes a rotary support shaft 11 for freely rotatably bearing-supporting supply reel 10, which is configured to reel up accommodation tape 7 described above in a rolled formed on its front face, and supply reel 10 is set on rotary support shaft 11. Supply apparatus 3 includes various rollers 12 for defining conveying routes of accommodation tape 7, separated carrier tape 8, and top tape 9 on their front faces, accommodation tape opening portion 13 capable of peeling top tape 9 from carrier tape 8 and taking out IC chip 4 accommodated in accommodation tape 7, a carrier tape collecting portion 14 for collecting carrier tape 8 from which IC chip 4 is taken out, and a top tape collecting portion 15 for collecting top tape 9.

Accommodation tape opening portion 13 includes a guide plate 17 constituting a conveying passage arranged in a horizontal direction at a predetermined position thereabove, a pair sprockets 18 arranged in front and back in the conveying direction of accommodation tape 7 of guide plate 17, and a peeling plate 19 arranged at a predetermined position above guide plate 17.

Figure 5A:
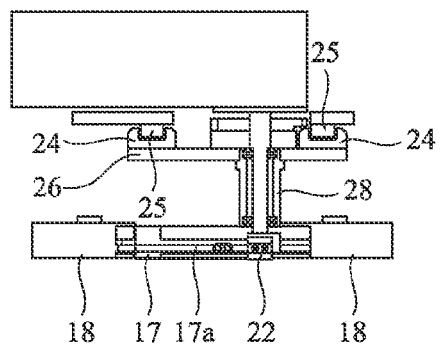
FIG. 5A is a plan view representing an accommodation tape opening portion 13 and an IC chip take-out apparatus 20.
Figure 5B:
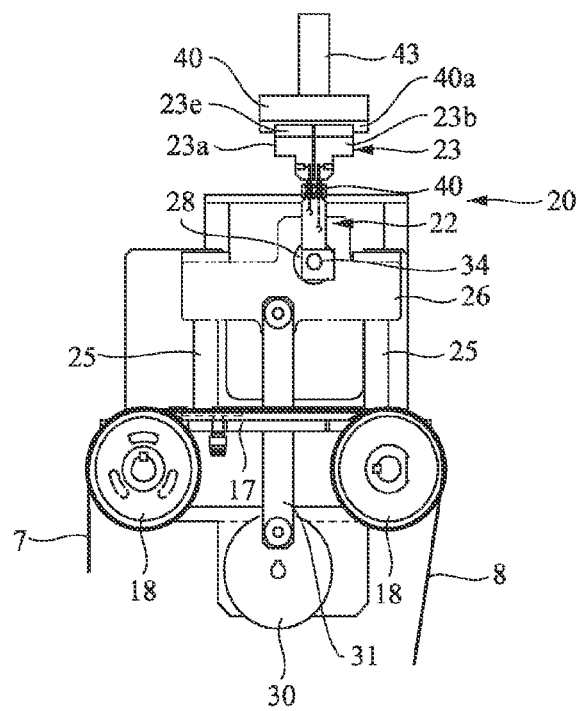
FIG. 5B is a front view representing a tape opening portion 13 and an IC chip take-out apparatus 20.
Figure 5C:
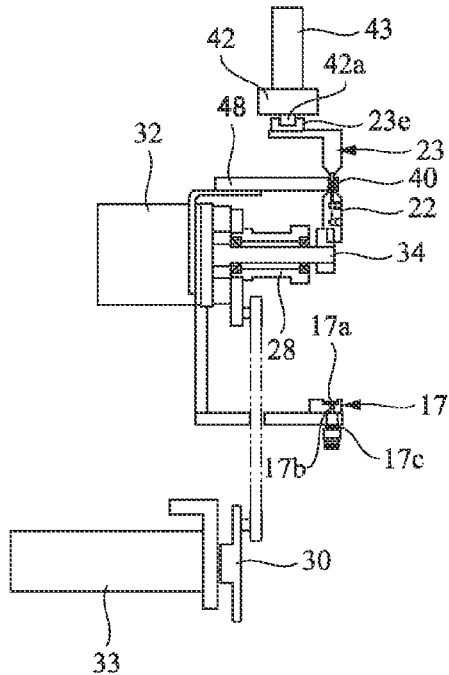
FIG. 5C is a side view representing a tape opening portion 13 and an IC chip take-out apparatus 20.

As shown in FIGS. 5A to 5C in enlargement, guide plate 17 has a concave groove extending in an axial direction in an upper surface. A width of concave groove 17a is equal to or slightly larger than a tape width of accommodation tape 7. Therefore, accommodation tape 7 passes through concave groove 17a, so that it stably moves forward without any lateral displacement. Further, as shown in FIGS. 5A to 5C and FIG. 6, in a section on an upstream side of guide plate 17, a slit 17b is provided in a bottom portion of concave groove 17a, and slit 17b is communicated to a connection pipe 17c mounted to a lower surface of guide plate 17. Connection pipe 17c is coupled to a suction pump not illustrated in the drawings. Accordingly, the part at which slit 17b is opened in the bottom surface of concave groove 17a causes a negative pressure to suction accommodation tape 7, so that stable conveyance can be performed.

Moreover, sprockets 18 have protrusions 18a at a predetermined pitch on its circumferential surface. When accommodation tape 7 is placed over sprockets 18, protrusions 18a penetrate through feed holes 7a of accommodation tape 7 and protrudes above accommodation tape 7. Accordingly, when sprockets 18 are rotated, protrusions 18a within feed holes 7a gives a conveying force to accommodation tape 7, and accommodation tape 7 follows it and moves forward by a predetermined amount. When sprockets 18 are stopped, the forward movement of accommodation tape 7 is also stopped. Sprockets 18 are in conjunction with an unillustrated drive motor such as a servo motor capable of controlling a rotational angle, and an intermittent driving is controlled at a predetermined timing.

As schematically shown in FIG. 4B, a peeling plate 19 includes a reference surface 19a arranged in parallel with a conveyance surface of accommodation tape 7, and a slope surface 19b sloping in a diagonally rearward and upward direction from reference surface 19a. Accommodation tape 7 passes through sprocket 18 on an upstream side, and thereafter passes through a location between guide plate 17 and peeling plate 19, and top tape 9 is bent back from reference surface 19a to slope surface 19b of peeling plate 19 and peeled from carrier tape 8. Accordingly, carrier tape 8 is opened on an upper side of accommodation recess 8a. Then, carrier tape 8 is guided by guide plate 17 and moves horizontally.

It should be noted that, carrier tape 8 passes through accommodation tape opening portion 13 and thereafter passes through a predetermined passage to reach carrier tape collecting portion 14, and is taken up and collected by a take-up reel. Similarly, peeled top tape 9 also passes through a predetermined passage to reach top tape collecting portion 15, and is taken up and collected by a take-up reel.

Above accommodation tape opening portion 13, IC chip take-out apparatus 20 is provided. This IC chip take-out apparatus 20 has a function of taking out IC chip 4 accommodated in opened accommodation tape 7, reversing an manner up and down, and passing it to conveying apparatus 21 in a next stage. In the present embodiment, two front and back IC chips 4 accommodated in accommodation tape 7 are taken out collectively. Therefore, sprockets 18 and the like are operated so as to intermittently convey accommodation tape 7 by a pitch corresponding to two IC chips 4, and performs a control of temporarily stopping IC chip 4 in a state of being located at a take-out position of take-out apparatus 20.

Then, IC chip take-out apparatus 20 includes a first suction and hold member 22 for taking out IC chip 4 accommodated in accommodation tape 7 and reversing up and down of IC chip 4, and a second suction and hold member 23 for receiving IC chip 4 taken out and reversed by first suction and hold member 22 and supplying it to conveying apparatus 21.

First suction and hold member 22 has two first suction nozzle portions 22b formed to protrude at a leading end of an elongated belt-like main body 22a. An arrangement interval of two first suction nozzle portions 22b matches with an arrangement pitch of IC chips 4 in accommodation tape 7. The leading ends of first suction nozzle portions 22b are opened, and the opened parts are in communication with main body 22a and suction passages 22c formed within first suction nozzle portions 22b, and connected to a suction pump not illustrated in the drawing.

Moreover, this first suction and hold member 22 is configured to move up and down and rotate within a vertical plane. As illustrated in enlargement in FIGS. 5A to 5C, this first suction and hold member 22 is bearing-supported through a bearing 28 with respect to a moving plate 26 moving up and down, and moves up and down with moving plate 26. On a back side of moving plate 26, sliders 24 are attached which is mounted to two guide rails 25 extending upward and downward so as to be movable up and down. Moving plate 26 is guided by guide rails 25 and sliders 24 to stably move up and down. A drive mechanism for allowing moving plate 26 to move up and down is configured such that one end of a belt plate-like coupling plate 31 is coupled to an eccentric position of a rotating plate 30 receiving a rotational force of drive motor 33 to rotate, and the other end of coupling plate 31 is coupled to moving plate 26. Accordingly, rotating plate 30 is rotated, so that coupling plate 31 and moving plate 26 move up and down. Then, moving plate 26 reciprocates between the lifted position shown in FIGS. 1 and 5A to 5C and a lowered position shown in FIG. 6.

Moreover, on a back side of moving plate 26, a drive motor 32 as a drive source for rotating first suction and hold member 22 is attached, and drive motor 32 also moves up and down integrally with moving plate 26. A rotational shaft 34 cooperating with an output shaft of drive motor 32 is mounted to bearing 28 arranged so as to protrude to a front side of moving plate 26, and first suction and hold member 22 is fixed to a leading end of rotational shaft 34. Accordingly, rotation of drive motor 32 causes first suction and hold member 22 to rotate. First suction and hold member 22 temporarily stops rotation in a passing manner having a leading end facing upward as shown in FIGS. 1 and 5A to 5C, and a take-out posture having a leading end facing downward as shown in FIG. 6.

Figure 6:
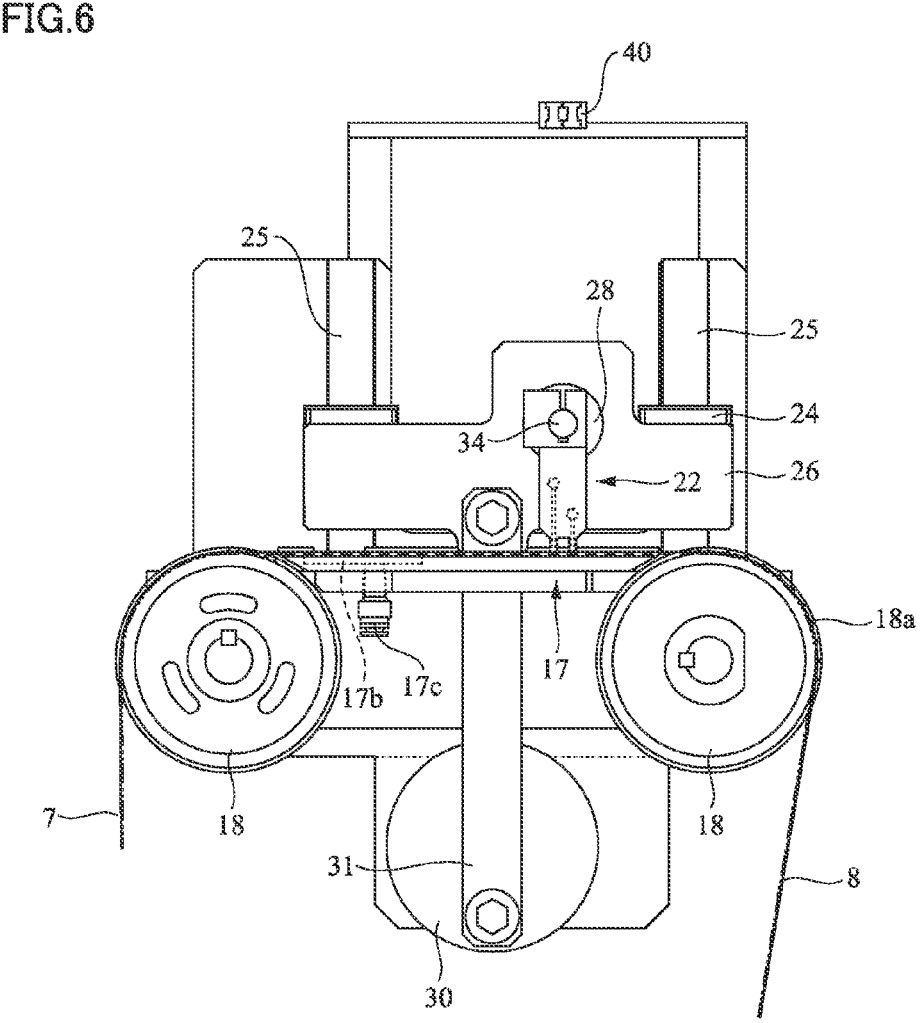
FIG. 6 is an enlarged front view representing a tape opening portion 13 and an IC chip take-out apparatus 20.
Figure 8B:
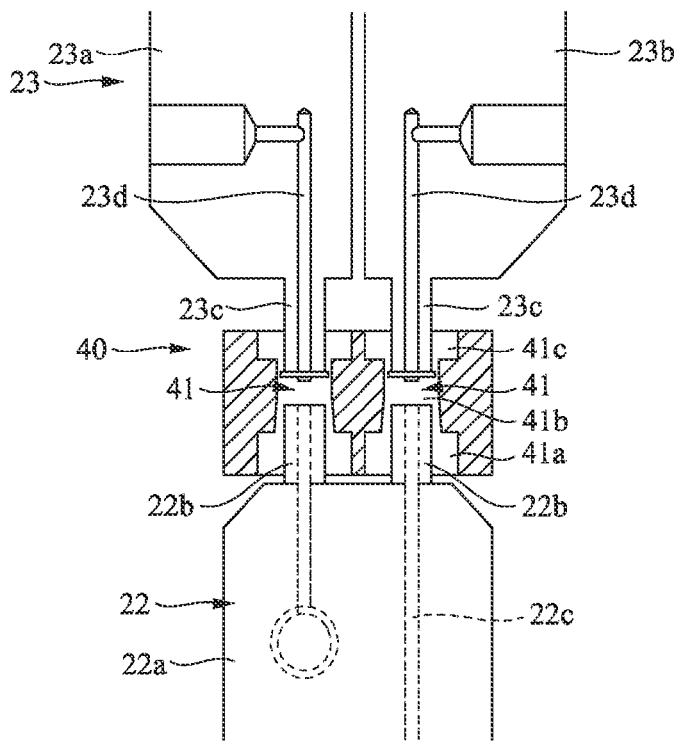
FIG. 8B is an enlarged view representing a main part of FIG. 7B.
Figure 8A:
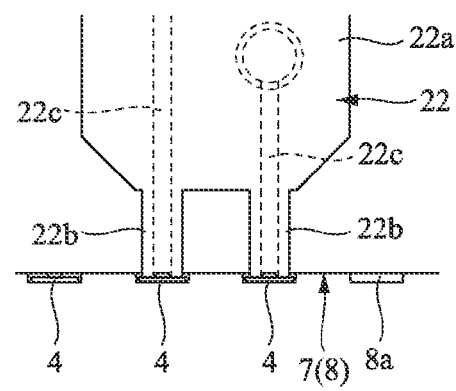
FIG. 8A is an enlarged view representing a main part of FIG. 7A.

Accordingly, when drive motors 32, 33 are controlled appropriately to allow first suction and hold member 22 to be moved downward in a state of a take-out manner of facing downward and located at a lowered position, a leading end of first suction nozzle portion 22b comes into contact with IC chip 4 within accommodation tape 7 (FIGS. 6, 7A, and 8A). When first suction nozzle portion 22b communicates with an unillustrated suction pump in this state, suction is performed by first suction nozzle portion 22b, so that first suction nozzle portion 22b suctions and holds IC chip 4.

Next, when moving plate 26 is moved up while having first suction and hold member 22 in a state of a take-out manner facing downward, first suction nozzle portion 22b of first suction and hold member 22 is located above accommodation tape 7 in a state of suctioning and holding IC chip 4. Accordingly, an operation of taking out IC chip 4 from accommodation tape 7 is completed. Then, moving plate 26 and first suction and hold member 22 further moves up to reach the lifted position. Before reaching this lifted position, first suction and hold member 22 receives driving of drive motor 32 to rotate by 180 degrees, and shifts to a passing manner facing upward. Accordingly, IC chip 4 suctioned by first suction nozzle portion 22b of first suction and hold member 22 is reversed up and down, an manner of facing downward is taken in which chip main body 6 is located on a lower side of base film 5.

As shown in FIGS. 5A to 5C and 7B, a cylindrical guide 40 is arranged at an existing position of first suction nozzle portion 22b of first suction and hold member 22 at the time when first suction and hold member 22 is in a passing manner of facing upward and located at the lifted position. This cylindrical guide 40 is coupled to a machine frame through a support plate 48 extending in a horizontal direction and is fixedly arranged at a desired position. Cylindrical guide 40 includes two through-holes 41 extending upward and downward. Two through-holes 41 have parallel axis centers, and a pitch between axes matches with an arrangement pitch of first suction nozzle portion 22b. Moreover, each through-hole 41 has an inlet region 41a at a lower end, a center region 41b, and an outlet region 41c at an upper end. Inner diameter dimensions of inlet region 41a and outlet region 41c are set to be sufficiently greater than outer shape dimensions of IC chip 4, and inner shape dimensions of center region 41b are set to be substantially equal to or greater than outside dimensions of IC chip 4. Further, an inner circumferential surface of center region 41b is a tapered surface having a narrowest center in an up/down direction. Then, when first suction and hold member 22 moves up while being in a state of a passing manner facing upward, first suction nozzle portion 22b enters inlet region 41a from a lower end of cylindrical guide 40 to reach a lifted position, a leading end of first suction nozzle portion 22b is located within center region 41b. More specifically, it is located near a narrowest center position within center region 41b. Accordingly, the entering of IC chip 4 suctioned and held by first suction nozzle portion 22b into cylindrical guide 40 passes through inlet region 40a having a relatively large room and moves within center region 41b having a gradually reduced inner diameter, so that it can move smoothly to the lifted position.

On the other hand, second suction and hold member 23 includes a first main body 23a and a second main body 23b which come close to and separate from each other in a horizontal direction. Leading ends of first and second main bodies 23a, 23b respectively have second suction nozzle portions 23c. An arrangement space of two second suction nozzle portions 23c in a state where first main body 23a and second main body 23b come close to each other matches with an arrangement space of first suction nozzle portion 22b of first suction and hold member 22. Further, the leading end of second suction nozzle portion 23c is opened, and the opening part communicates with first and second main bodies 23a, 23b, and suction passages 23d formed within second suction nozzle portions 23c and is connected to an unillustrated suction pump.

Moreover, this second suction and hold member 23 is configured to move within a three dimensional space. This movement is performed by a first robot 49. In other words, first robot 49 includes an arm 44 of a SCARA robot moving within a horizontal plane, a support rod 43 attached to a lower surface of a leading end of arm 44 so as to be movable upward and downward, and a base 42 attached to a lower end of support rod 43. The horizontal movement of arm 44 of this SCARA robot and the up and down movement of support rod 43 causes base 42 to be movable to a desired position within the three dimensional space. Then, first main body 23a and second main body 23b constituting second suction and hold member 23 is movably attached through a slider 23e to guide rail 42a provided on a lower surface of base 42. This movement of first main body 23a and second main body 23b is performed, for example, by cylinder driving. Accordingly, base 42 and second suction and hold member 23 supported on the lower surface thereof move within the three dimensional space. Further, first main body 23a and second main body 23b come close to and separate from each other along guide rail 42a.

Specifically, second suction and hold member 23 moves to a position overlapping with cylindrical guide 40 on a horizontal plane in accordance with an operation of arm 44 of the SCARA robot, and moves downward while maintaining that state, so that second suction and hold member 23 reaches a lowered position. At this time, first main body 23a and second main body 23b are close to each other. In this state, as shown in FIGS. 5A to 5C, 7B, and 8B, second suction nozzle portion 23c enters outlet region 41c from an upper end of cylindrical guide 40. Then, having reached a lowermost end position, the leading end of second suction nozzle portion 23c is located within center region 41b. In this state, it is controlled to come close to a leading end of first suction nozzle portion 22b of first suction and hold member 22 located at the lifted position by a certain clearance (for example, about 0.5 mm).

Accordingly, IC chip 4 suctioned and held by first suction nozzle portion 22b waits in a state of being located in a center region 41b of through-hole 41 of cylindrical guide 40, and a lower end of second suction nozzle portion 23c of second suction and hold member 23 having entered from above comes in contact with or close to IC chip 4. Then, suction with second suction nozzle portion 23c is started, and suction with first suction nozzle portion 22b is stopped at an appropriate timing, so that suctioning and holding of IC chip 4 is shifted to the side of second suction and hold member 23.

As can be seen, the present embodiment is characterized in performing a transfer of IC chip 4 from first suction and hold member 22 to second suction and hold member 23 within cylindrical guide 40. Since IC chip 4 has a thin shape of base film 5 with a small diameter of 3.5 mm, it cannot be firmly held by the suction and hold member. Therefore, if passing between first suction and hold member 22 and second suction and hold member 23 is performed in a state where IC chip 4 is exposed, there is a likelihood that passing cannot be performed smoothly and IC chip 4 is dropped. However, according to the present embodiment, the passing process is performed inside of cylindrical guide 40, so that the passing can be performed assuredly.

After that, first suction and hold member 22 moves down while maintaining a passing manner. When first suction nozzle portion 22b goes out of cylindrical guide 40, first suction and hold member 22 rotates by 180 degrees to take a take-out manner and returns to a lowered position at an appropriate timing, and prepares for taking out next IC chip. On the other hand, second suction and hold member 23 which has received IC chip 4 moves up with support rod 43 moving up, and second suction nozzle portion 24 is located above cylindrical guide 40. After that, an operation of arm 44 of the SCARA robot causes second suction and hold member 23 to move in a horizontal direction to reach a conveying position of conveying apparatus 21.

Figure 9A:
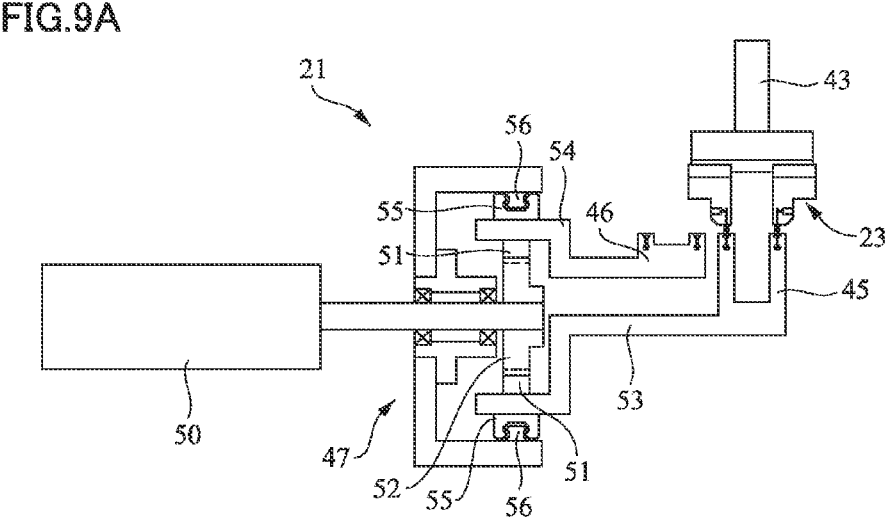
FIG. 9A is a side view representing a conveying apparatus 21.
Figure 9B:
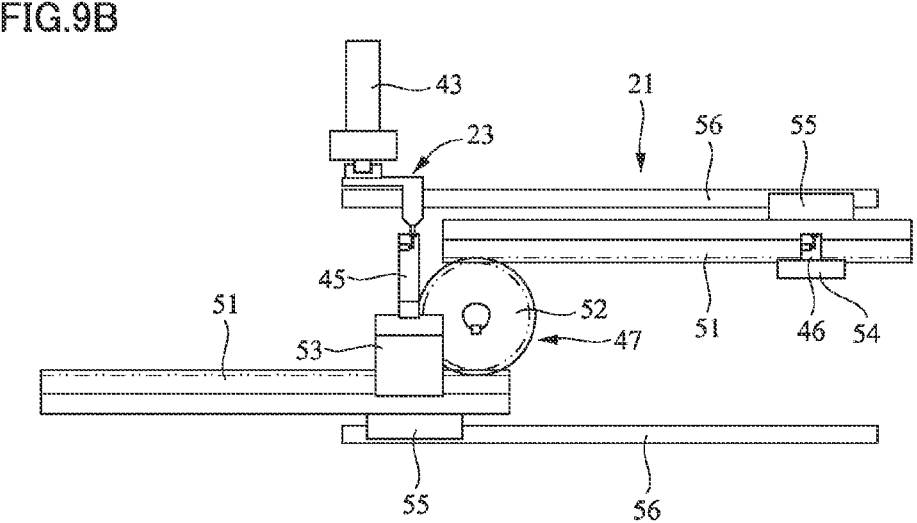
FIG. 9B is a front view representing a conveying apparatus 21.

As shown in FIGS. 9A and 9B, conveying apparatus 21 includes a first receiving portion 45 and a second receiving portion 46 for receiving two IC chips 4 conveyed by second suction and hold member 23 suctioning and holding IC chips 4, and a drive mechanism 47 for moving these first receiving portion 45 and second receiving portion 46 forward and backward. As shown in FIGS. 10A and 10B by enlargement, first receiving portion 45 includes recesses 45b for accommodating IC chip 4 in upper surfaces of two bifurcated pillar portions 45a facing upward. A space between pillar portions 45a (recesses 45b) is in conformity with a tabletting machine in a next stage and set to be longer than an arrangement pitch (an arrangement space of first suction nozzle portion 22b and second suction and hold member 23) of IC chips 4 in accommodation tape 7. Moreover, a bottom surface of recess 45b communicates with a suction passage 45 formed within pillar portion 45a and is connected to an unillustrated suction pump. Accordingly, IC chip 4 set within recess 45b is suctioned and held within recess 45b. Even when first receiving portion 45 moves forward, IC chip 4 moves forward with first receiving portion 45 while being set within recess 45b.

Similarly, second receiving portion 46 includes recesses 46b accommodating IC chip 4 in an upper surface of two bifurcated pillar portions 46a facing upward. A space between pillar portions 46a (recesses 46b) is in conformity with a tabletting machine in a next stage and set to be longer than an arrangement pitch (an arrangement space of first suction nozzle portion 22b and second suction and hold member 23) of IC chip 4 in accommodation tape 7. Moreover, a bottom surface of recess 46b communicates with a suction passage 46c formed within pillar portion 46a and is connected to an unillustrated suction pump. Accordingly, IC chip 4 set within recess 46b is suctioned and held within recess 46b. Even when second receiving portion 46 moves forward, IC chip 4 moves forward with second receiving portion 46 while being set in recess 46b.

Drive mechanism 47 of first receiving portion 45 and second receiving portion 46 includes a drive motor 50, and a rack 51 and a pinion 52 receiving an output of drive motor 50 and converting it into a reciprocal linear motion. First receiving portion 45 and second receiving portion 46 cooperate with rack 51 respectively through coupling plates 53, 54 and move in a reverse direction. In other words, second receiving portion 46 moves backward when first receiving portion 45 moves forward, and second receiving portion 46 moves backward when first receiving portion 45 moves forward. In other words, for example, second receiving portion 46 is at a conveying-out position when first receiving portion 45 is at a conveying-in position. Moreover, for example, second receiving portion 46 is at a conveying-in position when first receiving portion 45 is at a conveying-out position. Moreover, sliders 55 are coupled to a lower surface of coupling plate 53 and an upper surface of coupling plate 54. This sliders 55 are mounted respectively to corresponding guide rails 56 and guide a forward and backward movement of rack 51 and each receiving portion 45, 46 along with rotation of pinion 52.

Second suction and hold member 23 having received IC chip 4 moves on a horizontal plane by means of arm 44 of the SCARA robot and is located above first receiving portion 45 or second receiving portion 46 located at the conveying-in position. As described above, since first receiving portion 45 and second receiving portion 46 move forward and backward in directions opposite to each other, first robot 49 controls an operation of arm 44 of the SCARA robot to allow second suction and hold member 23 to be positioned alternately above the conveying-in position of first receiving portion 45 and the conveying-in position of second receiving portion 46.

As described above, since a space between pillar portions 45a (recesses 45b) of first receiving portion 45 and a space between pillar portions 46a (recesses 46b) of second receiving portion 46 are widened, first robot 49, during the horizontal movement of second suction and hold member 23 by means of arm 44 of the SCARA robot or at the time of being located above the conveying-in position, controls first main body 23a and second main body 23b of second suction and hold member 23 to be separated from each other to widen the space of second suction nozzle portion 23c. The widened space of second suction nozzle portion 23c is set to be equal to the space of recesses 45b, 46b.

Then, in such a state where first main body 23a and second main body 23b are separated from each other, when support rod 43 is moved downward, as shown in FIG. 10A for example, a lower end of second suction nozzle portion 23c of second suction and hold member 23 enters recesses 45b of first receiving portion 45, so that IC chip 4 suctioned and held in a downward manner is set within the recess 45b. Then, when the suction on the side of second suction and hold member 23 is released at an appropriate timing, IC chip 4 is transferred to recesses 45b of first receiving portion 45. Moreover, first receiving portion 45 starts suction in advance or at an appropriate timing, and suctions and holds IC chip 4 within recessed 45b.

Second suction and hold member 23 having completed a supply of IC chip 4 to first receiving portion 45 in such a manner returns to a receiving position within cylindrical guide 40 by an operation of first robot 49, and supplies the next passed IC chip to recess 46b of second receiving portion 46.

On the other hand, first receiving portion 45 having received the supply of IC chip 4 moves forward and is located at a conveying-out position. IC chip 4 within recess 45b of first receiving portion 45 having reached the conveying-out position is suctioned and held by second robot 70 and transferred to tabletting machine 2. Second robot 70 includes an arm 71 of the SCARA robot moving within a horizontal plane, a support member 72 attached to a leading end lower surface of arm 71 so as to be movable upward and downward, and a pair of suction nozzle portions 73 attached to the lower end of support member 72. A leading end of third suction nozzle portion 73 is opened, and the opened part communicates with suction passage 73a formed within third suction nozzle portion 73 and is connected to an unillustrated suction pump. Then, the horizontal movement of arm 71 of the SCARA robot and the upward and downward movement of support member 72 causes third suction nozzle portions 73 to be movable to a desired position within a three dimensional space. Further, a space of the pair of third suction nozzle portions 73 is in conformity with an arrangement space between pillar portions 45a (recesses 45b) of first receiving portion 45 and an arrangement space between pillar portions 46a (recesses 46b) of second receiving portion 46.

Accordingly, suction by means of a suction pump is performed in a state where a lower end of third suction nozzle portion 73 has reached within recess 45b of first receiving portion 45 or recess 46b of second receiving portion 46 located at the conveying-out position by means of an operation of second robot 70. When the suction by means of a vacuum pump on the side of first receiving portion 45 or second receiving portion 46 is released, IC chip 4 is suctioned and held on the side of third suction nozzle portion 73 (refer to FIG. 10B).

Figure 11A:
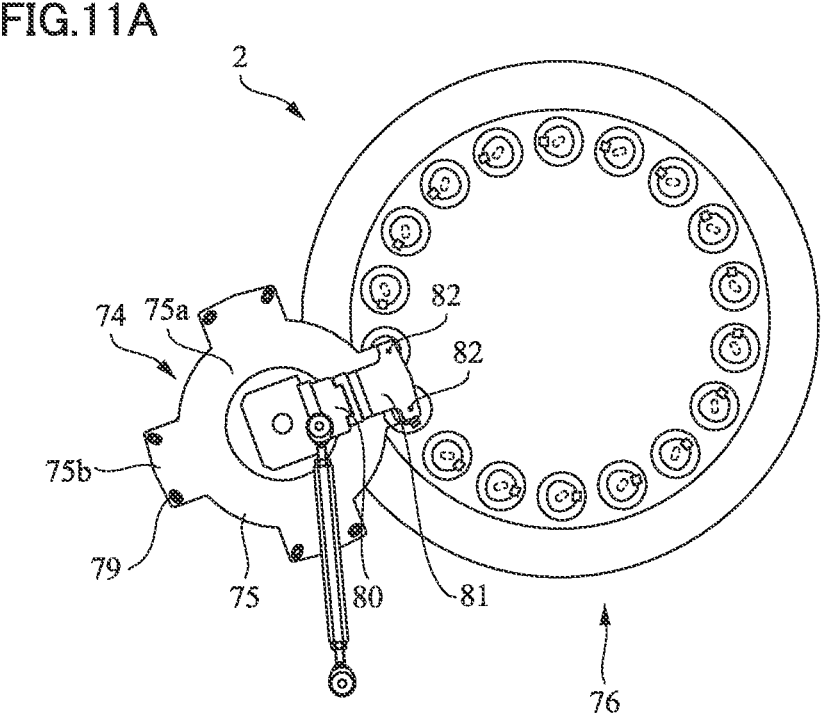
FIG. 11A is a front view representing a tabletting machine.
Figure 11B:
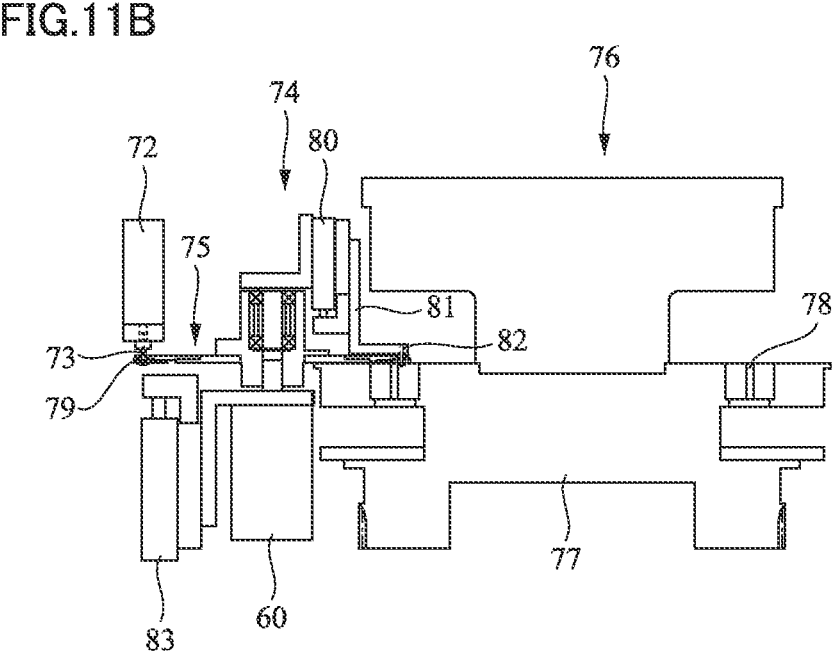
FIG. 11B is a front view representing a tabletting machine.

Next, when third suction nozzle portion 73 suctioning and holding IC chip 4 is moved upward, horizontally, and downward by an operation of second robot 70, as shown in FIGS. 2 and 11B, it is located within an IC chip receiving portion 79 of a rotary table 75 of an IC chip supply apparatus 74 arranged on the conveying-in side of tabletting machine 2. When the suction of third suction nozzle portion 73 is released in this state, IC chip 4 is supplied to IC chip receiving portion 79.

Tabletting machine 2 includes the above-described IC chip supply apparatus 74 and a tabletting machine main body 76. Tabletting machine main body 76 is similar to a conventionally existing tabletting machine which fills pharmaceutical powder into a plurality of die holes 78 arranged at predetermined intervals on a circumference along an outer edge portion of rotating plate 77 and compresses and shapes the filled pharmaceutical powder by means of a lower pestle and an upper pestle to manufacture tablets. In the present embodiment, to manufacture an IC chip-containing tablet, a function of supplying IC chip 4 by means of IC chip supply apparatus 74 onto a predetermined amount of pharmaceutical powder supplied into die hole 78, further supplying pharmaceutical powder onto IC chip 4, and compressing and shaping these pharmaceutical powder and IC chip from above and below function is provided. Details of manufacturing processes of tablets will be described later.

IC chip supply apparatus 74 as a main part of the present invention includes rotary table 75 as described above, and aligns IC chips 4 supplied to rotary table 75 within die holes 78 of tabletting machine main body 76. Rotary table 75 receives a rotational force of drive motor 60 to rotate. In the present embodiment, it is controlled to rotate intermittently at 90 degrees intervals. Moreover, rotary table 75 includes protruding parts 75b protruding outward at 90 degrees intervals on an outer circumference of a plate-like main body 75a. This protruding part 75b is provided with IC chip receiving portions 79. From the side of supply apparatus 3, IC chips 4 are supplied in increments of two, so that two IC chip receiving portions 79 are provided at each protruding part 75b. In the present embodiment, a position rotated by 180 degrees from an IC chip receiving position from supply apparatus 3 on an upstream side is a supplying position of IC chips 4 to tabletting machine main body 76. Then, it is temporarily stopped at a position rotated by 90 degrees from the IC chip receiving position. At this time, for example, it is favorable to provide an inspection apparatus which performs an inspection on whether or not IC chips are correctly supplied to IC chip receiving portion 59.

Figure 12:
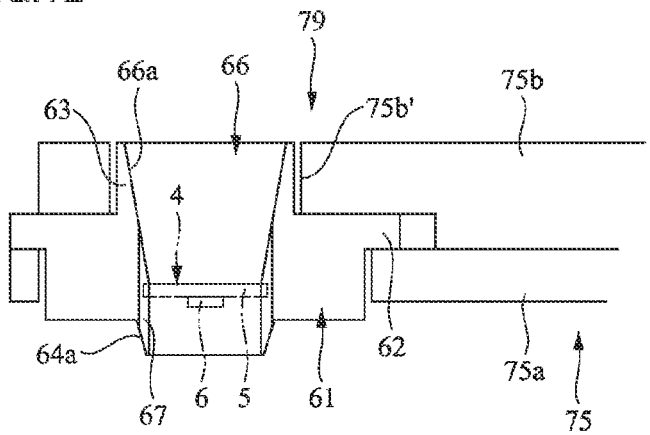
FIG. 12 is an enlarged view representing a main part of an IC chip supply apparatus 74.
Figure 13A:
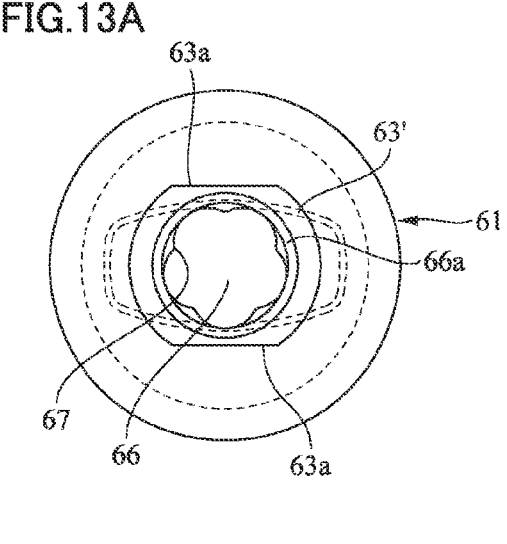
FIG. 13A is a plan view representing a positioning guide 61.
Figure 13C:
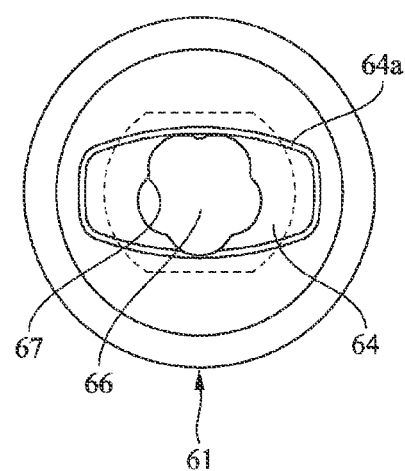
FIG. 13C is a bottom view representing a positioning guide 61.
Figure 13B:
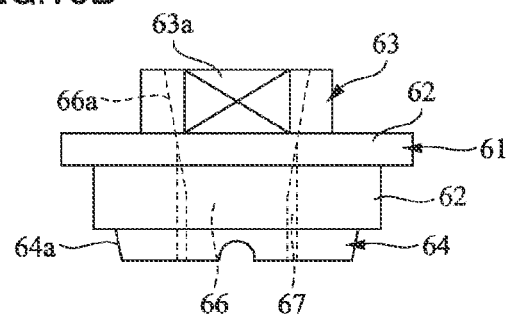
FIG. 13B is a front view representing a positioning guide 61.

As shown in FIG. 12 by enlargement, a through-hole 75b' is provided which penetrates up and down at a specified position of protruding part 75b of rotary table 75, and a positioning guide 61 is mounted to through-hole 75b'. This positioning guide 61 constitutes IC chip receiving portion 59. Positioning guide 61 has a ring-like shape as a basic shape having a through hole penetrating up and down as also shown in FIGS. 13A to 13C.

Positioning guide 61 includes a flange portion protruding radially outward at an upper circumferential side surface of cylindrical main body 62, and a convex portion 63 protruding upward is provided at a center of the upper surface of main body 62. Convex portion 63 includes a flat surface 63a on it side surface. Convex portion 63 is inserted into through-hole 75b' of protruding part 75b, and flange portion 63 is sandwiched and held by protruding part 75b and main body 75a. Accordingly, movement in an axial direction of positioning guide 61, in other words, movement in an up/down direction is prevented, so that separation of positioning guide 61 from rotary table 75 is prevented. Further, an inner circumferential surface shape of through-hole 75b' of protruding part 75b is set to be substantially match with an outer circumferential surface shape of convex portion 63 of positioning guide 61. Accordingly, rotation of positioning guide 61 about an axis is prevented. Therefore, positioning guide 61 is held at a correct position and in a correct manner by rotary table 75.

Through-hole 66 provided in positioning guide 61 is set to be a tapered surface 66a having a circular cross section in an upper region with a diameter gradually increasing as it goes upward. This upper region is a region in which convex portion 63 is mainly formed. An inner diameter of through-hole 66 at an upper end of convex portion 63 is set to be larger than an outer diameter of IC chip 4. IC chip 4 suctioned and held by third suction nozzle portion 73 enters into through-hole 66 of positioning guide 61 in accordance with a downward movement of third suction nozzle portion 73 while tapered surface 66a guides the entering and prompts a smooth downward movement.

Moreover, the inner circumferential surface in the portion of main body 62 of through-hole 66 forms a plurality of protrusions 67 protruding toward a center. In the present embodiment, five protrusions 67 are provided. However, the number may be, for example, three, or other suitable number may be used. The leading end position of protrusion 67 is set to be located on an imaginary circumference being concentric with through-hole 66 and having a predetermined diameter. This predetermined diameter is set be equal to or slightly smaller than a diameter of IC chip 4. Accordingly, a circumferential edge of IC chip 4 inserted into through-hole 66 of positioning guide 61 is supported by protrusion 67 and held in a state where a center of IC chip 4 and a center of positioning guide 61 (through-hole 66) are matched. Accordingly, the positioning is performed with a high accuracy. Moreover, it is preferable to manufacture positioning guide 61 with an elastic body such as rubber since it can hold IC chip 4 more firmly. Further, preferably, protrusion 67 is arranged at equal intervals in the circumferential direction. It is preferable since IC chips 4 are supported evenly.

Further, in the present embodiment, a push-in portion 64 protruding downward is provided at a lower surface of main body 62. A planar shape of this push-in portion 64 is substantially elliptical as shown in FIG. 13C. In this example, both ends on the large-diameter side of the elliptical shape is collapsed to be flat. The planar shape of this push-in portion 64 is based on a shape of a tablet to be manufactured and is formed to be slightly smaller than that of the tablet. In other words, it has a shape which is slightly smaller than a cross sectional shape of die hole 78 formed in tabletting machine main body 76. Moreover, a circumferential surface of push-in portion 64 has a tapered surface 64a which is smaller on a lower side. Further, in the present embodiment, protrusion 67 formed on the inner circumferential surface of through-hole 66 is formed to a lower end of this push-in portion 64.

Figure 14A:
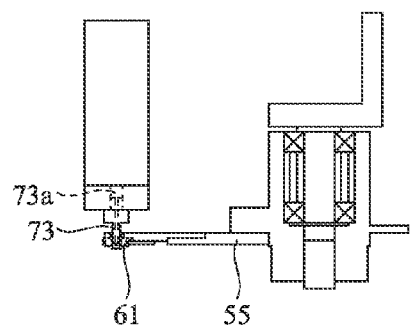
FIG. 14A is a diagram for explaining an operation of an IC chip supply apparatus 74.
Figure 15A:
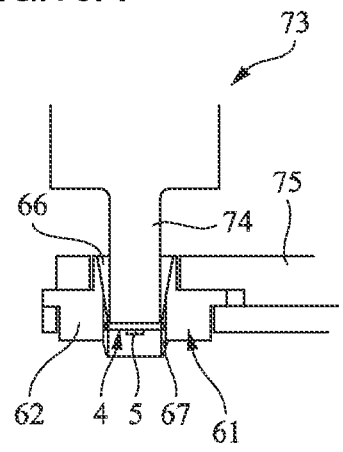
FIG. 15A is an enlarged view representing a main part of FIG. 14A.

Next, an operation of supplying IC chip 4 from supply apparatus 3 to IC chip supply apparatus 74 and an operation of supplying IC chip 4 to tabletting machine 2 will be described, and a configuration of IC chip supply apparatus 74 will be described. FIGS. 14A and 15A show a state where a leading end of third suction nozzle portion 73 of supply apparatus 3 is inserted into positioning guide 61 constituting IC chip receiving portion 59. As shown in the drawings, second suction and hold member 23 moves downward, and the leading end of third suction nozzle portion 73 in a state of suctioning and holding IC chip 4 enters into through-hole 66 of positioning guide 61 and stops at an appropriate position of main body 62. At this appropriate position, IC chip 4 is supported by protrusion 67. Since the suction by third suction nozzle portion 73 is performed until reaching this stopping position, IC chip 4 moves downward while maintaining a horizontal state in a downward manner where chip main body 6 is located on a lower side, IC chip 4 is in contact with a plurality of protrusions 67 in a horizontal manner at a lower stopping position of third suction nozzle portion 73.

Next, the suction by third suction nozzle portion 73 is released, and third suction nozzle portion 73 moves upward and is separated from positioning guide 61 to take next IC chip. On the other hand, IC chip 4 in a downward manner remaining in positioning guide 61 is supported in a state of maintaining a horizontal manner by protrusions 67 of positioning guide 61. Moreover, as described above, taking of a center position of IC chip 4 is also performed at a high accuracy.

Figure 14B:
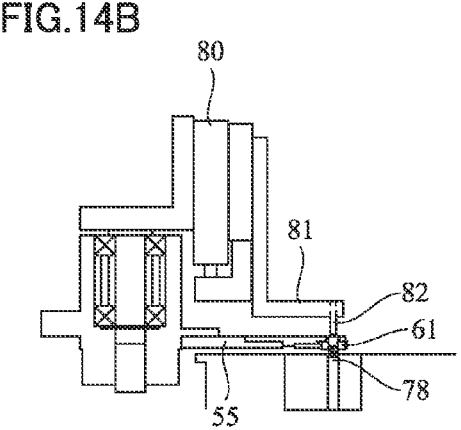
FIG. 14B is a diagram for explaining an operation of an IC chip supply apparatus 74.
Figure 15B:
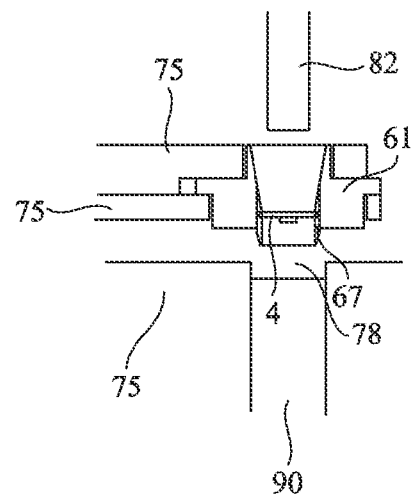
FIG. 15B is an enlarged view representing a main part of FIG. 14B.

The drawings subsequent to FIGS. 14B and 15B shows a supplying position to tabletting machine 2 at which rotary table 75 is rotated by 180 degrees from the states of FIGS. 14A and 15A. At this supplying position, two pushers 82 are formed to be suspended on a lower surface of the leading end of an L-shaped plate 81 which receives driving of a first cylinder 80 and moves up and down. Two pushers 82 are in conformity with the arrangement pitch of two positioning guides 61 which are adjacent in the circumferential direction, and are adjusted so that an axis center of each positioning guide 61 and an axis center of pusher 82 are matched at the time when the rotary table is temporarily stopped.

Further, first cylinder 80, L-shaped plate 81, pusher 82, and rotary table 75 can move up and down integrally. Then, the up and down movement is performed by receiving driving of second cylinder 83.

Accordingly, the position of rotary table 75 or pusher 82 can be changed by appropriately switching the reciprocating operation of first cylinder 80 and second cylinder 83. For example, FIGS. 14B and 15B shows a state where first cylinder 80, L-shaped plate 81, pusher 82, and rotary table 75 are positioned at the lifted position by means of second cylinder 83, and where pusher 82 is also positioned at the lifted position by means of first cylinder 80. In this state, rotary table 75 is separated from an upper surface of rotating plate 77 of tabletting machine main body 76, and positioning guide 61 is also separated from an upper surface of rotating plate 77. Moreover, the lower surface of pusher 82 is located above positioning guide 61, and pusher 82 and IC chip 4 in a downward manner supported by positioning guide 61 are in a non-contact state. This state is an initial state of rotary table 75 which is rotated, reached the supplying position, and temporarily stopped.

Figure 14C:
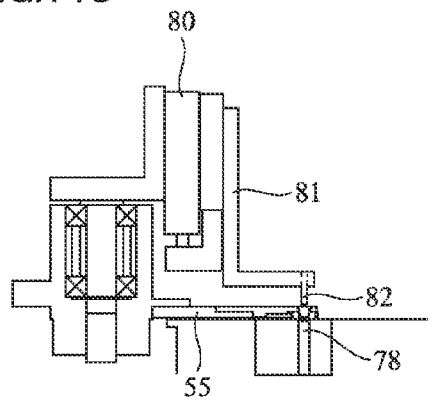
FIG. 14C is a diagram for explaining an operation of an IC chip supply apparatus 74.
Figure 15C:
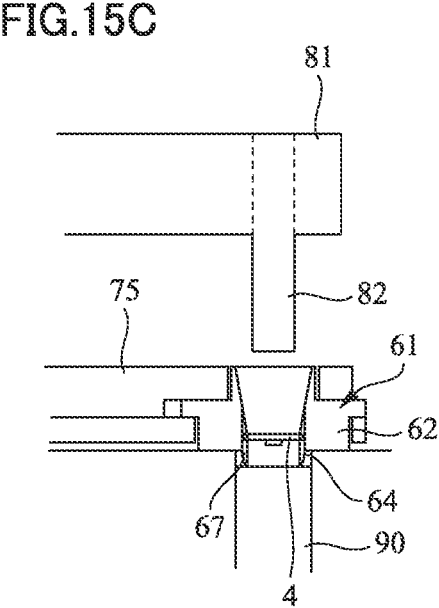
FIG. 15C is an enlarged view representing a main part of FIG. 14C.

Next, only second cylinder 83 is operated to allow first cylinder 80, L-shaped plate 81, pusher 82, and rotary table 75 to be positioned at the lowered position. Then, as shown in FIGS. 14C and 15C, rotary table 75 comes close to an upper surface of rotating plate 77 of tabletting machine main body 76, and a lower surface of main body 62 of positioning guide 61 comes into contact with an upper surface of rotating plate 77. Further, push-in portion 64 enters die hole 78, and comes into contact with pharmaceutical powder filled in die hole 78. Moreover, at this time, since first cylinder 80 remains in the initial state, the relative positional relationship between pusher 82 and positioning guide 61 does not change, and the lower surface of pusher 82 is located above positioning guide 61, and pusher 82 and IC chip 4 in a downward manner supported by positioning guide 61 remain in a non-contact state.

Figure 14D:
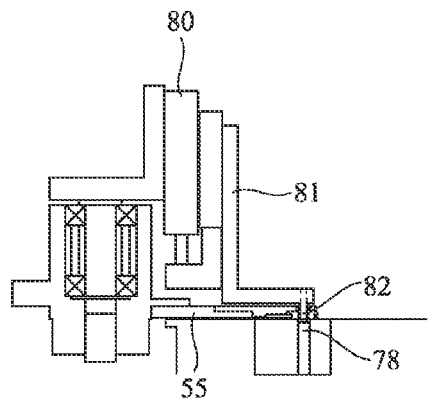
FIG. 14D is a diagram for explaining an operation of an IC chip supply apparatus 74.
Figure 15D:
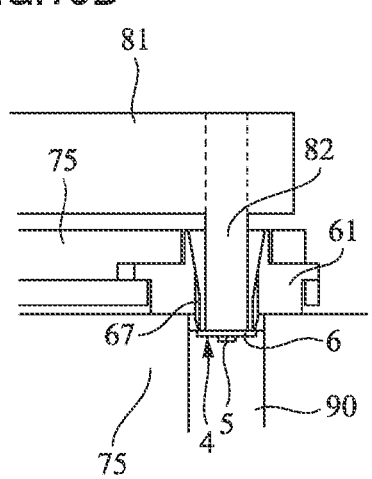
FIG. 15D is an enlarged view representing a main part of FIG. 14D.

After that, first cylinder 80 is operated while second cylinder 83 maintains the above-described state, and pusher 82 moves downward. Then, as shown in FIGS. 14D and 15D, the lower end of pusher 82 reaches the lower end of positioning guide 61, in other words, the lower end of push-in portion 64, so that IC chip 4 is forced downward by pusher 82 and pushed out from positioning guide 61 and pushed into pharmaceutical powder 90. Also at this downward movement of IC chip 4 by pusher 82, IC chip 4 moves while maintaining a horizontal state and taking out of a center position by means of protrusions 67 of positioning guide 61. Accordingly, when IC chip 4 is pushed out from positioning guide 61 and finally pushed into pharmaceutical powder 90 to be supplied, it is supplied at a high accuracy to a center of a surface of pharmaceutical powder 90 filled in die hole 78. Moreover, since IC chip 4 is pushed into pharmaceutical powder 90 before being compressed by pusher 82 of the tabletting machine main body, the positional displacement is suppressed.

Further, since IC chip 4 is pushed into pharmaceutical powder 90 in a downward manner where chip main body 6 is located on a lower side, chip main body 6 is further inserted into pharmaceutical powder 90 with respect to the surface of pharmaceutical powder 90 in contact with, for example, base film 5. Therefore, even when IC chip 4 attempts to move in the horizontal direction, chip main body 6 serves as a wedge, so that the positional displacement due to the movement in the lateral direction can be suppressed assuredly.

Further, in the present embodiment, as described above, the horizontal state and the taking of the center position is performed at a high accuracy by means of protrusions 67 of positioning guide 61. Thus, since IC chip 4 can be supplied assuredly to the center of pharmaceutical powder 90, the taking of the position is ensured without performing an inspection on whether or not IC chip 4 is supplied to a correct position after the supply. Accordingly, even in the case where an inspection apparatus is provided, it may be for example a simple sensor which confirms presence of supply, so that an apparatus which cannot reserve a space region for providing the inspection apparatus can be used.

Figure 16A:
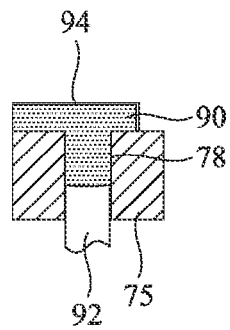
FIG. 16A is a diagram for explaining a function of a tabletting machine main body 76.
Figure 16B:
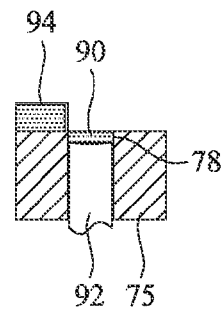
FIG. 16B is a diagram for explaining a function of a tabletting machine main body 76.
Figure 17A:
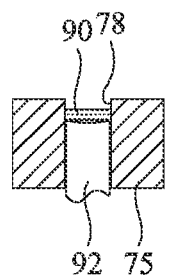
FIG. 17A is a diagram for explaining a function of a tabletting machine main body 76.
Figure 17B:
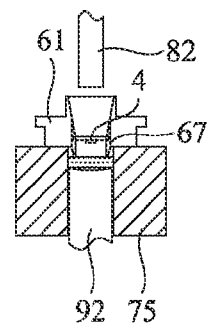
FIG. 17B is a diagram for explaining a function of a tabletting machine main body 76.

FIGS. 16A to 20C represent an operation of a main body of tabletting machine 2. As shown in FIG. 16A, on the lower side of die hole 78, a lower pestle 92 is fitted from a lower side in a slidably upward and downward. As shown in FIG. 20A, on an upper side of die hole 78, an upper pestle 93 is provided so as to be movable up and down. As shown in FIG. 16A, firstly, in a state where lower pestle 92 is lowered in die hole 78, pharmaceutical powder filling apparatus 94 fills pharmaceutical powder 90 into die hole 78. Next, as lower pestle 92 moves upward, a supply by pharmaceutical powder filling apparatus 94 is cut, and a certain amount of pharmaceutical powder 90 is filled in a leveled state into a space of die hole 78 formed in an upper side of lower pestle 92 (FIG. 16B). After that, lower pestle 92 is lowered by a predetermined quantity, so that the surface of pharmaceutical powder 90 is slightly lowered from an upper surface of rotating plate 75 (FIG. 17A).

Figure 18A:
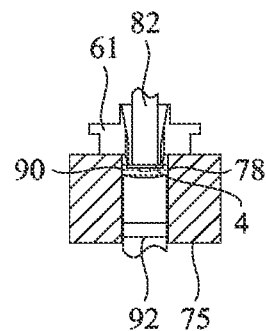
FIG. 18A is a diagram for explaining a function of a tabletting machine main body 76.
Figure 18B:
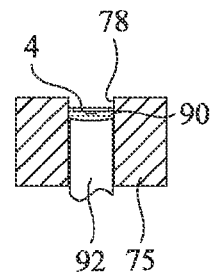
FIG. 18B is a diagram for explaining a function of a tabletting machine main body 76.

In this state, with IC chip supply apparatus 74 described above, positioning guide 61 having IC chip 4 set in a downward manner enters die hole 78 (FIG. 17B), and pusher 82 pushes out IC chip 4 and pushes it into pharmaceutical powder 90 (FIG. 18A).

Figure 19A:
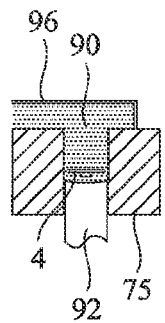
FIG. 19A is a diagram for explaining a function of a tabletting machine main body 76.
Figure 19B:
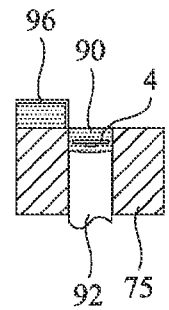
FIG. 19B is a diagram for explaining a function of a tabletting machine main body 76.

Next, rotating plate 75 is rotated to allow the die hole located at the supplying position to shift to the next step (FIG. 18B), and pharmaceutical powder 90 is filled into die hole 78 by pharmaceutical powder filling apparatus 94 in a state where lower pestle 92 is positioned on a lower side within die hole 78 (FIG. 19A). Next, lower pestle 92 is lifted, and a supply by pharmaceutical powder filling apparatus 94 is cut, and a certain amount of pharmaceutical powder 90 is filled in a space of die hole 78 formed on an upper side of lower pestle 92 in a leveled state (FIG. 19B).

Figure 20A:
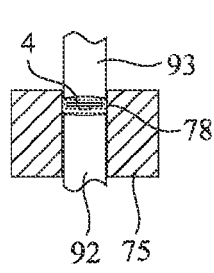
FIG. 20A is a diagram for explaining a function of a tabletting machine main body 76.
Figure 20B:
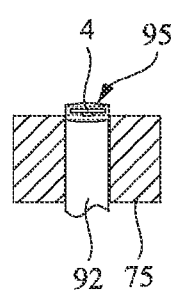
FIG. 20B is a diagram for explaining a function of a tabletting machine main body 76.
Figure 20C:
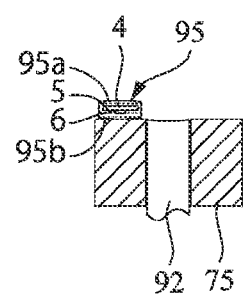
FIG. 20C is a diagram for explaining a function of a tabletting machine main body 76.
Figure 20D:
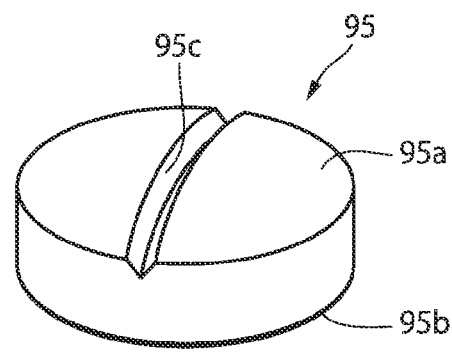
FIG. 20D is a perspective view representing a tablet for a medicine in accordance with an embodiment.

Next, upper pestle 93 is lowered, and pharmaceutical powder 90 is compressed between upper pestle 93 and lower pestle 92 (FIG. 20A). Accordingly, pharmaceutical powder 90 is solidified, so that IC chip-containing tablet 95 is manufactured (FIG. 20B). After that, lower pestle 92 is further moved upward, so that manufactured tablet 95 is discharged (FIG. 20C). In a pharmaceutical tablet 95 containing IC chip 4 equipped with an IC, tablet 95 includes a first surface 95a and a second surface 95b spaced from each other in the up/down direction. An engraved stamp or cleavage line 95c which is deeper than second surface 95b is formed in first surface 95a. IC chip 4 has base film 5 as a base plane, and a chip main body 6 as a convex portion protruding greater on one side than the other side with respect to base film 5, and chip main body 6 is arranged within tablet 95 while facing the side of second surface 95b (FIG. 20D). It is not always necessary to form an engraved stamp or a cleavage line in second surface 95b.

A tablet 95 as a medicine is often formed to have an engraved stamp or a cleavage line representing a kind or a bland name. Generally, such an engraved stamp or cleavage line 95c is formed on one or both of upper and lower sides of tablet 95. Taking into consideration the mold release characteristics from a tabletting machine at the time of manufacturing, a deeper engraved stamp/cleavage line 95c (engraved stamp/cleavage line 95c in a case where it is formed only on one side) is formed in an upper pestle. In the present embodiment, since IC chip 4 is inserted into a die of the tabletting machine in a downward manner, the convex portion in IC chip 4 faces a side opposite to a tablet surface applied with a deeper engraved stamp/cleavage line.

In first surface 95a, an engraved stamp or cleavage line 95c is formed. In second surface 95b, an engraved stamp or cleavage line is not formed, or an engraved stamp or cleavage line shallower than first surface 95a is formed. Chip main body 6 is arranged in a medical tablet while facing the side of second surface 95b. Therefore, IC chip 4 is equipped without a positional displacement. Consequently, a breakage or crack due to the positional displacement of IC chip 4 (for example, exposure of IC chip 4 to the side surface of tablet 95) can be prevented.

Further, it is preferable that a center of IC chip 4 in a thickness direction is located at a center of tablet 95 in a thickness direction. Specifically, it is preferable that a center of IC chip 4 in the thickness direction is located at an intermediate position between first surface 95a and second surface 95b.

Modified Example

Push-in portion 64 is not always necessary. Without providing push-in portion 64, IC chip 4 may be pushed out with a pusher in a state where a lower surface of main body 62 is in contact with an upper surface of rotating plate 75. In this case, the pharmaceutical powder within the die hole may be filled to an upper end of the die hole to be in a leveled state. In this case, IC chip 4 is not pushed into pharmaceutical powder 90 but is placed on pharmaceutical powder 90.

Moreover, in a case where push-in portion 64 is provided as in the above-described embodiment, push-in portion 64 may enter die hole 78 and further push in the pharmaceutical powder filled in die hole 78. Accordingly, on the surface of the pharmaceutical powder, an inner shape recess matching with an outer shape of push-in portion 64 is formed. Therefore, since IC chip 4 is set in the recess, the positional displacement due to the movement in the lateral direction can be suppressed assuredly.

Even in the case where the protrusion is provided, the protrusion is not always necessary to be formed to a lower end of positioning guide 61, and it may be omitted at the lower end. In such a case, for example, the protrusion may be formed only in the main body portion, and it may be omitted at all of or a part of the portion corresponding to the push-in portion.

It should be noted that, although positioning guide 61 including protrusion 67 in the inner circumferential surface is provided, and the pusher is pushed out in the state where IC chip 4 is set in positioning guide 61 in the above-described embodiment, the present invention is not limited to this. For example, a positioning guide without a protrusion may be used. Moreover, suction means may be used in place of the pusher, so that the IC chip suctioned by suction means is supplied so as to be pushed into the pharmaceutical powder within the die hole.

Moreover, although the IC chip is supplied to the pharmaceutical powder in a downward manner in the above-described embodiment, the IC chip may be supplied in an upward manner.

Figure 21:
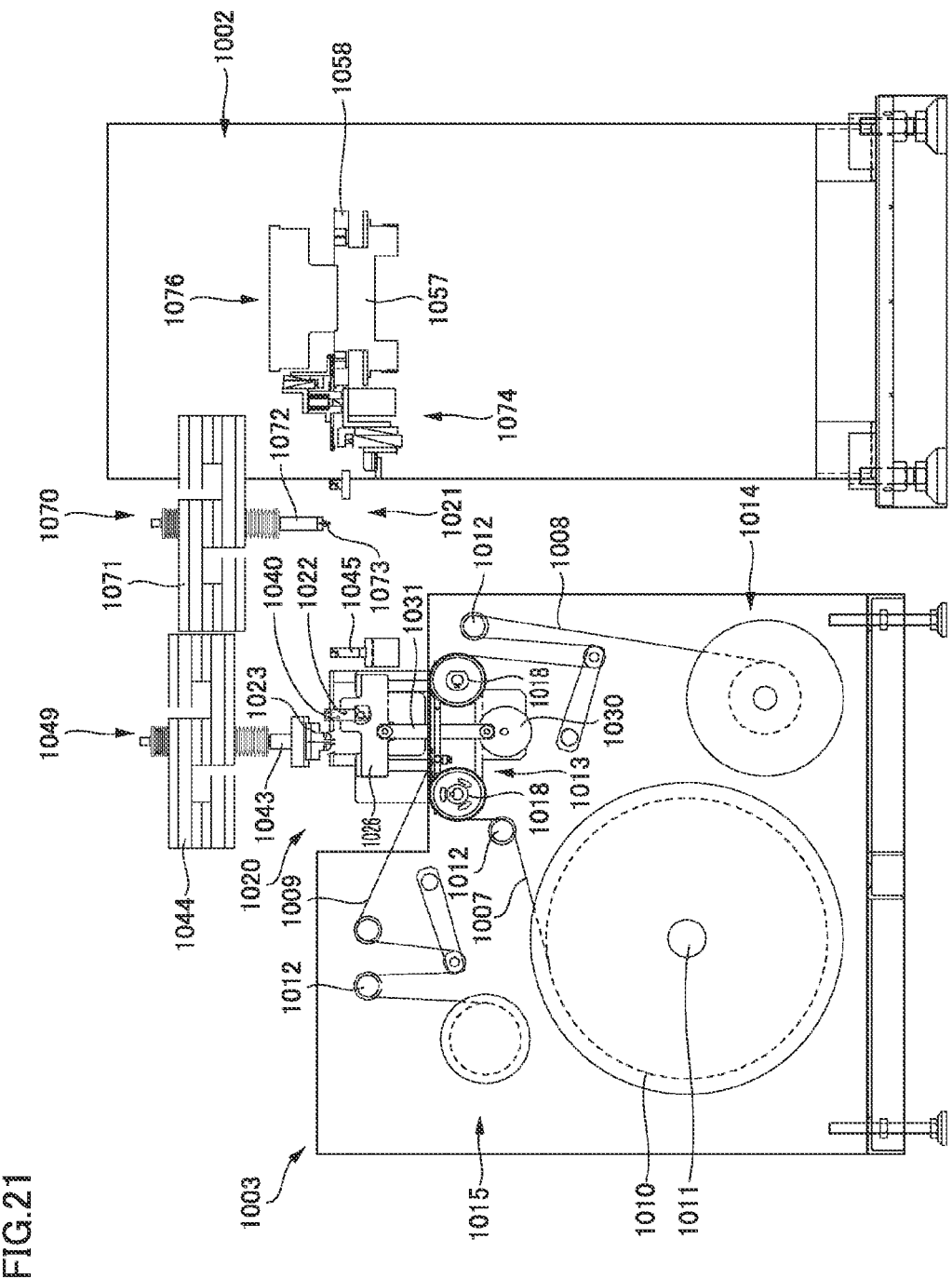
FIG. 21 is a front view representing a favorable one embodiment of a tablet manufacturing apparatus according to the present invention.
Figure 22:
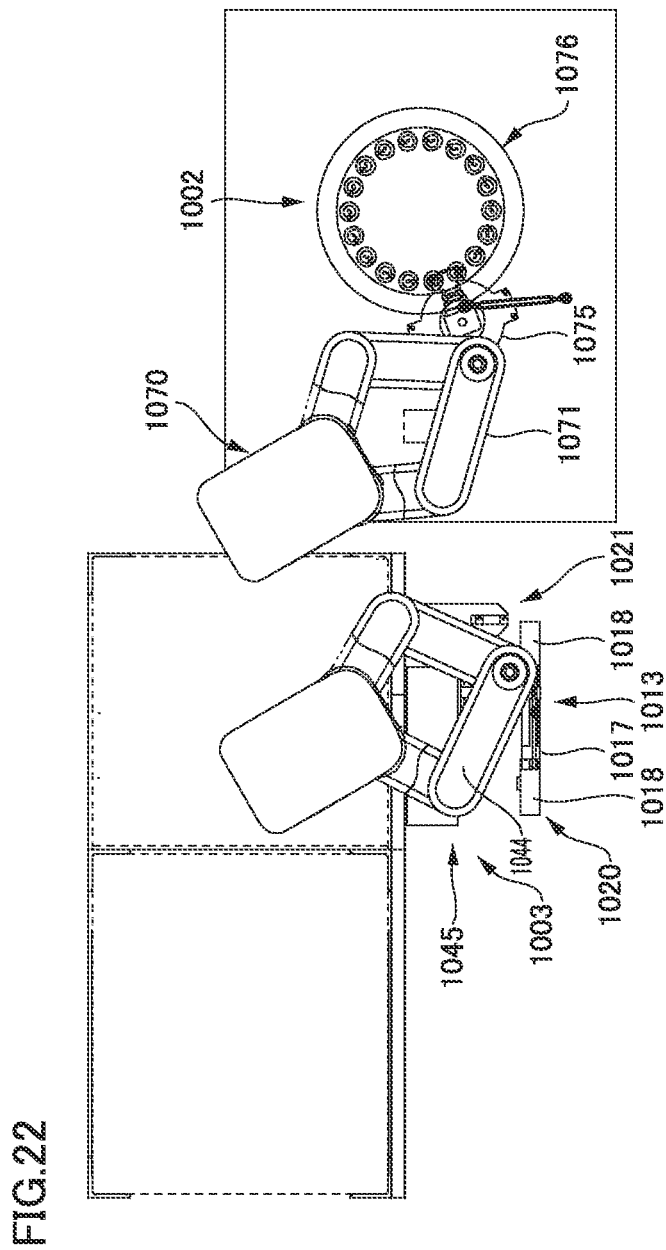
FIG. 22 is a plan view representing a favorable one embodiment of a tablet manufacturing apparatus according to the present invention.
Figure 23:
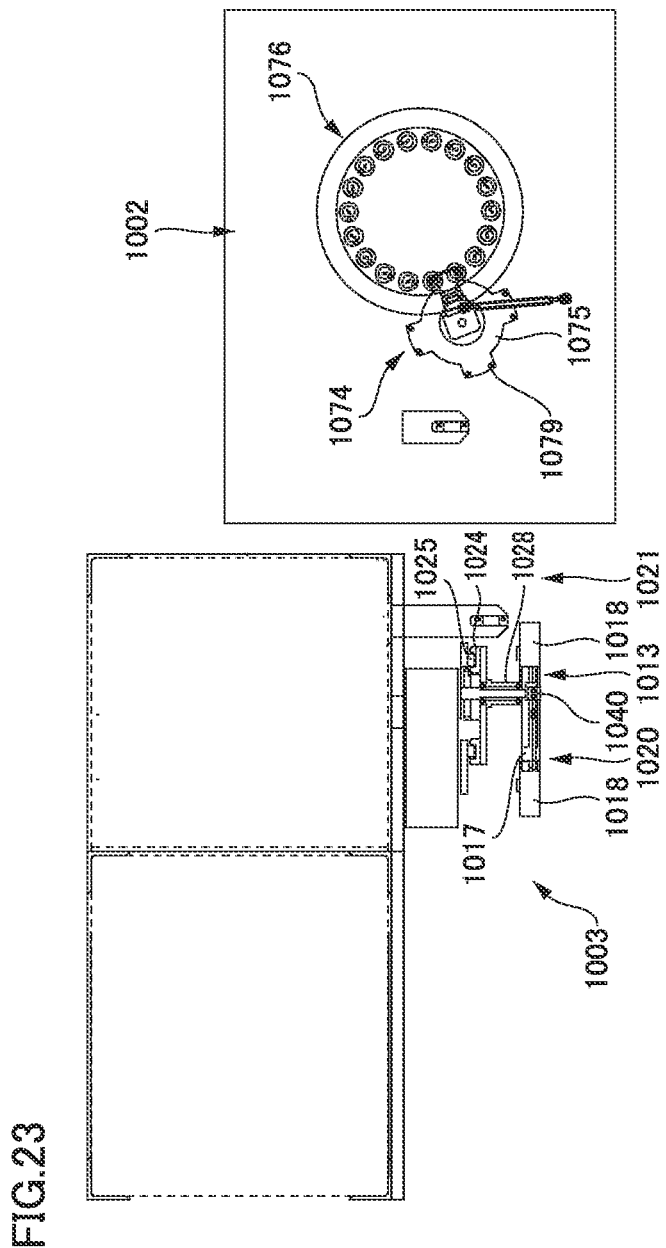
FIG. 23 is a plan view omitting illustration of a robot.
Figure 24A:
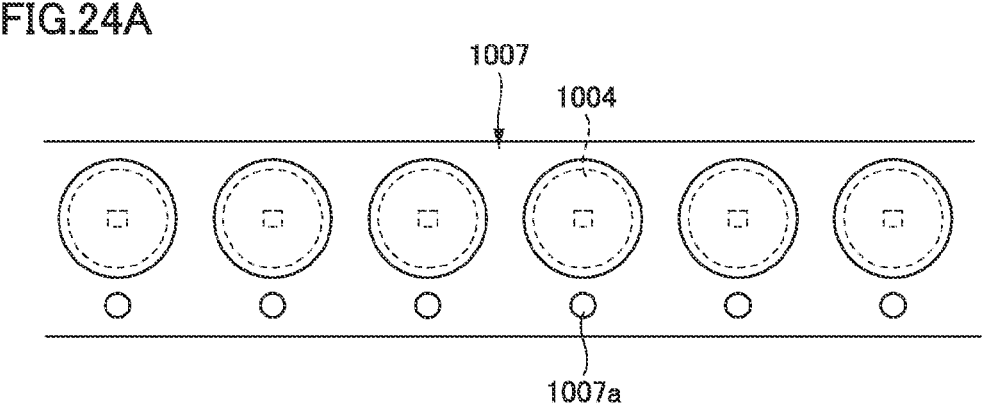
FIG. 24A is a diagram for explaining an IC chip to be supplied.
Figure 24B:
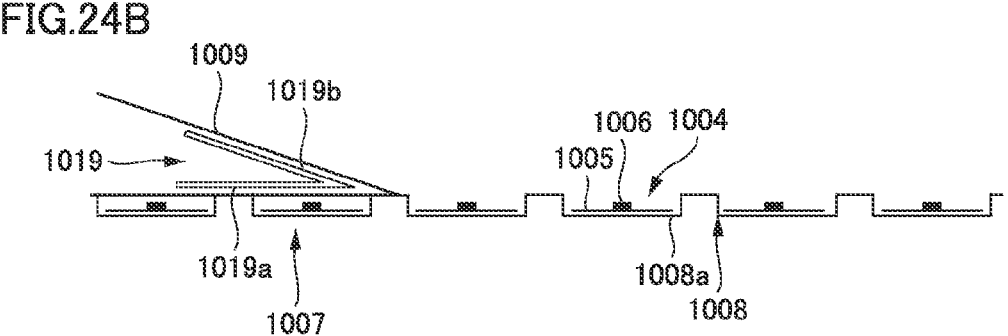
FIG. 24B is a diagram for explaining an IC chip to be supplied.
Figure 24C:
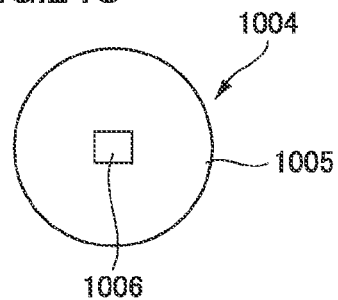
FIG. 24C is a diagram for explaining an IC chip to be supplied.

FIG. 21 is a front view representing a favorable one embodiment of a tablet manufacturing apparatus according to the present invention. FIGS. 22 and 23 are plan views thereof. FIGS. 24A to 24C are drawings for explaining an IC chip to be supplied in the present embodiment. The drawings subsequent to FIGS. 24A to 24C are enlarged views of each part of the apparatus and for explaining an effect.

As shown in FIGS. 21 to 23, a tablet manufacturing apparatus according to the present embodiment includes a tabletting machine 1002, and a supply apparatus 1003 for conveying and supplying an IC chip to tabletting machine 1002. As shown in FIGS. 24A to 24C, an IC chip 1004 which is conveyed and supplied in the present embodiment is in a form having a chip main body 1006 mounted at a center position of a circular base film 1005. Base film 1005 has, for example, a disk-like outer shape with a diameter of 3.5 mm, and includes, for example, a function for supporting chip main body 6 and an antenna function for performing transmission of information with outside. Chip main body 1006 has, for example, a rectangular outer shape of 1 mm square, and an electronic circuit is incorporated therein. Chip main body 1006 includes, for example, a storage portion for storing information specifying a tablet to which IC chip 1004 is buried, and a function for transmitting information stored in the storage portion at a predetermined timing.

As shown in FIGS. 24A and 24B, IC chips 1004 having the above-described configuration are accommodated in a belt-like accommodation tape 1007 in one line at predetermined intervals. Accommodation tape 1007 includes a carrier tape 8 having accommodation recesses 1008a formed at predetermined intervals, and a top tape 1009 covering an upper surface of carrier tape 1008. IC chips 1004 are accommodated within accommodation recesses 1008a. In FIG. 24B, as shown on the right side, top tape 1009 is peeled from carrier tape 1008, so that the upper side of accommodation recesses 1008a are opened, so that accommodated IC chips 1004 can be taken out. IC chip 1004 are accommodated in a state of being in an upward manner where chip main body 1006 is located in an upper part of accommodation recess 1008a. Further, accommodation tape 1007 has feed holes 1007a formed at equal pitch along one side edge. This accommodation tape 1007 is taken up by a supply reel 1010.

Supply apparatus 1003 includes a rotary support shaft 1011 which freely rotatably bearing-supports supply reel 1010 configured to take up on its front face the above-described accommodation tape 1007 in a rolled form, and supply reel 1010 is set on rotary support shaft 1011. Supply apparatus 1003 includes various rollers which define on their front faces conveying passages for accommodation tape 1007 or separated carrier tape 1008 and top tape 1009, an accommodation tape opening portion 1013 which allows top tape 1009 to be peeled off from carrier tape 1008 and allows IC chip 1004 accommodated in accommodation tape 1007 to be taken out, a carrier tape collecting portion 1014 which collects carrier tape 1008 from which IC chip 1004 is taken out, and a top tape collecting portion 1015 which collects top tape 1009.

Accommodation tape opening portion 1013 includes a guide plate 1017 constituting a conveying path arranged at a predetermined position on an upper side in a horizontal direction, a pair of sprockets 1018 arranged on front and back sides in the conveying direction of accommodation tape 1007 of guide plate 1017, and a peeling plate 1019 arranged at a predetermined position on an upper side of guide plate 1017.

Figure 25A:
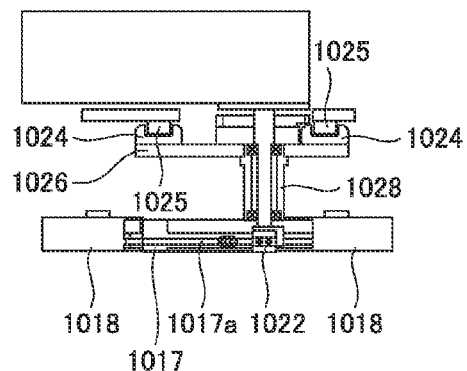
FIG. 25A is a plan view representing an accommodation tape opening portion 1013 and an IC chip take-out apparatus 1020.
Figure 25B:
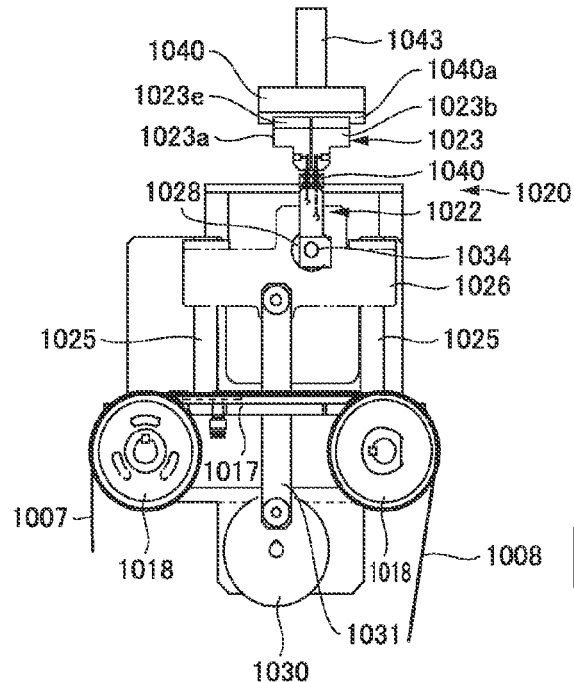
FIG. 25B is a front view representing an accommodation tape opening 1013 and an IC chip take-out apparatus 1020.
Figure 25C:
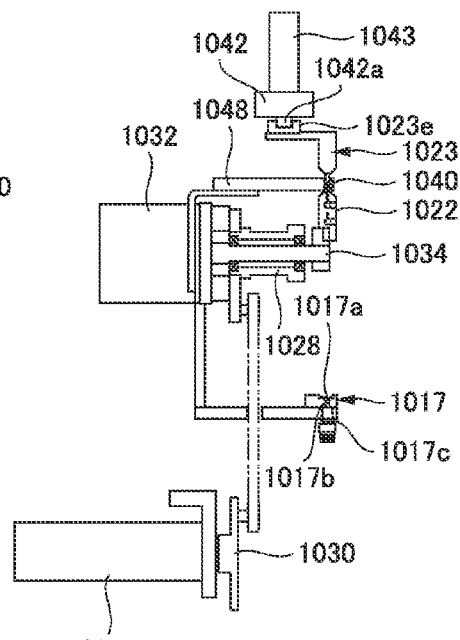
FIG. 25C is a side view representing an accommodation tape opening 1013 and an IC chip take-out apparatus 1020.

As shown in FIGS. 25A to 25C by enlargement, guide plate 1017 is provided with a recessed groove 1017a extending in an axial direction on an upper surface. A width of recessed groove 1017a is equal to or slightly larger than a tape width of accommodation tape 1007. Accordingly, accommodation tape 1007 passes through recessed groove 1017a, so that it moves forward stably without any lateral displacement. Further, as shown in FIGS. 25A to 25C and 26, in a section on an upstream side of guide plate 1017, a slit 1017b is provided in a bottom portion of recessed groove 1017a, and slit 1017b communicates with a connection pipe 1017c mounted to a lower surface of guide plate 1017. Connection pipe 1017c cooperates with an unillustrated suction pump. Accordingly, a part of the bottom portion of recessed groove 1017a at which slit 1017b is opened generates a negative pressure, so that accommodation tape 1007 can be suctioned and conveyed stably.

Moreover, sprocket 1018 has protrusions 1018a on its circumferential surface at a predetermined pitch. When accommodation tape 1007 is passed over sprockets 1018, protrusion 1018a penetrates through feed holes 1007a of accommodation tape 1007 and protrudes above tape 1007. Accordingly, when sprockets 1018 are rotated, protrusions 1018a within feed holes 1007a gives a conveying force to accommodation tape 1007, and accommodation tape 1007 follows it and moves forward by a predetermined amount, and the forward movement of accommodation tape 1004 is stopped when sprockets 1018 are stopped. Sprockets 1018 cooperates with a drive motor such as a servo motor, which is not illustrated in the drawings, for which a rotational angle can be controlled, and an intermittent driving is controlled at a predetermined timing.

As schematically shown in FIG. 24B, peeling plate 1019 includes a reference surface 1019a arranged in parallel with a conveying surface of accommodation tape 1007, and a slope surface 1019b which slopes toward a diagonally backward direction from reference surface 1019a. Accommodation tape 1007 passes through sprocket 1018 on an upstream side and thereafter passes through a location between guide plate 1017 and peeling plate 1019, and top tape 1009 is folded back from reference surface 1019a to slope surface 1019b of peeling plate 1019 and peeled off from carrier tape 1008. Accordingly, carrier tape 1008 is opened on an upper side of accommodation recess 1008a. Then, carrier tape 1008 is guided by guide plate 1017 and moves horizontally.

It should be noted that carrier tape 1008 passes through accommodation tape opening portion 1013 and thereafter passes through a predetermined passage to reach carrier tape collecting portion 1014, and then is taken up and collected by a take-up reel. Similarly, peeled top tape 1009 also passes through a predetermined passage to reach top tape collecting portion 1015, and is taken up and collected by a take-up reel.

Above accommodation tape opening portion 1013, an IC chip take-out apparatus 1020 is provided. This IC chip take-out apparatus 1020 has a function of taking out an IC chip 1004 accommodated in opened accommodation tape 1007, reversing an manner upside down, and passing IC chip 1004 to a conveying apparatus 21 in the next stage. In the present embodiment, two front and back IC chips 1004 accommodated in accommodation tape 1007 are taken out collectively. Accordingly, sprockets 1018 and the like are operated so as to intermittently convey accommodation tape 1007 at a pitch for two IC chips 1004, and is controlled to temporarily stop in a state where IC chips 1004 are located at a take-out position of IC chip take-out apparatus 1020.

Then, IC chip take-out apparatus 1020 includes a first suction and hold member 1022 for taking out IC chip 1004 accommodated in accommodation tape 1007 and reversing IC chip 1004 upside down, and a second suction and hold member 1023 for receiving IC chip 1004 taken out and reversed by first suction and hold member 1022 and supplying IC chip 1004 to conveying apparatus 1021.

First suction and hold member 1022 is formed to have two first suction nozzle portions 1022b protruding at a leading end of an elongated belt-like main body 1022a. An arrangement space of two first suction nozzle portions 1022b matches with an arrangement pitch of IC chips 1004 in accommodation tape 1007. The leading end of first suction nozzle portion 1022b is opened, and the opened part communicates with a suction passage 1022c formed within main body 1022a and first suction nozzle portion 1022b and is connected to an unillustrated suction pump.

Moreover, this first suction and hold member 1022 is configured to move upward and downward and rotate within a vertical plane. As shown in FIGS. 25A to 25C by enlargement, this first suction and hold member 1022 is bearing-supported through bearing 1028 with respect to moving plate 1026 moving upward and downward and it moves upward and downward with moving plate 1026. On a back side of moving plate 1026, sliders 1024 are attached which are movable in upward and downward directions with respect to two guide rails 1025 extending upward and downward. Moving plate 1026 is guided by guide rails 1025 and sliders 1024 and moves upward and downward stably. A drive mechanism for allowing this moving plate 1026 upward and downward is configured to couple one end of belt-like coupling plate 1031 to an eccentric position of rotating plate 1030 which receives a rotational force of drive motor 1033 to rotate, and couple the other end of coupling plate 1031 to moving plate 1026. Accordingly, rotation of rotating plate 1030 moves coupling plate 1031 and moving plate 1026 upward and downward. Then, moving plate 1026 reciprocates between a lifted position shown in FIGS. 21 and 25A to 25C and a lowered position shown in FIG. 26.

Moreover, on a back side of moving plate 1026, a drive motor 1032 is attached which is a drive source for rotating first suction and hold member 1022, and drive motor 1032 also moves upward and downward integrally with moving plate 1026. A rotational shaft 1034 cooperating with an output shaft of drive motor 1032 is mounted to bearing 1028 arranged so as to protrude on the front face side of moving plate 1026, and first suction and hold member 1022 is fixed to a leading end of rotational shaft 1034. Accordingly, rotation of drive motor 1032 also rotates first suction and hold member 1022. Then, first suction and hold member 1022 temporarily stops rotation in two manners: a passing manner in which the leading end faces upward as shown in FIGS. 21 and 25A to 25C; and a take-out manner in which the leading end faces downward as shown in FIG. 26.

Figure 26:
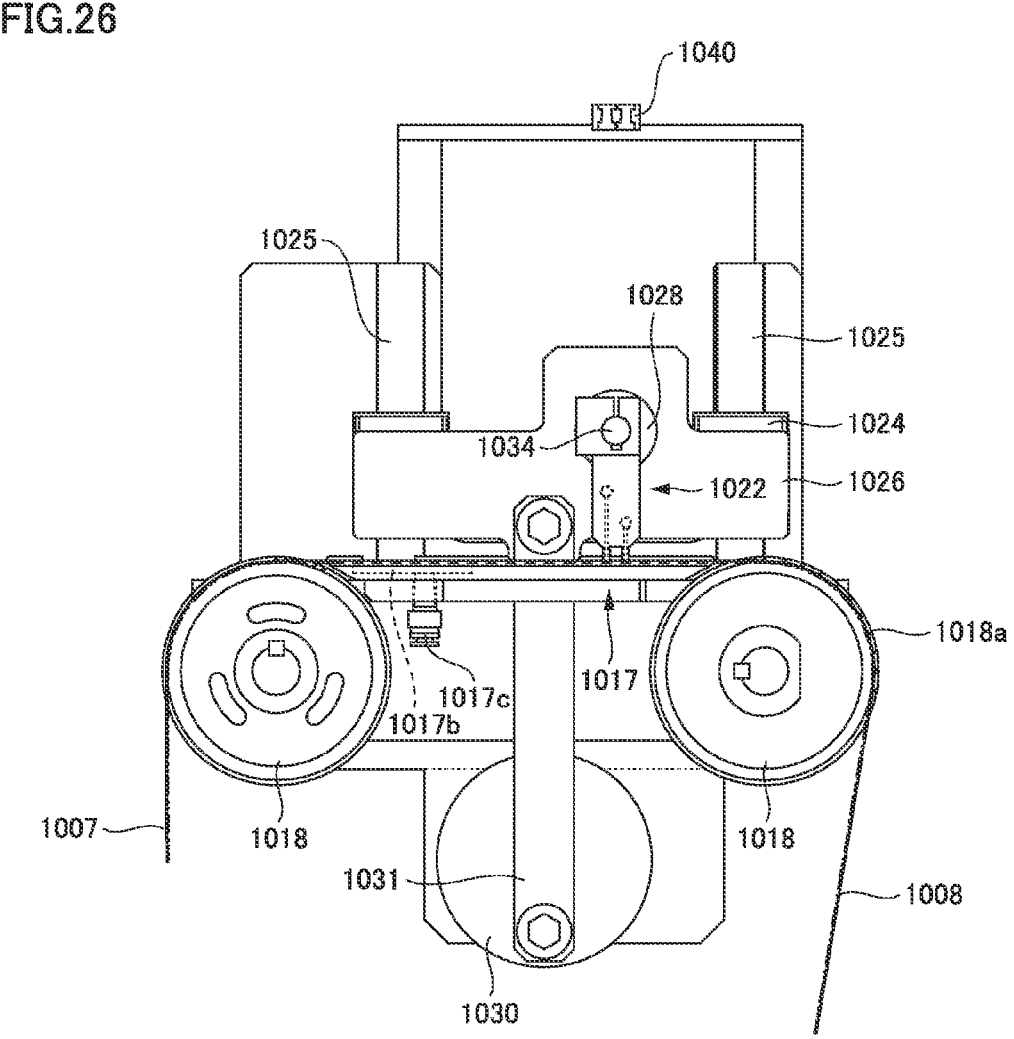
FIG. 26 is an enlarged front view representing an accommodation tape opening 1013 and an IC chip take-out apparatus 1020.
Figure 28B:
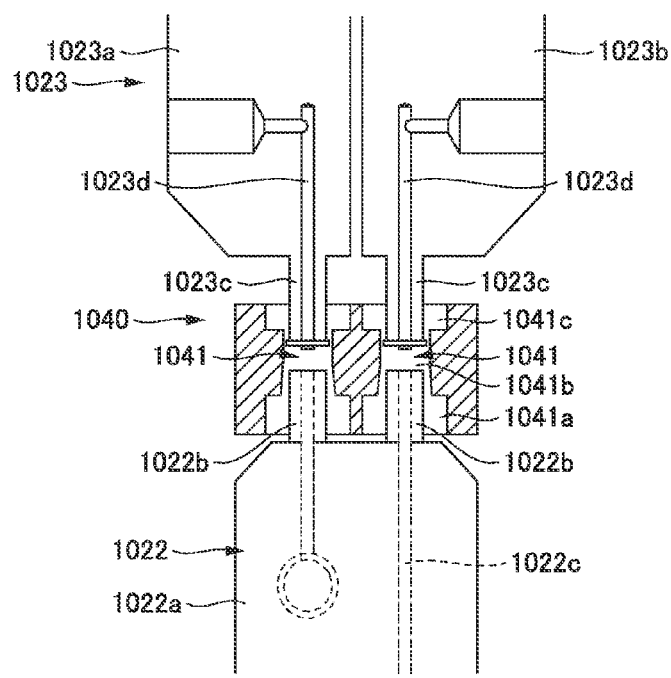
FIG. 28B is an enlarged view representing a main part of FIG. 27B.
Figure 28A:
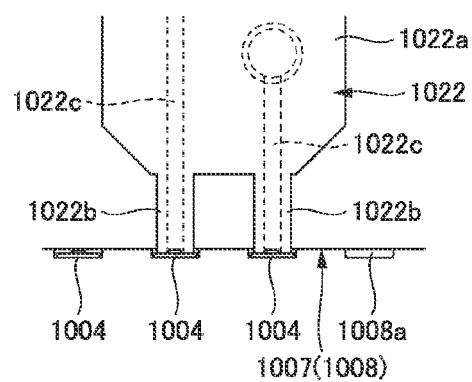
FIG. 28A is an enlarged view representing a main part of FIG. 27A.

Accordingly, when drive motors 1032, 1033 are appropriately controlled to allow first suction and hold member 1022 to be moved downward in a downward take-out manner and positioned at a lowered positioned, a leading end of first suction nozzle portion 1022b comes into contact with IC chip 1004 within accommodation tape 1007 (FIGS. 26, 27A, and 28A). When first suction nozzle portion 1022b communicates with an unillustrated suction pump in this state, suction by first suction nozzle portion 1022b is performed, so that first suction nozzle portion 1022b suctions and holds IC chip 1004.

Next, when moving plate 1026 is moved upward while maintaining first suction and hold member 1022 to be in a downward take-out manner, first suction nozzle portion 1022b of first suction and hold member 1022 is positioned above accommodation tape 1007 in a state of suctioning and holding IC chip 1004. Accordingly, taking out IC chip 1004 from accommodation tape 1007 is completed. Then, moving plate 1026 and first suction and hold member 1022 are further moved upward to reach the lifted position. Before reaching this lifted position, first suction and hold member 1022 receives driving of drive motor 1032, so that it is rotated by 180 degrees and shifted to an upward passing manner. Accordingly, IC chip 1004 suctioned by first suction nozzle portion 1022b of first suction and hold member 1022 is reversed upside down, so that chip main body 1006 takes a downward manner of being located on a lower side of base film 1005.

As shown in FIGS. 25A to 25C and 27B, a cylindrical guide (guide member) 1040 is arranged at a position where first suction nozzle portion 1022b of first suction and hold member 22 is located when first suction and hold member 1022 is at a lifted position in a passing manner of facing upward. This cylindrical guide 1040 is coupled to a machine frame through a support plate 1048 extending in a horizontal direction and is fixedly arranged at a desired position. Cylindrical guide 1040 includes two through-holes 1041 extending upward and downward. Two through-holes 1041 have parallel axis centers, and a pitch between the axes matches with an arrangement pitch of first suction nozzle portion 1022b. Moreover, each through-hole 1041 includes an inlet region 1041a at a lower end, a center region 1041b, and an outlet region 1041c at an upper end. Inner shape dimensions of inlet region 1041a and outlet region 1041c are set to be sufficiently greater than outer shape dimensions of IC chip 1004, and inner shape dimensions of center region 1041b are set to be substantially equal to or greater than outer shape dimensions of IC chip 1004. Further, the inner circumferential surface of center region 1041b is set to be a tapered shape having a narrowest center in the up/down direction. Then, when first suction and hold member 1022 moves upward while maintaining a passing manner of facing upward, first suction nozzle portion 1022b enters inlet region 1041a from a lower end of cylindrical guide 1040, and a leading end of first suction nozzle portion 1022b is positioned within center region 1041b when it reaches a lifted position. More specifically, it is positioned near a narrowest center position within center region 1041b. Accordingly, entering of IC chip 1004 suctioned and held by first suction nozzle portion 1022b into cylindrical guide 1040 passes through relatively large inlet region 1040a and moves within center region 1041b having a gradually reduced inner diameter, so that it can move to the lifted position smoothly.

On the other hand, second suction and hold member 1023 includes a first main body 1023a and second main body 1023b which come close to and separate from each other in a horizontal direction. The leading ends of first and second main bodies 1023a, 1023b respectively include second suction nozzle portions 1023c. An arrangement space of two second suction nozzle portions 1023c in a state where first main body 1023a and second main body 1023b come close to each other is set to mach with an arrangement space of first suction nozzle portion 1022b of first suction and hold member 1022. Further, the leading ends of second suction nozzle portions 1023c are opened, and the opened parts communicate with suction passages 1023d formed within first and second main bodies 1023a, 1023b and second suction nozzle portions 1023c and are connected to an unillustrated suction pump.

Moreover, this second suction and hold member 1022 is configured to move within the three-dimensional space. This movement is performed by a first robot 1049. In other words, first robot 1049 includes an arm 1044 of a SCARA robot moving within a horizontal plane, a support rod attached to a leading end lower surface of arm 1044 so as to be movable in upward and downward directions, and a base 1042 attached to the lower end of support rod 1043. The horizontal movement of arm 1044 of the SCARA robot and the upward and downward movement of support rod 1043 allows base 1042 to be moved to a desired position within a three dimensional space. Then, first main body 1023a and second main body 1023b constituting second suction and hold member 1023 are movably attached to guide rails 1042a provided at a lower surface of base 1042 through sliders 1023e. The movement of first main body 1023a and second main body 1023b is performed by, for example, a cylinder driving. Accordingly, second suction and hold member 1023 supported by base 1042 and its lower surface move within the three dimensional space. Further, first main body 1023a and second main body 1023b come close to and separate from each other along guide rails 1042a.

Specifically, second suction and hold member 1023 follows the operation of arm 1044 of the SCARA robot and moves to a position overlapping with cylindrical guide 1040 in the horizontal plane, and support rod 1043 is lowered while maintaining that state, so that second suction and hold member 1023 reaches a lowered position. At this time, first main body 1023a and second main body 1023b are set to come close to each other. In this state, as shown in FIGS. 25A to 25C, 27B, and 28B, second suction nozzle portions 1023c enter outlet region 1041c from an upper end of cylindrical guide 1040. Then, after having reached a lowest end position, the leading ends of the second suction nozzles 1023c are positioned within center region 1041b. In this state, a control is performed to come close to a leading end of first suction nozzle portion 1022b of first suction and hold member 1022 located at the lifted position with a certain clearance (for example, 0.5 mm).

Accordingly, IC chip 1004 suctioned and held by first suction nozzle portion 1022b waits in a state of being located in center region 1041b of through-hole 1040 of cylindrical guide 1040, and lower ends of second suction nozzle portions 1023c of second suction and hold members 1023 having entered the cylindrical guide 1030 from above comes into contact with or close to IC chip 1004. Then, suction by second suction nozzle portion 1023c is started and suction by first suction nozzle portion 1022b is stopped at an appropriate timing, so that suctioning and holding of IC chip 1004 is shifted to the side of second suction and hold member 1023.

As can be seen, the present embodiment is characterized in performing the transfer of IC chip 1004 from first suction and hold member 1022 to second suction and hold member 1023 within cylindrical guide 1040. Since IC chip 1004 has a small diameter of, for example, 3.5 mm, and has a thin shape of base film 1005, it cannot be firmly held by a suction and hold member. Therefore, if the passing from first suction and hold member 1022 to second suction and hold member 1023 is performed in a state where IC chip 1004 is exposed, IC chip 1004 is displaced when suction by first and second suction nozzle portion 1022b, 1023b is switched. Accordingly, the passing cannot be performed smoothly, and IC chip 1004 may be dropped. However, according to the present embodiment, since the passing process is performed inside of cylindrical guide 1040, passing can be performed assuredly.

After that, first suction and hold member 1022 moves downward while maintaining the passing manner. When first suction nozzle portion 1022b goes out of cylindrical guide 1040, first suction and hold member 1022 rotates by 180 degrees and returns to a lowered position at an appropriate timing, and prepares for next operation of taking out the IC chip. On the other hand, second suction and hold member 1023 having received IC chip 1004 moves upward along with lifting of support rod 1043, and second suction nozzle portion 1024 is located above cylindrical guide 1040. After that, by the operation of arm 1044 of the SCARA robot, second suction and hold member 1023 moves in a horizontal direction and reaches a conveying-in position of conveying apparatus 1021.

Figures 30A, 30B:
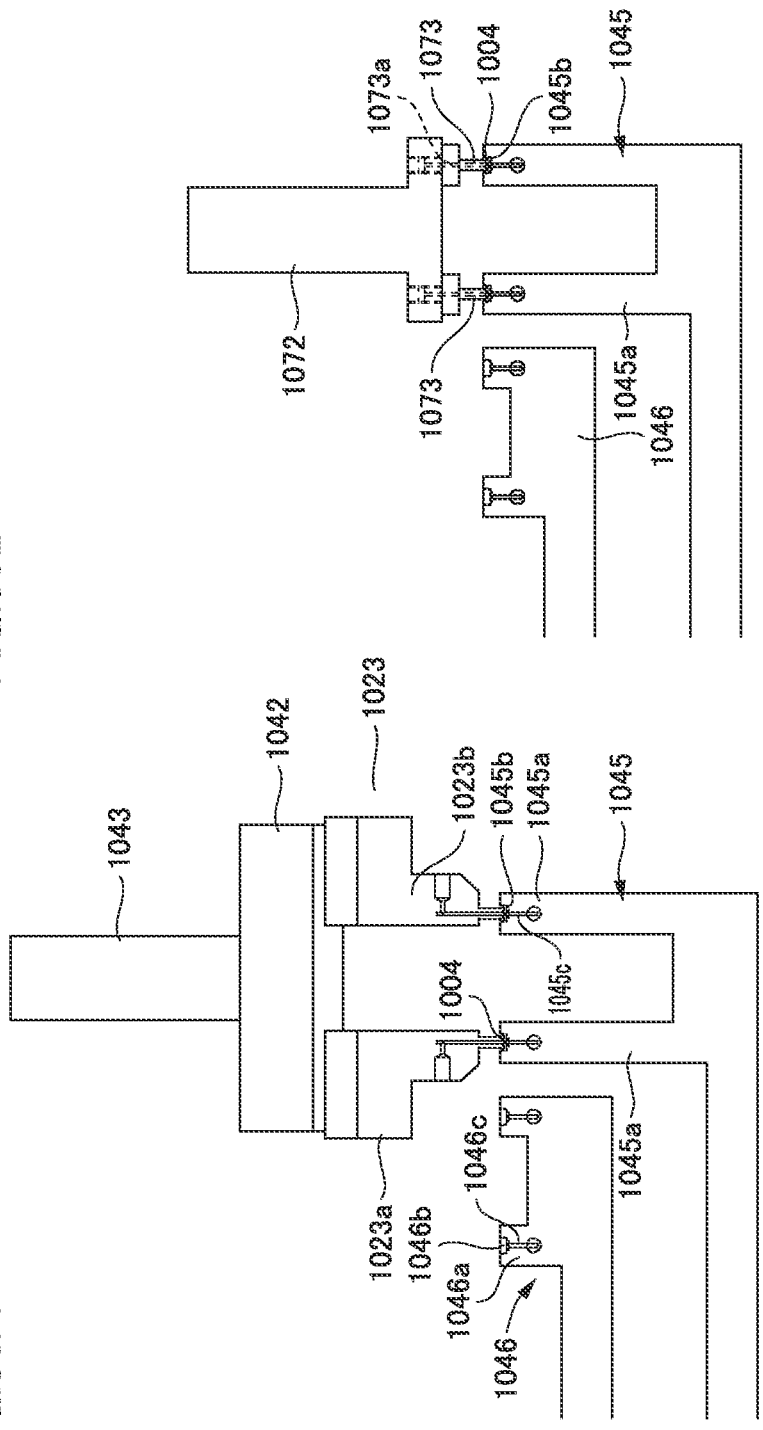
FIG. 30A is a diagram for explaining passing of an IC chip from a second suction and hold member to a conveying apparatus.
FIG. 30B is a diagram for explaining passing of an IC chip from a conveying apparatus to a third suction nozzle portion.

As shown in FIGS. 29A and 29B, conveying apparatus 1021 includes a first receiving portion 1045 and a second receiving portion 1046 for receiving two IC chips 1004 suctioned, held, and conveyed by second suction and hold member 1023, and a drive mechanism 1047 for allowing these first receiving portion 1045 and second receiving portion 1046 to move forward and backward. As shown in FIGS. 30A and 30B by enlargement, first receiving portion 1045 includes recesses 1045b for accommodating IC chips 1004 in upper surfaces of two pillar portions 1045a facing upward and separated into two legs. A space between pillar portions 1045a (recesses 1045b) is in conformity with the tabletting machine in the next stage, and is set to be longer than an arrangement pitch of IC chips 1004 in accommodation tape 1007 (an arrangement interval of first suction nozzle portion 1022b and second suction and hold member 1023). Moreover, a bottom surface of recess 1045b communicates with a suction passage 1045c formed within pillar portion 1045a and is connected to an unillustrated suction pump. Accordingly, IC chip 1004 set within recess 1045b is suctioned and held within recess 1045b. Even when first receiving portion 1045 moves forward, IC chip 1004 moves forward with first receiving portion 1045 while being set within recess 1045b.

Similarly, second receiving portion 1046 includes recesses 1046b for accommodating IC chips 1004 on an upper surface of two pillar portions 1046a separated to be two legs facing upward. A space of pillar portions 1046a (recesses 1046b) is in conformity with the tabletting machine in the next stage and set to be longer than an arrangement pitch of IC chips 1004 in accommodation tape 1007 (an arrangement space of first suction nozzle portion 1022b and second suction and hold member 1023). Moreover, the bottom surface of recess 1046b communicates with a suction passage 1046c formed within pillar portion 1046a and is connected to an unillustrated suction pump. Accordingly, IC chip 1004 set within recess 1046b is suctioned and held by recess 1046b. Even when second receiving portion 1046 moves forward, IC chip 1004 moves forward with second receiving portion 1046 while being set within recess 1046b.

Drive mechanism 1047 for first receiving portion 1045 and second receiving portion 1046 includes a drive motor 1050, and a rack 1051 and a pinion 1052 which receive an output of drive motor 1050 and converts it into a reciprocating linear motion. First receiving portion 1045 and second receiving portion 1046 cooperate with rack 1051 through respective coupling plates 1053, 1054 and move in reverse directions. In other words, when first receiving portion 1045 moves forward, second receiving portion 1046 moves backward. When first receiving portion 1045 moves forward, second receiving portion 1046 moves backward. For example, when first receiving portion 1045 is at a conveying-in position, second receiving portion 1046 is at a conveying-out position. Moreover, for example, when first receiving portion 1045 is at a conveying-out position, second receiving portion 1046 is at a conveying-in position. Moreover, sliders 1055 are coupled to a lower surface of coupling plate 1053 and an upper surface of coupling plate 1054. Sliders 1055 are mounted respectively to corresponding guide rails 1056, and guides forward and backward movement of rack 1051 and each receiving portion 1045, 1046 with the rotation of pinion 1052.

Second suction and hold member 1023 having received IC chip 1004 moves within a horizontal plane by arm 1044 of the SCARA robot, and is positioned above first receiving portion 1045 or second receiving portion 1046 located at the conveying-in position. As described above, since first receiving portion 1045 and second receiving portion 1046 move forward and backward in directions opposite to each other, first robot 1049 controls an operation of arm 1044 of the SCARA robot, and allows second suction and hold member 1023 to be alternately positioned above the conveying-in position of first receiving portion 1045 and above the conveying-in position of second receiving portion 1046.

As described above, since a space between pillar portions 1045a (recesses 1045b) of first receiving portion 1045 and a space between pillar portions 1046a (recesses 1046b) of second receiving portion 1046 are set to be wide, first robot 1049 controls first main body 1023a and second main body 1023b of second suction and hold member 1023 to be separated apart to widen the space of second suction nozzle portion 1023c during the horizontal movement of second suction and hold member 1023 by arm 1044 of the SCARA robot or at the time of being positioned above the conveying-in position. This widened space of second suction nozzle 1023c is set to be equal to the space of recesses 1045b, 1046b.

Then, when support rod 1043 is moved downward in a state where first main body 1023*a* and second main body 1023*b* are separated apart, for example, as shown in FIG. 30A, the lower end of second suction nozzle portion 1023*c* of second suction and hold member 1023 enters recess 1045*b* of first receiving portion 1045, so that IC chip 1004 suctioned and held in a downward manner is set within recess 1045*b*. The, when the suction on the side of second suction and hold member 1023 is released at an appropriate timing, IC chip 1004 is transferred to recess 1045*b* of first receiving portion 1045. Moreover, first receiving portion 1045 starts the suction in advance or at an appropriate timing, and suctions and holds IC chip 1004 within recess 1045*b*.

Second suction and hold member 1023 having completed a supply of IC chip 1004 to first receiving portion 1045 in such a manner returns to a passing position within cylindrical guide 1040 by the operation of first robot 1049 and supplies a next passed IC chip to recess 1046*b* of second receiving portion 1046.

On the other hand, first receiving portion 1045 having received a supply of IC chip 1004 moves forward and is positioned at a conveying-out position. IC chip 1004 within recess 1045*b* of first receiving portion 1045 having reached the conveying-out position is suctioned and held by second robot 1070 and transferred to tabletting machine 1002. Second robot 1070 includes an arm 1071 of the SCARA robot moving within the horizontal plane, a support member 1072 attached movably upward and downward on the leading end lower surface of arm 1071, and a pair of third suction nozzle portion 1073 attached to a lower end of support member 1072. A leading end of third suction nozzle portion 1073 is opened, and the opened part communicates with suction passage 1073*a* formed within third suction nozzle portion 1073 and is connected to an unillustrated suction pump. Then, by the horizontal movement of arm 1071 of the SCARA robot, and the upward and downward movement of support member 1072, third suction nozzle portion 1073 can move to a desired position within the three dimensional space. Further, a space of the pair of third suction nozzle portion 1073 matches with an arrangement space of pillar portions 1045*a* (recesses 1045*b*) of first receiving portion 1045 and pillar portions 1046*a* (recesses 1046*b*) of second receiving portion 1046.

Therefore, the suction by means of the suction pump is performed in a state where a lower end of third suction nozzle portion 1073 reaches recess 1045*b* of first receiving portion 1045 or recess 1046*b* of second receiving portion at the conveying-out position by the operation of second robot 1070. When the suction by the vacuum pump on the side of first receiving portion 1045 or second receiving portion 1046 is released, IC chip 1004 is suctioned and held on the side of third suction nozzle portion 1073 (refer to FIG. 30B).

Figure 31A:
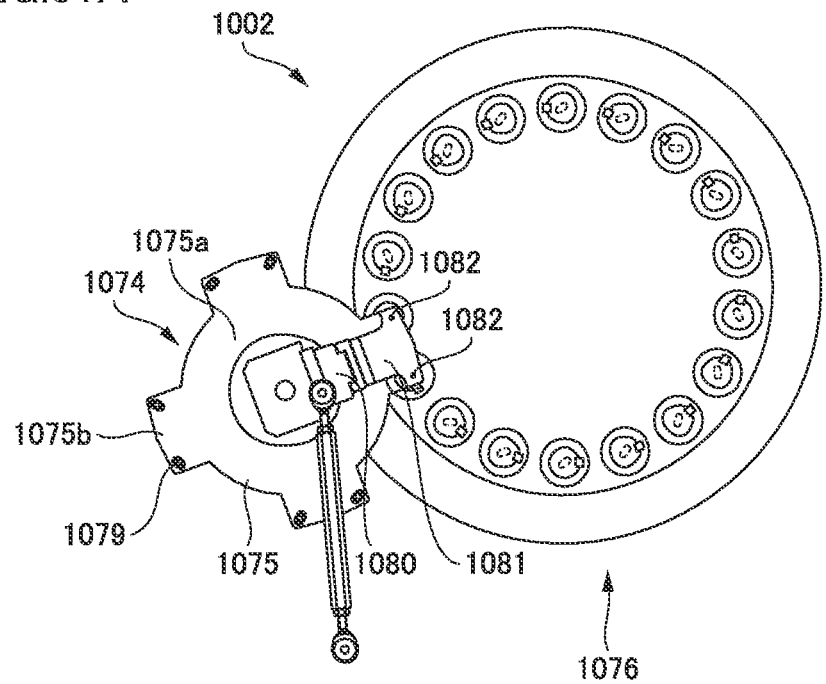
FIG. 31A is a plan view representing a tabletting machine.
Figure 31B:
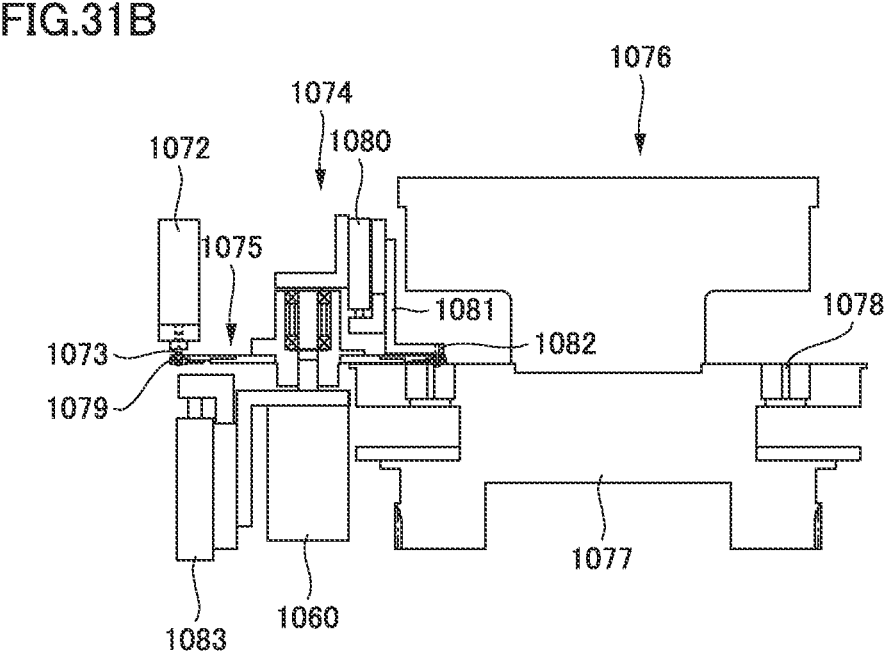
FIG. 31B is a front view representing a tabletting machine.

Next, by the operation of second robot 1070, third suction nozzle portion 1073 suctioning and holding IC chip 1004 performs the upward movement, the horizontal movement, and the descending movement, so that, as shown in FIGS. 22 and 31B, it is positioned within IC chip receiving portion 1079 of rotary table 1075 of IC chip supply apparatus 1074 arranged on the conveying-in side of tabletting machine 1002. When the suction by third suction nozzle portion 1073 is released in this state, IC chip 1004 is supplied into IC chip receiving portion 1079.

Tabletting machine 1002 includes IC chip supply apparatus 1074 and tabletting machine main body 1076 described above. Tabletting machine main body 1076 is similar to the conventionally existing tabletting machine, and it fills pharmaceutical powder into a plurality of die holes 1078 provided at predetermined intervals on a circumference along the outer edge portion of rotating plate 1077 and compresses and shapes the filled pharmaceutical powder by means of a lower pestle and an upper pestle to manufacture a tablet. In the present embodiment, in order to manufacture an IC chip-containing tablet, a function of firstly supplying IC chip 1004 by means of IC chip supply apparatus 1074 onto a predetermined amount pharmaceutical powder supplied to die hole 1078, further filling pharmaceutical powder onto IC chip 1004, and thereafter compressing and shaping these pharmaceutical powder and IC chip from above and below. Details of the manufacturing processes for tablets will be described later.

IC chip supply apparatus 1074 as a main part of the present invention includes rotary table 1075 described above, and aligns and supplies IC chip 1004 supplied to rotary table 1075 within die hole 1078 of tabletting machine main body 1076. Rotary table 1075 is rotated by a rotational force received from drive motor 1060. In the present embodiment, it is controlled to rotate intermittently at 90 degrees intervals. Moreover, rotary table 1075 includes protruding parts 1075*b* protruding outward at 90 degrees intervals on an outer circumference of plate-like main body 1075*a*. IC chip receiving portion 1079 is provided at protruding parts 1075*b*. From the side of supply apparatus 1003, IC chips 1004 are supplied in two-pieces unit. Therefore, two IC chip receiving portions 1079 are provided for each protruding part 1075*b*. In the present embodiment, a position rotated by 180 degrees from the IC chip receiving position from supply apparatus 1003 on an upstream side is set to be a supplying position of IC chip 1004 to tabletting machine main body 1076. Then, it is temporarily stopped at a position rotated by 90 degrees from the IC chip receiving position. At this time, it is favorable to provide, for example, an inspection apparatus for performing an inspection on whether or not the IC ship is correctly supplied to IC chip receiving portion 1059.

Figure 32:
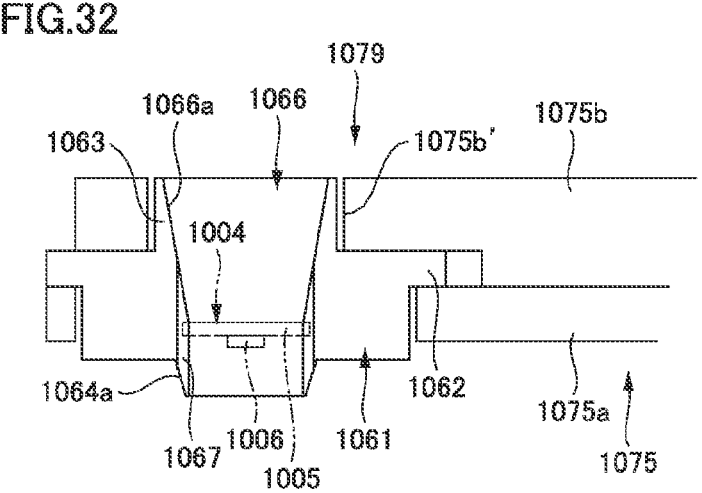
FIG. 32 is an enlarged view representing a main part of an IC chip supply apparatus 1074.
Figure 33A:
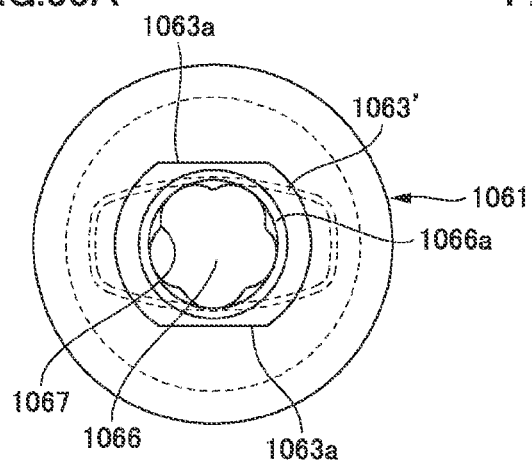
FIG. 33A is a plan view representing a positioning guide 1061.
Figure 33C:
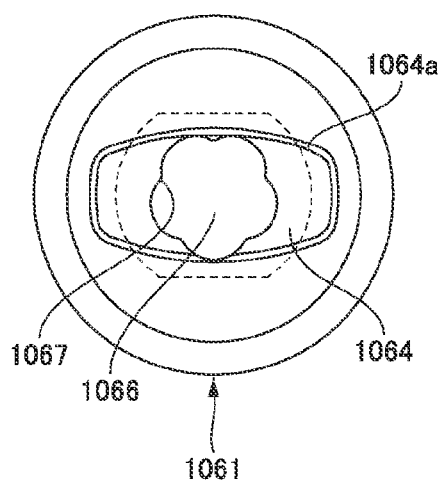
FIG. 33C is a bottom view representing a positioning guide 1061.
Figure 33B:
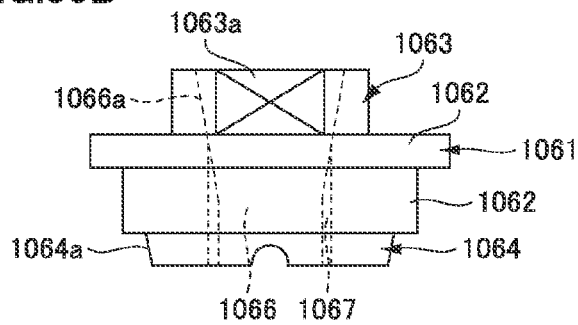
FIG. 33B is a front view representing a positioning guide 1061.

As shown in FIG. 32 by enlargement, a through-hole 1075*b*' penetrating up and down is provided at a specified position of protruding part 1075 of rotary table 1075, and a positioning guide 1061 is mounted to through-hole 1075*b*'. This positioning guide 1061 constitutes IC chip receiving portion 1059. Positioning guide 1061 has a basic shape of a ring shape having a through hole penetrating up and down as also shown in FIGS. 33A to 33C.

Positioning guide 1061 includes a flange portion radially protruding on an outer circumference of an upper circumferential side surface of a cylindrical main body 1062, and a convex portion 1063 protruding upward is provided at a center of an upper surface of main body 1062. Convex portion 1063 includes a flat surface 1063*a* on its side surface. Convex portion 1063 is inserted to through-hole 1075*b*' of protruding part 1075*b*, and flange portion 1063 is sandwiched and held by protruding part 1075*b* and main body 1075*a*. Accordingly, a movement in an axial direction, in other words, an up/down direction of positioning guide 1061 is prevented, so that separation of positioning guide 1061 from rotary table 1075 is prevented. Further, an inner circumferential surface shape of through-hole 1075*b*' of protruding part 1075*b* is set to substantially match with an outer peripheral surface shape of convex portion 1063 of positioning guide 1061. Accordingly, rotation about an axis of positioning guide 1061 is prevented. Therefore, positioning guide 1061 is held at rotary table 1075 at a correct location and in a correct manner.

A through-hole 1066 provided in positioning guide 1061 has a tapered surface 1066*a* in which a cross section of an upper region is circular and has a diameter gradually increasing as it goes upward. This upper region is a region in which convex portion 1063 is mainly formed. An inner diameter of through-hole 1066 at an upper end of convex portion 1063 is set to be larger than an outer diameter of IC chip 1004, and IC chip 1004 suctioned and held by third suction nozzle portion 1073 enters through-hole 1066 of positioning guide 1061 in accordance with the lowering of third suction nozzle portion 1073. The entering is guided by tapered surface 1066*a* to prompt a smooth downward movement.

Moreover, an inner circumferential surface in a portion of main body 1062 of through-hole 1066 is provided with a plurality of protrusions 1067 protruding toward a center. In the present embodiment, five protrusions 1067 are provided. However, the number may be, for example, three, or any other number may be used. A leading end position of protrusion 1067 is positioned on an imaginary circumference being concentric with through-hole 1066 and having a predetermined diameter. This predetermined diameter is set to be equal to or slightly smaller than a diameter of IC chip 1004. Accordingly, a peripheral edge of IC chip 1004 inserted to through-hole 1066 of positioning guide 1061 is supported by protrusions 1067, and IC chip 1004 is held in a state where a center of IC chip 1004 and a center of positioning guide 1061 (through-hole 1066) are matched. Therefore, positioning is performed with a high accuracy. Moreover, it is preferable to manufacture positioning guide 1061 with an elastic body such as rubber since it holds IC chip 1004 more firmly. Furthermore, protrusions 1067 are preferably arranged at equal intervals in the circumferential direction. It is preferable since IC chip 1004 is evenly supported.

Further, in the present embodiment, a push-in portion 1064 protruding downward is provided on a lower surface of main body 1062. A planar shape of this push-in portion 1064 is set to be substantially elliptical as shown in FIG. 33C. In this example, it has a shape of being collapsed flatly on both ends of a large-diameter side of the elliptical shape. The planar shape of push-in portion 1064 is based on a shape of a tablet to be manufactured, and is slightly smaller than that shape. In other words, it has a shape which is slightly smaller than a cross-sectional shape of die hole 1078 formed in tabletting machine main body 1076. Moreover, push-in portion 1064 has a tapered shape 1064*a* having a peripheral surface becoming smaller as it goes downward. Further, in the present embodiment, protrusions 1067 formed on an inner circumferential surface of through-hole 1066 is formed to a lower end of this push-in portion 1064.

Figure 34A:
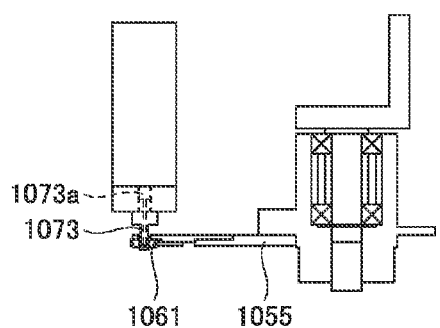
FIG. 34A is a drawing for explaining an operation of an IC chip supply apparatus 1074.
Figure 35A:
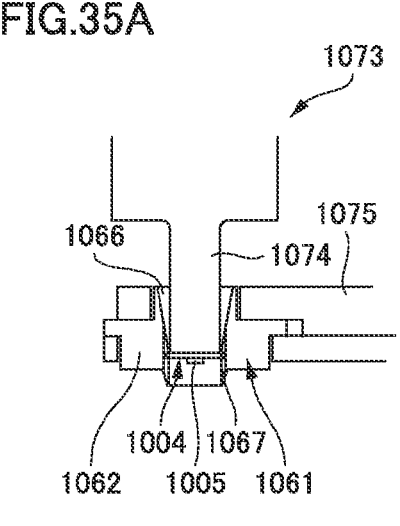
FIG. 35A is an enlarged view representing a main part of FIG. 34A.

Next, a supply of IC chip 1004 from supply apparatus 1003 to IC chip supply apparatus 1074 and an operation of supplying IC chip 1004 to tabletting machine 1002 will be described, and a configuration of IC chip supply apparatus 1074 will be described. FIGS. 34A and 35A represents a state in which a leading end of third suction nozzle portion 1073 of supply apparatus 1003 is inserted into positioning guide 1061 constituting IC chip receiving portion 1059. As shown in the drawings, second suction and hold member 1023 moves downward, and a leading end of third suction nozzle portion 1073 suctioning and holding IC chip 1004 enters through-hole 1066 of positioning guide 1061, and stops at an appropriate position of main body 1062. At this appropriate position, IC chip 1004 is supported by protrusions 1067. Since the suction by third suction nozzle portion 1073 is performed until reaching this stopping position, IC chip 1004 moves downward while maintaining a horizontal state in a downward manner in which chip main body 1006 is positioned below. At the lower stopping position of third suction nozzle portion 1073, IC chip 1004 comes into contact with the plurality of protrusions 1067 in a horizontal manner.

Next, the suction by third suction nozzle portion 1073 is released, and third suction nozzle portion 1073 moves upward, separates apart from positioning guide 1061, and proceeds to take next IC chip. On the other hand, IC chip 1004 in a downward manner remaining in positioning guide 1061 is supported in a state of maintaining a horizontal manner by protrusions 1067 of positioning guide 1061. Moreover, the above-described positioning of IC chip 1004 at a center is performed with a high accuracy.

Figure 34B:
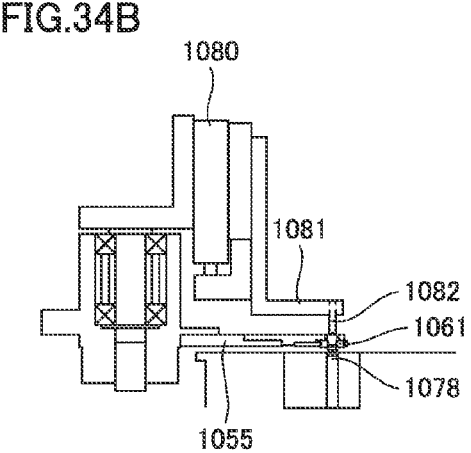
FIG. 34B is a diagram for explaining an operation of an IC chip supply apparatus 1074.
Figure 35B:
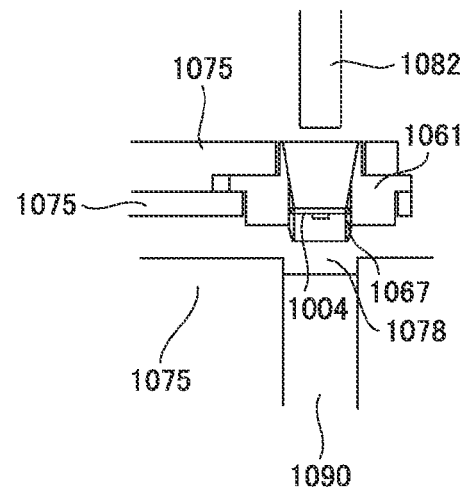
FIG. 35B is an enlarged view representing a main part of FIG. 34B.

The drawings subsequent to FIGS. 34B and 35B represent a supply position to tabletting machine 1002 with rotary table 1075 rotated by 180 degrees from the state of FIGS. 34A and 35A. At this supply position, two pushers 1082 are suspended on the leading end lower surface of an L-shaped plate 1081 which receives driving of first cylinder 1080 and moves upward and downward. Two pushers 1082 are in conformity with an arrangement pitch of two positioning guides 1061 adjacent to each other in a circumferential direction, and are adjusted so that an axis center of each positioning guide 1061 and an axis center of pusher 1082 matches at the time when the rotary table is temporarily stopped.

Further, first cylinder 1080, L-shaped plate 1081, pushers 1082, and rotary table 1075 can be lifted and lowered integrally. Then, the lifting and lowering operation is performed by receiving driving of second cylinder 1083.

Therefore, positions of rotary table 1075 and pushers 1082 can be switched by appropriately switching the reciprocating operation of first cylinder 1080 and second cylinder 1083. For example, FIGS. 34B and 35B represent a state in which first cylinder 1080, L-shaped plate 1081, pushers 1082, and rotary table 1075 are positioned at a lifted position by second cylinder 1083, and pushers 1082 are also positioned at a lifted position by first cylinder 1080. In this state, rotary table 1075 is separated apart from an upper surface of rotating table 1077 of tabletting machine main body 1076, and positioning guide 1061 is also separated apart from an upper surface of rotating plate 1077. Moreover, a lower surface of pusher 1082 is positioned above positioning guide 1061, and pushers 1082 and IC chip 1004 supported by positioning guide 1061 in a downward manner are in a non-contact state. This state is an initial state when rotary table 1075 is rotated to reach a supplying position and temporarily stopped.

Figure 34C:
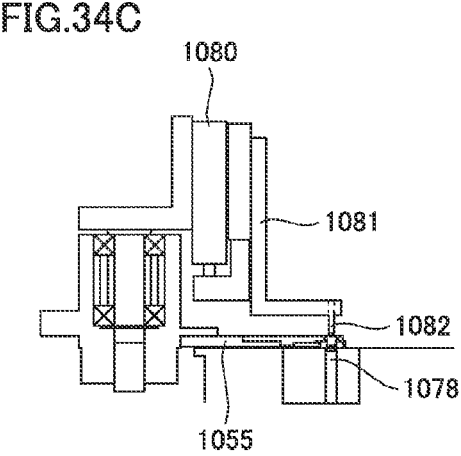
FIG. 34C is a diagram for explaining an operation of an IC chip supply apparatus 1074.
Figure 35C:
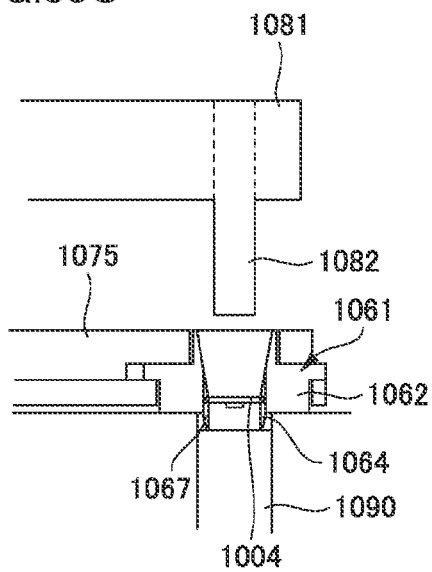
FIG. 35C is an enlarged view representing a main part of FIG. 34C.

Next, only second cylinder 1083 is operated to position first cylinder 1080, L-shaped plate 1081, pushers 1082, and rotary table 1075 at a lowered position. Accordingly, as shown in FIGS. 34C and 35C, rotary table 1075 comes close to an upper surface of rotating plate 1077 of tabletting machine main body 1076, and a lower surface of main body 1062 of positioning guide 1061 comes into contact with an upper surface of rotating plate 1077. Further, push-in portion 1064 enters die hole 1078, and comes into contact with pharmaceutical powder filled in die hole 1078. Moreover, at this time, since first cylinder 1080 remains in the initial state, a relative positional relationship between pusher 1082 and positioning guide 1061 does not change, and a lower surface of pusher 1082 is positioned above positioning guide 1061, and pushers 1082 and IC chip 1004 in a downward manner supported by positioning guide 1061 are in a non-contact state.

Figure 34D:
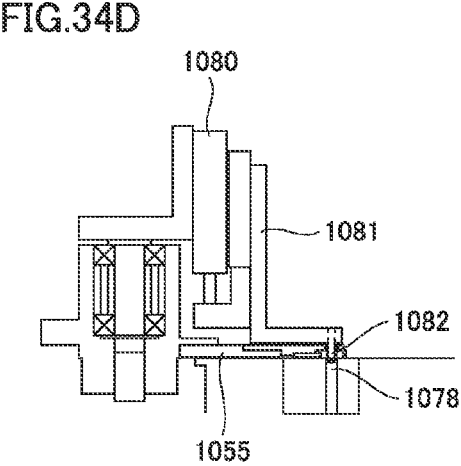
FIG. 34D is a diagram for explaining an operation of an IC chip supply apparatus 1074.
Figure 35D:
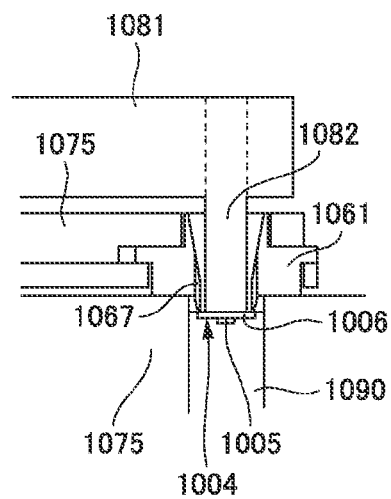
FIG. 35D is an enlarged view representing a main part of FIG. 34D.

After that, while second cylinder 1083 maintains the above-described state, first cylinder 1080 is operated, and pushers 1082 are moved downward. Accordingly, as shown in FIGS. 34D and 35D, a lower end of pusher 1082 reaches a lower end of positioning guide 1061, in other words, to a lower end of push-in portion 1064, and IC chip 1004 is forced downward by pusher 1082, pushed out from positioning guide 1061, and pushed into pharmaceutical powder 1090. Also during the downward movement of IC chip 1004 by pusher 1082, IC chip 1004 moves while maintaining a horizontal state and a center position by means of protrusions 1067 of positioning guide 1061. Therefore, when IC chip 1004 is pushed out from positioning guide 1061 and finally pushed into and supplied to pharmaceutical powder 1090, it is supplied with a high accuracy to a center of a surface of pharmaceutical powder 1090 filled in die hole 1078. Moreover, since IC chip 1004 is pushed by pusher 1082 into pharmaceutical powder 1090 before being compressed by tabletting machine main body, a positional displacement is suppressed.

Further, since IC chip 1004 is pushed into pharmaceutical powder 1090 in a downward manner in which chip main body 1006 is positioned below, chip main body 1006 is further inserted into pharmaceutical powder 1090 with respect to a surface of pharmaceutical powder 1090 in contact with base film 1005 for example. Therefore, even when IC chip 1004 attempts to move in a horizontal direction, chip main body 1006 serves like a wedge, so that a positional displacement due to a lateral movement can be suppressed assuredly.

Further, in the present embodiment, as described above, a horizontal state and a positioning at a center is performed with a high accuracy by protrusions 1067 of positioning guide 1061. Thus, since it can be supplied to a center of pharmaceutical powder 1090 assuredly, positioning is secured without performing, after the supply, an inspection on whether or not it is supplied to a correct position. Therefore, even in the case where an inspection apparatus is provided, it may be a simple sensor for confirming presence of a supply, and an apparatus for which a space region for installation cannot be secured may be used.

Figure 36A:
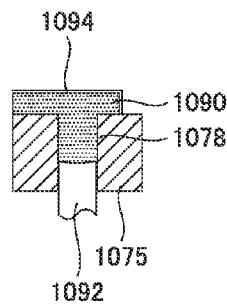
FIG. 36A is a diagram for explaining a function of a tabletting machine main body 1076.
Figure 36B:
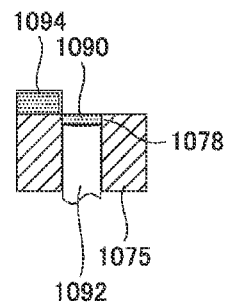
FIG. 36B is a diagram for explaining a function of a tabletting machine main body 1076.

FIGS. 36A to 39C represent an operation of tabletting machine main body 1005. As shown in FIG. 36A, a lower pestle 1092 is fitted to a lower side of die hole 1078 from a lower side slidably upward and downward. As shown in FIG. 39A, an upper pestle 1093 is provided on an upper side of die hole 1078 movably upward and downward. As shown in FIG. 36A, firstly, pharmaceutical powder 1090 is filled into die hole 1078 by pharmaceutical powder filling apparatus in a state where lower pestle 1092 is at a lowered position within die hole 1078. Next, lower pestle 1092 is lifted, and a supply by pharmaceutical powder filling apparatus 1094 is cut, and a certain amount of pharmaceutical powder 1090 is filled into a space of die hole 1078 formed on an upper side of lower pestle 1092 in a leveled state (FIG. 36B). After that, lower pestle 1092 is lowered by a predetermined amount, so that a surface of pharmaceutical powder 1090 is slightly lowered from an upper surface of rotating plate 1075 (FIG. 37A).

Figure 37A:
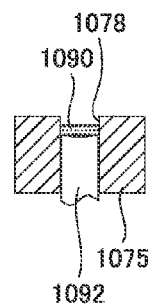
FIG. 37A is a diagram for explaining a function of a tabletting machine main body 1076.
Figure 37B:
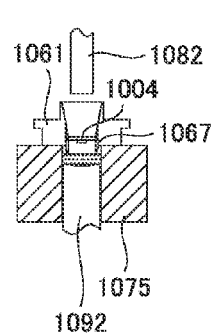
FIG. 37B is a diagram for explaining a function of a tabletting machine main body 1076.
Figure 37C:
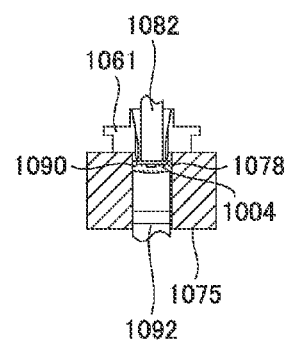
FIG. 37C is a diagram for explaining a function of a tabletting machine main body 1076.

In this state, by means of IC chip supply apparatus 1074 described above, positioning guide 1061 having IC chip 1004 in a downward manner set therein enters die hole 1078 (FIG. 37B), and IC chip 1004 is pushed out and pushed into pharmaceutical powder 1090 by pusher 1082 (FIG. 37C).

Figure 38A:
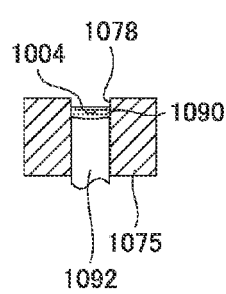
FIG. 38A is a diagram for explaining a function of a tabletting machine main body 1076.
Figure 38B:
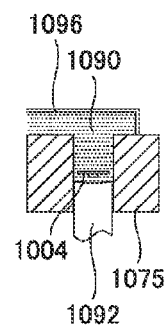
FIG. 38B is a diagram for explaining a function of a tabletting machine main body 1076.
Figure 38C:
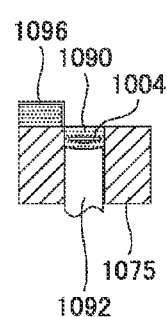
FIG. 38C is a diagram for explaining a function of a tabletting machine main body 1076.

Next, rotating plate 1075 rotates to allow the die hole positioned at the supply position to proceed to the next step (FIG. 38A). In a state where lower pestle 1092 is lowered within die hole 1078, pharmaceutical powder 1090 is filled in die hole 1078 by pharmaceutical powder filling apparatus 1094 (FIG. 38B). Next, lower pestle 1092 is lifted, and a supply by pharmaceutical powder filling apparatus 1094 is cut, and a space of die hole 1078 formed on an upper side of lower pestle 1092 is filled with a certain amount of pharmaceutical powder 1090 in a leveled state (FIG. 38C).

Figure 39A:
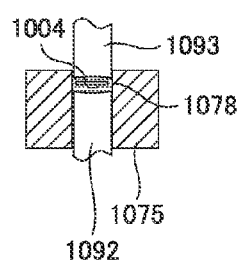
FIG. 39A is a diagram for explaining a function of a tabletting machine main body 1076.
Figure 39B:
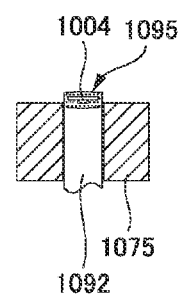
FIG. 39B is a diagram for explaining a function of a tabletting machine main body 1076.
Figure 39C:
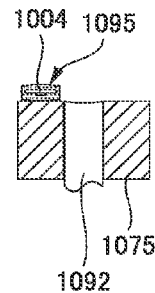
FIG. 39C is a diagram for explaining a function of a tabletting machine main body 1076.

Next, upper pestle 1093 moves downward and compresses pharmaceutical powder 1090 between upper pestle 1093 and lower pestle 1092 (FIG. 39A). Accordingly, pharmaceutical powder 1090 is solidified, so that an IC chip-containing tablet 1095 is manufactured (FIG. 39B). After that, lower pestle 1092 further moves upward to discharge manufactured tablet 1095.

Modified Example

Push-in portion 1064 is not always necessary. Without providing push-in portion 1064, IC chip 1004 may be pushed with a pusher in a state where a lower surface of main body 1062 is in contact with an upper surface of rotating plate 1075. In this case, pharmaceutical powder within the die hole may be filled to an upper end of the die hole to be a leveled state.

Moreover, when push-in portion 1064 is provided as in the above-described embodiment, push-in portion 1064 may enter die hole 1078 and further push the pharmaceutical powder filled in die hole 1078. Accordingly, a recess having an inner shape matching with an outer shape of push-in portion 1064 is formed on a surface of pharmaceutical powder. Therefore, since IC ship 1004 is set within the recess, the positional displacement due to the lateral movement can be suppressed assuredly.

Even in the case where protrusions are provided, it may be omitted at a lower end rather than forming it to a lower end of positioning guide 1061. In such a case, for example, protrusions may be formed only at the main body portion, and protrusions may be omitted at whole or a part of the portion corresponding to the push-in portion.

It should be noted that, in the above-described embodiment, although positioning guide 1061 including protrusions 1067 on the inner circumferential surface is provided, and IC chip 1004 set within positioning guide 1061 is pushed by the pusher, the present invention is not limited to this. For example, a positioning guide without protrusions may be used. Moreover, suction means may be used in place of the pusher to push an IC chip suction by the suction means into the pharmaceutical powder within the die hole.

Moreover, although the IC chip is supplied to the pharmaceutical powder in a downward manner in the above-described embodiment, it may be supplied in an upward manner.

Although IC chip 1004 is accommodated in accommodation tape 1007, and first suction and hold member 1022 takes out the IC chip from the accommodation tape in the above-described embodiment, the present invention is not limited to this. For example, IC chips 1004 may be aligned by, for example, a parts feeder or the like.

<Modified Example of Guide Member>

Figure 40A:
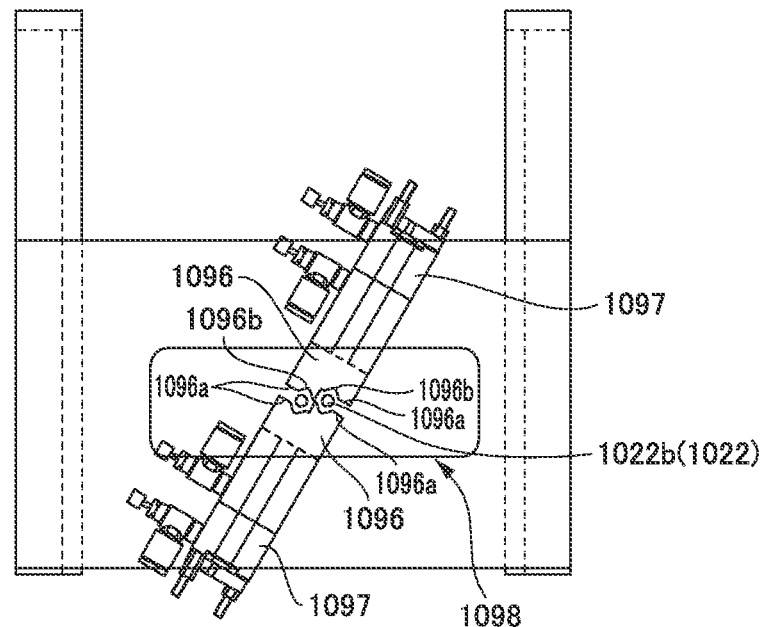
FIG. 40A represents a modified example of a guide member and represents a state where moving guide portions are separated apart and opened.
Figure 40B:
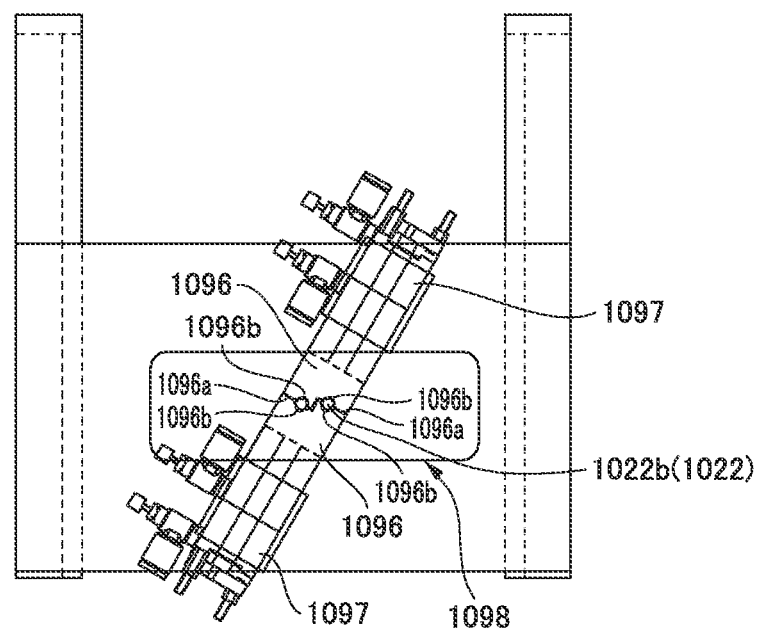
FIG. 40B represents a modified example of a guide member and represents a state where moving guide portions come close to each other and are closed.

In the above-described embodiment, an example is described in which a fixed cylindrical guide 1040 is used as an item constituting a guide member. However, the present invention is not limited to this. For example, it may include a plurality of moving guide members, and a drive mechanism for allowing the moving guide member to come close to and separate from each other, and the plurality of moving guide members may come close to each other to form a through-hole. For example, as shown in FIGS. 40A and 40B, guide member 1098 is configured to allow two moving guide member 1096 to cooperate with cylinders 1097 as respective drive sources and come close to and separate from each other.

Moreover, at a leading end of moving guide member 1096, flat parts 1096a on both sides and recesses 1096b near a center are formed. As shown in FIG. 40A, in a state where two moving guide members 1096 receive a driving force of cylinder 1097 and are separated apart, a space between leading ends is widened. First suction nozzle portion 1022b of first suction and hold member 1022 enters the space. Next, when moving guide members 1096 are moved to come close to each other, flat parts 1096a come into contact with each other, and a through-hole is formed between recesses 1096b. First suction nozzle portion 1022b is controlled so as to be positioned within the through-hole. Moreover, the second suction nozzle portion is also positioned within this through-hole at an appropriate timing and holds IC chip 1004 suctioned and held by first suction nozzle portion 1022b.

Then, even in the case where a center of IC chip 1004 is displaced from a center of first suction nozzle portion 1022b when first suction member 1022 takes out IC chip 1004 from accommodation tape 1007, if moving guide member 1096 is moved com close in a state where first suction and hold member 1022 (first suction nozzle portion 1022b) is positioned between moving guide member 1096 at a position of receiving IC chip 1004, recess 1096b come into contact with a side surface of IC chip 1004, so that IC chip 1004 is moved in the horizontal direction to a center of first suction nozzle portion 1022b, so that positioning can be performed. It should be noted that inner shape dimensions of the through-hole formed by moving guide member 1096 coming close are greater than the outer shape dimensions of IC chip 1004, and IC chip 1004 is not sandwiched and gripped within recessed groove 1096b when both moving guide members 1096 come close to each other, and a smooth transfer from first suction nozzle portion 1022b to second suction nozzle portion 1023c is performed.

Further, moving guide members 1096 may be moved to come close to each other after first suction nozzle portion 1022b and second suction nozzle portion 1023b face and come close to each other. In this manner, the IC chip can be passed assuredly in a state of being surrounded by the first nozzle portion, the second nozzle portion, and the moving guide surface.

Figure 41:
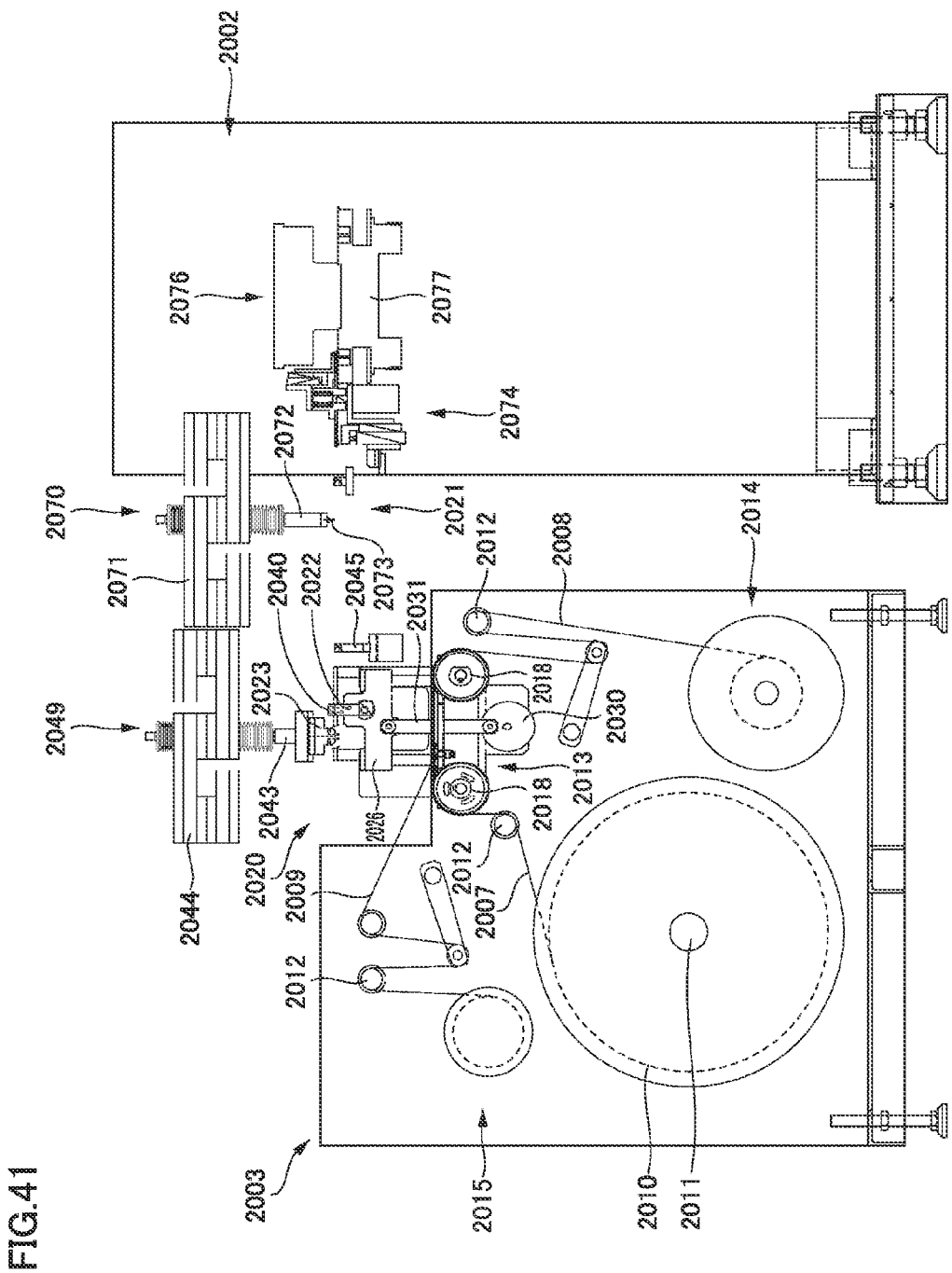
FIG. 41 is a front view representing a favorable one embodiment of a tablet manufacturing apparatus according to the present invention.
Figure 42:
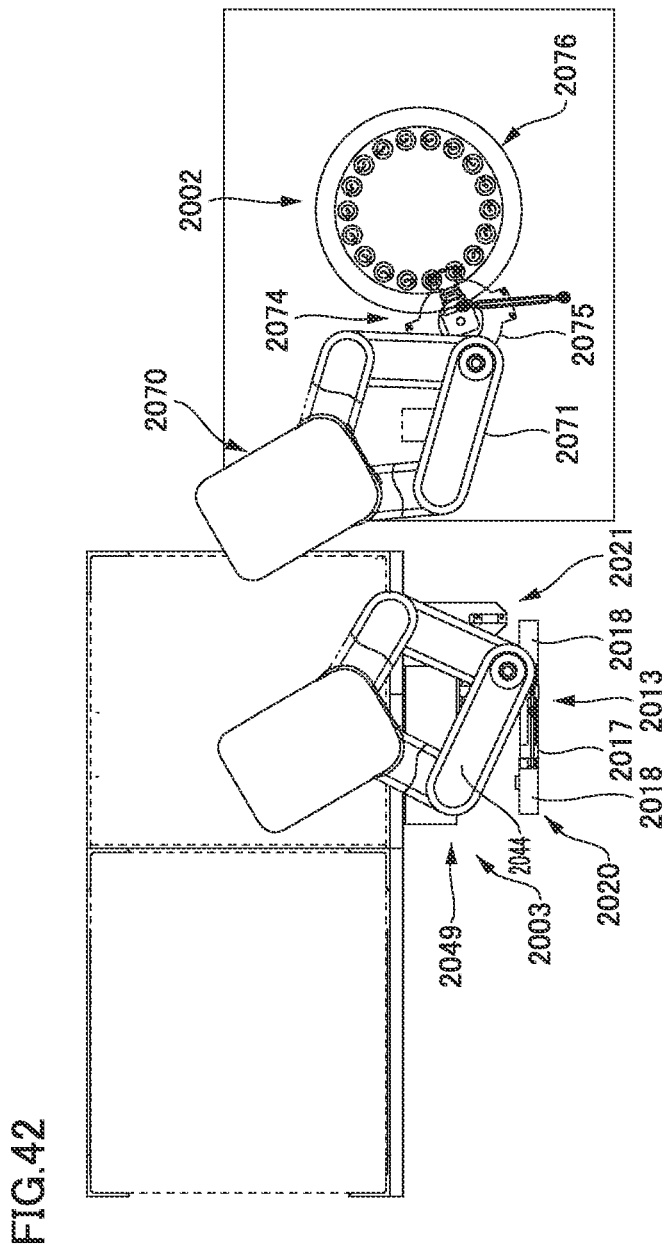
FIG. 42 is a plan view representing a favorable one embodiment of a tablet manufacturing apparatus according to the present invention.
Figure 43:
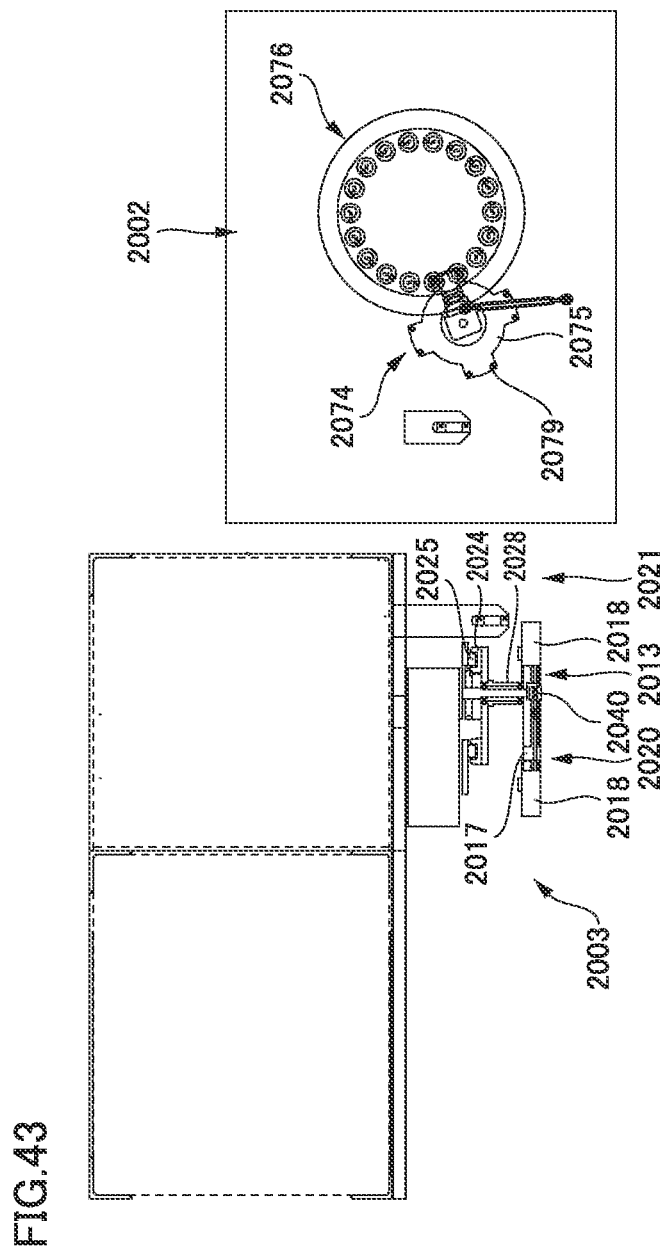
FIG. 43 is a plan view omitting illustration of a robot.
Figure 44A:
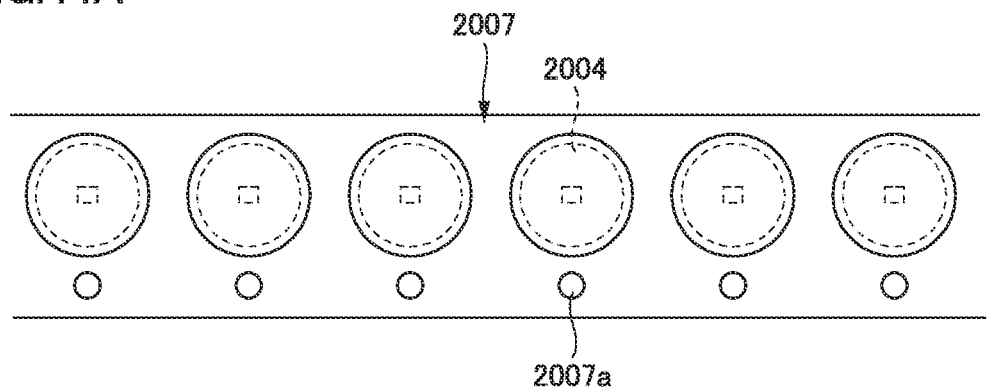
FIG. 44A is a diagram for explaining an IC chip to be supplied.
Figure 44B:
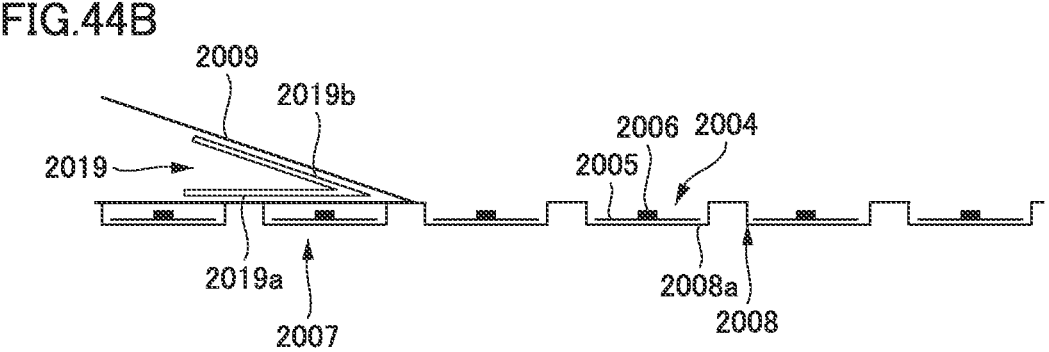
FIG. 44B is a diagram for explaining an IC chip to be supplied.
Figure 44C:
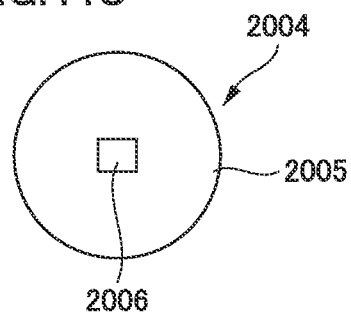
FIG. 44C is a diagram for explaining an IC chip to be supplied.

FIG. 41 is a front view representing a favorable one embodiment of a tablet manufacturing apparatus according to the present invention. FIGS. 42 and 43 are plan views thereof. FIGS. 44A to 44C are diagrams for explaining an IC chip to be supplied in the present embodiment. FIGS. 44A to 44C and subsequent drawings are enlarged views of each portion of an apparatus and an effect thereof.

As shown in FIGS. 41 to 43, a tablet manufacturing apparatus of the present embodiment includes a tabletting machine 2002 and a supply apparatus 2003 for conveying and supplying an IC chip to tabletting machine 2002. IC chip 2004 conveyed and supplied in the present embodiment has a formed in which a chip main body 2006 is mounted at a center position of a circular base film 2005 as shown in FIGS. 44A to 44C. Base film 2005 has a disk-like outer diameter having a diameter of, for example, 3.5 mm, and has, for example, a function of supporting chip main body 2006 and an antenna function of communicating information with outside. Chip main body 2006 has a rectangular outer shape of, for example, 1 mm square, and an electronic circuit is incorporated inside. Chip main body 2006 includes, for example, a storage portion storing information for specifying a tablet into which IC chip 2004 is buried, and a function for transmitting the information stored in the storage portion at a predetermined timing.

IC chip 2004s having the above-described configuration, as shown in FIGS. 44A and 44B, are accommodated in line at predetermined intervals in a belt-like accommodation tape 2007. Accommodation tape 2007 includes a carrier tape 2008 having accommodation recesses 2008a formed at predetermined intervals, and a top tape 2009 covering an upper surface of carrier tape 2008. IC chip 2004 is accommodated in accommodation recess 2008a. In FIG. 44B, as illustrated on the right side, top tape 2009 is peeled off from carrier tape 2008 to open an upper side of accommodation recess 2008a, so that accommodated IC chip 2004 can be taken out. IC chip 2004 is accommodated in accommodation recess 2008a in a state of being in an upward manner where chip main body 2006 is positioned on an upper side. Further, accommodation tape 2007 has feed holes 2007a formed at even pitches along one side edge. This accommodation tape 2007 is taken up by a supply reel 2010.

Supply apparatus 2003 includes, on it front face, a rotary support shaft 2011 freely rotatably bearing-supporting supply reel 2010 configured to take up the above-described accommodation tape 2007 in a rolled form, and supply reel 2010 is set on rotary support shaft 2011. Supply apparatus 2003 includes, on its front face, various rollers 2012 for defining conveying routes of accommodation tape 2007 and separated carrier tape 2008 and top tape 2009, accommodation tape opening portion 2013 peeling off top tape 2009 from carrier tape 2008 to enable taking out IC chip 2004 accommodated in accommodation tape 2007, a carrier tape collecting portion 2014 for collecting carrier tape 2008 after IC chip 2004 is taken out, and a top tape collecting portion 2015 for collecting top tape 2009.

Accommodation tape opening portion 2013 includes a guide plate 2017 constituting a conveying passage arranged in a horizontal direction on an upper predetermined position, a pair of sprockets 2018 arranged on a front side and back side in a conveying direction of accommodation tape 2007 of guide plate 2017, and a peeling plate 2019 arranged on an upper predetermined position of guide plate 2017.

Figure 45A:
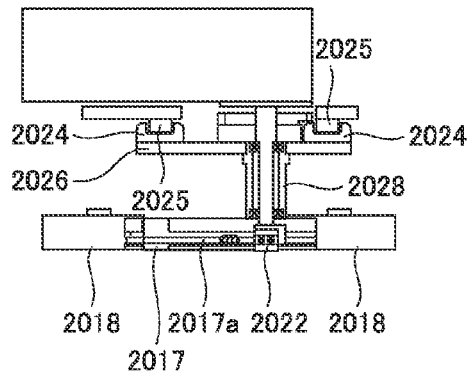
FIG. 45A is a plan view representing an accommodation tape opening portion 2013 and an IC chip take-out apparatus 2020.
Figure 45B:
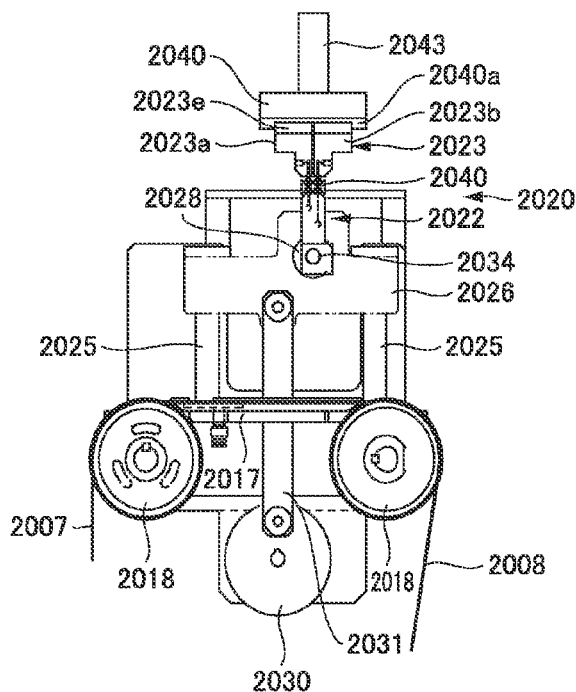
FIG. 45B is a front view representing an accommodation tape opening portion 2013 and an IC chip take-out apparatus 2020.
Figure 45C:
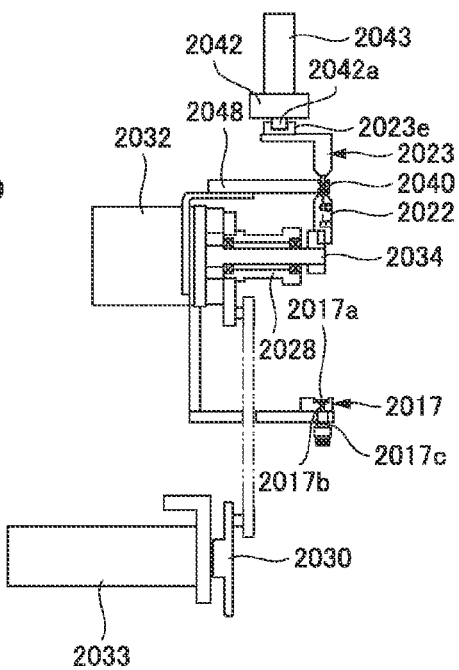
FIG. 45C is a side view representing an accommodation tape opening portion 2013 and an IC chip take-out apparatus 2020.

Guide plate 2017, as shown in FIGS. 45A to 45C by enlargement, has a recessed groove 2017a extending in an axial direction on an upper surface. A width of recessed groove 2017a is set to be equal to or slightly larger than a tape width of accommodation tape 2007. Therefore, accommodation tape 2007 passes within recessed groove 2017a to move forward stably without a positional displacement. Further, as shown in FIGS. 45A to 45C and FIG. 46, in a portion on an upstream side of guide plate 2017, a slit 2017b is formed on a bottom portion of recessed groove 2017a, and slit 2017b communicates with a connection pipe 2017c mounted to a lower surface of guide plate 2017. Connection pipe 2017c cooperates with an unillustrated suction pump. Accordingly, a part having an opened slit 2017b on a bottom surface of recessed groove 2017a generates a negative pressure to suction accommodation tape 2007, so that a stable conveyance can be performed.

Moreover, sprockets 2018 have protrusions 2018a on its circumferential surface at predetermined pitches. When accommodation tape 2007 is passed on sprocket 2018, protrusions 2018a penetrate through feed holes 2007a of accommodation tape 2007 to protrude upward from accommodation tape 2007. Accordingly, when sprockets 2018 are rotated, protrusions 2018a within feed holes 2007a give a conveying force to accommodation tape 2007, so that accommodation tape 2007 follows it and moves forward by a predetermined quantity. When sprockets 2018 are stopped, the forward movement of accommodation tape 2007 is also stopped. Sprocket 2018 cooperates with an unillustrated drive motor such as a servo motor capable of controlling a rotational angle, and an intermittent operation is controlled at a predetermined timing.

Peeling plate 2019, as schematically illustrated in FIG. 44B, includes a reference surface 2019a arranged in parallel with a conveyance surface of accommodation tape 2007, and a slope surface 2019b sloped diagonally backward from reference surface 2019a. Accommodation tape 2007 passes through sprocket 2018 on an upstream side and thereafter passes through a position between guide plate 2017 and peeling plate 2019, and top tape 2009 is folded back by slope surface 2019b from reference surface 2019a of peeling plate 2019 and peeled off from carrier tape 2008. Accordingly, carrier tape 2008 is opened on an upper side of accommodation recess 2008a. Then, carrier tape 2008 is guided by guide plate 2017 and moves horizontally.

It should be noted that carrier tape 2008 passes through accommodation tape opening portion 2013 and thereafter passes through a predetermined passage to reach carrier tape collecting portion 2014 and is taken up and collected by a take-up reel. Similarly, peeled top tape 2009 also passes through a predetermined passage to reach top tape collecting portion 2015, and is taken up and collected by a take-up real and collected.

On an upper side of accommodation tape opening portion 2013, a IC chip take-out apparatus 2020 is provided. This IC chip take-out apparatus 2020 has a function of taking out IC chip 2004 accommodated within opened accommodation tape 2007, reversing an manner upside down, and passing IC chip 2004 to conveying apparatus 2021 in a next stage. In the present embodiment, two front and back IC chips 2004 accommodated in accommodation tape 2007 are taken out collectively. Therefore, sprockets 2018 and the like are operated to intermittently convey accommodation tape 2007 at intervals of two IC chips 2004 and controlled to temporarily stopped in a state where IC chip 2004 is positioned at a take-out position of IC chip take-out apparatus 2020.

Then, IC chip take-out apparatus 2020 includes a first suction and hold member 2022 for taking out IC chip 2004 accommodated in accommodation tape 2007 and reversing IC chip 2004 upside down, and a second suction and hold member 2023 for receiving IC chip 2004 taken out and reversed by first suction and hold member 2022 and supplying IC chip 2004 to conveying apparatus 2021.

First suction and hold member 2022 has two first suction nozzle portions 2022b formed to protrude on a leading end of main body 2022a having an elongated belt-like shape. An arrangement interval of two first suction nozzle portion 2022b matches with an arrangement pitch of IC chip 2004 in accommodation tape 2007. A leading end of first suction nozzle portion 2022b is opened, and the opening part communicates with a suction passage 2022c formed within main body 2022a and first suction nozzle portion 2022b and is connected to an unillustrated suction pump.

Moreover, this first suction and hold member 2022 is configured to move upward and downward and be rotated within a vertical plane. As illustrated in FIGS. 45A to 45C by enlargement, first suction and hold member 2022 is bearing-supported through bearing 2028 with respect to moving plate 2026 moving upward and downward, and moves upward and downward with moving plate 2026. On a back side of moving plate 2026, sliders 2024 are attached which are mounted to be moved upward and downward with respect to two guide rails 2025 extending upward and downward. Moving plate 2026 stably moves upward and downward while being guided by guide rails 2025 and sliders 2024. A drive mechanism for moving this moving plate 2026 upward and downward is configured to couple one end of belt-like coupling plate 2031 to an eccentric position of rotating plate 2030 which is rotated by a rotational force received from drive motor 2033 and couple the other end of coupling plate 2031 to moving plate 2026. Accordingly, rotation of rotating plate 2030 causes coupling plate 2031 and moving plate 2026 to move upward and downward. Then, moving plate 2026 reciprocates between a lifted position shown in FIGS. 41 and 45A to 45C and a lowered position shown in FIG. 46.

Moreover, on a back side of moving plate 2026, a drive motor 2032 is attached which is a drive source for rotating first suction and hold member 2022, and drive motor 2032 also moves upward and downward integrally with moving plate 2026. Rotational shaft 2034 cooperating with an output shaft of drive motor 2032 is mounted to a bearing 2028 arranged to protrude on a front face side of moving plate 2026, and first suction and hold member 2022 is fixed to a leading end of rotational shaft 2034. Accordingly, rotation of drive motor 2032 causes first suction and hold member 2022 to rotate. Then, first suction and hold member 2022 temporarily stops its rotation in two manners of a passing manner having a leading end facing upward as shown in FIGS. 41 and 45A to 45C and a take-out manner having a leading end facing downward as shown in FIG. 46.

Figure 46:
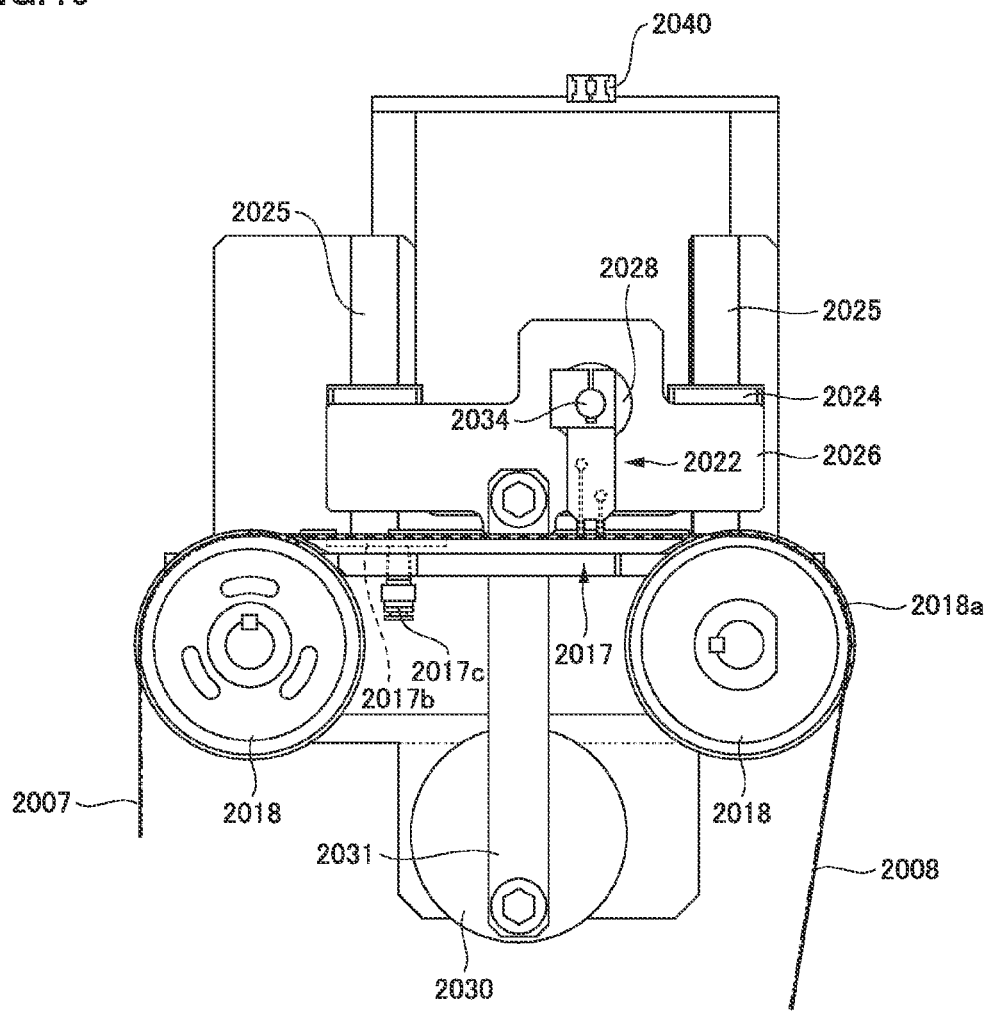
FIG. 46 is an enlarged front view representing an accommodation tape opening portion 2013 and an IC chip take-out apparatus 2020.
Figure 48B:
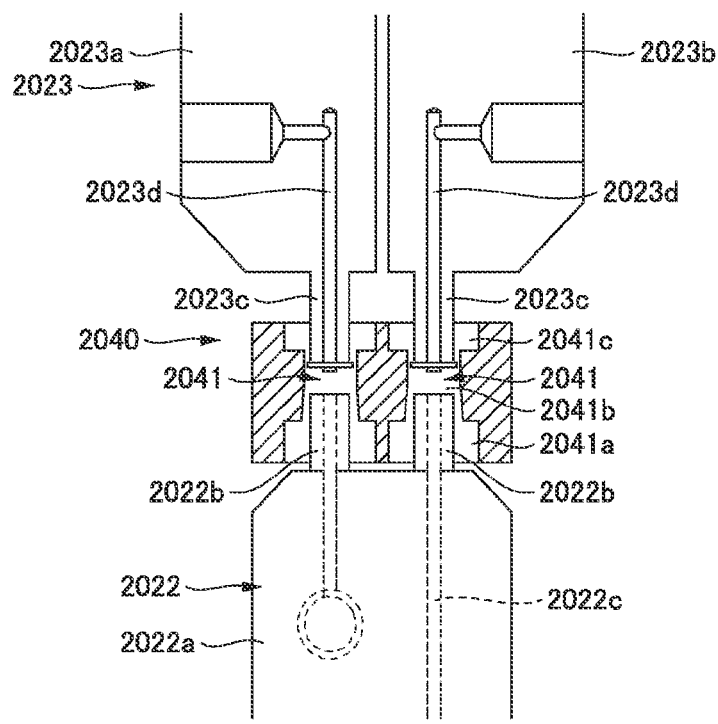
FIG. 48B is an enlarged view representing a main part of FIG. 47B.
Figure 48A:
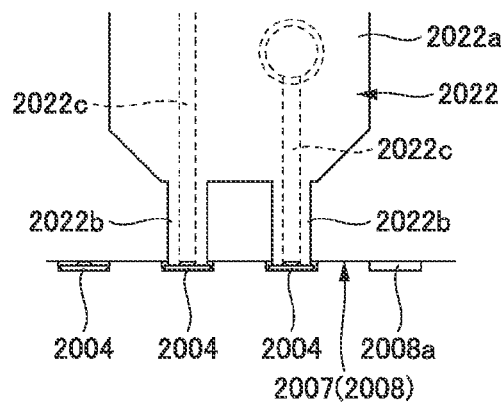
FIG. 48A is an enlarged view representing a main part of FIG. 47A.

Accordingly, when drive motors 2032, 2033 are appropriately controlled to move first suction and hold member 2022 downward in a state of being in a take-out manner of facing downward, a leading end of first suction nozzle portion 2022b comes into contact with IC chip 2004 within accommodation tape 2007 (FIGS. 46, 47A, and 48A). When first suction nozzle portion 2022b communicates with an unillustrated suction pump in this state, suction by first suction nozzle portion 2022b is performed, so that first suction nozzle portion 2022b suctions and holds IC chip 2004.

Next, when moving plate 2026 is moved upward while maintaining first suction and hold member 2022 to be in the downward take-out manner, first suction nozzle portion 2022b of first suction and hold member 2022 is positioned above accommodation tape 2007 in a state of suctioning and holding IC chip 2004. Accordingly, taking out IC chip 2004 from accommodation tape 2007 is completed. Then, moving plate 2026 and first suction and hold member 2022 further moves upward to reach a lifted position. Before reaching the lifted position, first suction and hold member 2022 receives driving of drive motor 2032 and rotates by 180 degrees to shift to a passing manner of facing upward. Accordingly, IC chip 2004 suctioned by first suction nozzle portion 2022b of first suction and hold member 2022 is reversed upside down to be at a flat position in which chip main body 2006 is positioned on a lower side of base film 2005.

As shown in FIGS. 45A to 45C and 47B, a cylindrical guide 2040 is arranged at a position where first suction nozzle portion 2022b of first suction and hold member 2022 when first suction and hold member 2022 is at a lifted position in a passing manner of facing upward. This cylindrical guide 2040 is coupled to a machine frame through a support plate 2048 and the like extending in a horizontal direction and fixedly arranged at a desired position. Cylindrical guide 2040 includes two through-holes 2041 extending upward and downward. Two through-holes 2041 have parallel axes, and a pitch between axes is matched with an arrangement pitch of first suction nozzle portion 2022b. Moreover, each through-hole 2041 includes a inlet region 2041a at a lower end, a center region 2041b, and an outlet region 2041c at an upper end. Inner diameter dimensions of inlet region 2041a and outlet region 2041c are set to be enough larger than outer shape dimensions of IC chip 2004, and inner shape dimensions of center region 2041b are set to be substantially equal to or greater than outer shape dimensions of IC chip 2004. Further, the inner circumferential surface of center region 2041b is set to be a tapered surface having a narrowest center in the up/down direction. Then, when first suction and hold member 2022 moves upward while maintaining a passing manner of facing upward, first suction nozzle portion 2022b enters inlet region 2041a from a lower end of cylindrical guide 2040. After having reached the lifted position, a leading end of first suction nozzle portion 2022b is positioned within center region 2041b. More specifically, it is positioned near a narrowest center position within center region 2041b. Accordingly, the entering of IC chip 2004 suctioned and held by first suction nozzle portion 2022b into cylindrical guide 2040 passes through inlet region 2040a having a relatively large size, and moves within center region 2041b having a gradually reduced inner diameter, so that it can move smoothly to a lifted position.

On the other hand, second suction and hold member 2023 includes a first main body 2023a and a second main body 2023b which come closest to and separate from each other in a horizontal direction. Second suction nozzle portions 2023c are provided respectively at leading ends of first and second main bodies 2023a, 2023b. An arrangement interval of two second suction nozzle portions 2023c in the state where first main body 2023a and second main body 2023b come close to each other is set to match with an arrangement interval of first suction nozzle portion 2022b of first suction and hold member 2022. Further, a leading end of second suction nozzle portion 2023c is opened, and the opened part communicates with suction passage 2023d formed within first and second main bodies 2023a, 2023b and second suction nozzle portions 2023c, and are connected to an unillustrated suction pump.

Moreover, this second suction and hold member 2023 is configured to move within a three dimensional space. This movement is performed by a first robot 2049. In other words, first robot 2049 includes an arm 2044 of a SCARA robot moving in a horizontal plane, a support rod 2043 attached to be movable in an upward and downward directions to a leading end lower surface of arm 2044, and a base 2042 attached to a lower end of support rod 2043. By the horizontal movement of arm 2044 of the SCARA robot and the upward and downward movement of support rod 2043, base 2042 can be moved to a desired position within a three dimensional space. Then, first main body 2023a and second main body 2023b constituting second suction and hold member 2023 are movably attached through sliders 2023e to guide rails 2042a provided at a lower surface of base 2042. The movement of first main body 2023a and second main body 2023b is performed for example by cylinder driving. Accordingly, base 2042 and second suction and hold member 2023 supported on the lower surface of base 2042 move within the three dimensional space. Further, first main body 2023a and second main body 2023b come close to and separate from each other along guide rails 2042a.

Specifically, second suction and hold member 2023 moves to a position of overlapping with cylindrical guide 2040 within the horizontal plane in accordance with the operation of arm 2044 of the SCARA robot, and support rod 2043 moves downward while maintaining that state, so that second suction and hold member 2023 reaches a lowered position. At this time, first main body 2023a and second main body 2023b are in a state of being close to each other. In this state, as shown in FIGS. 45A to 45C, 47B, and 48B, second suction nozzle portion 2023c enters outlet region 2041c from an upper end of cylindrical guide 2040. Then, after reaching a lowermost end position, a leading end of second suction nozzle portion 2023c is positioned within center region 2041b. In this state, it is controlled to come close with a certain clearance (for example, about 0.5 mm) to a leading end of first suction nozzle portion 2022b of first suction and hold member 2022 positioned at a lifted position.

Accordingly, IC chip 2004 suctioned and held by first suction nozzle portion 2022b waits in a state of being positioned in center region 2041b of through-hole 2041 of cylindrical guide 2040, and a lower end of second suction nozzle portion 2023c of second suction and hold member 2023 entered into cylindrical guide 2040 from above comes into contact with or close to IC chip 2004. Then, suction by second suction nozzle portion 2023c is started, and suction by first suction nozzle portion 2022b is stopped at an appropriate timing, so that suctioning and holding of IC chip 2004 is shifted to the side of second suction and hold member 2023.

As can be seen, the present embodiment is characterized in performing a transfer of IC chip 2004 from first suction and hold member 2022 to second suction and hold member 2023 within cylindrical guide 2040. Since IC chip 2004 has, for example, a small diameter of 3.5 mm and has a thin shape of base film 2005, holding with the suction and hold member cannot be performed firmly. Therefore, when passing from first suction and hold member 2022 to second suction and hold member 2023 is performed in a state where IC chip 2004 is exposed, there is a likelihood that the passing cannot be performed smoothly and IC chip 2004 is dropped. However, in the present embodiment, since the passing process is performed inside of cylindrical guide 2040, the passing can be performed assuredly.

After that, first suction and hold member 2022 moves downward while maintaining the passing manner. When first suction nozzle portion 2022b goes out of cylindrical guide 2040, it rotates by 180 degrees, takes a take-out manner, and returns to a lowered position at an appropriate timing, and prepares for the next operation of taking out the IC chip. On the other hand, second suction and hold member 2023 having received IC chip 2004 moves upward along with the lifting of support rod 2043, and second suction nozzle portion 2023c is positioned on an upper side of cylindrical guide 2040. After that, second suction and hold member 2023 is moved in a horizontal direction by the operation of arm 2044 of the SCARA robot to reach the conveying-in position of conveying apparatus 2021.

Figure 49A:
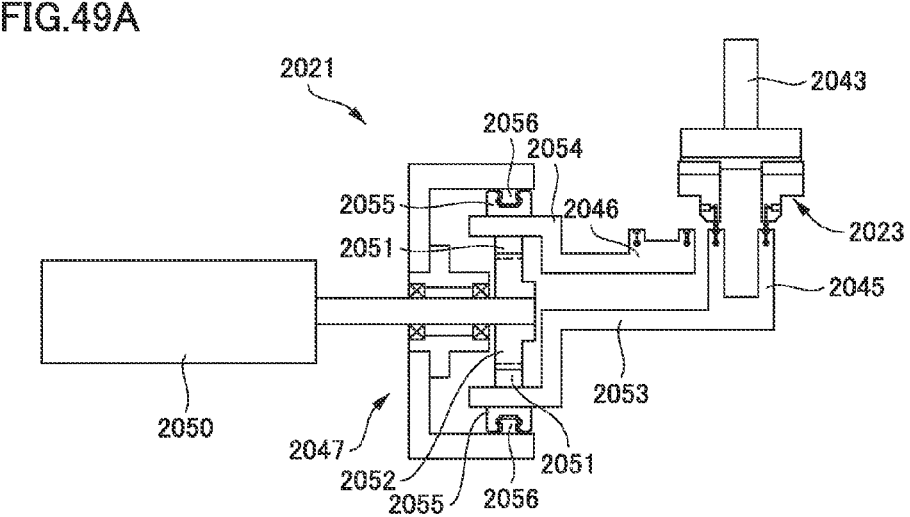
FIG. 49A is a side view representing a conveying apparatus 2021.
Figure 49B:
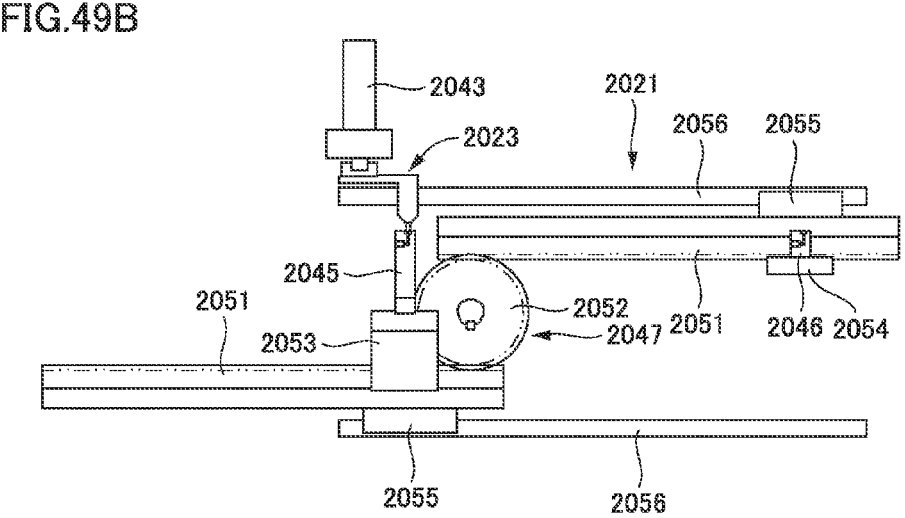
FIG. 49B is a front view representing a conveying apparatus 2021.

Conveying apparatus 2021, as shown in FIGS. 49A to 49B, includes a first receiving portion 2045 and a second receiving portion 2046 for receiving two IC chips 2004 suctioned and held and conveyed by second suction and hold member 2023, and a drive mechanism 2047 for moving first receiving portion 2045 and second receiving portion 2046 forward and backward. As shown in FIGS. 50A and 50B by enlargement, first receiving portion 2045 includes, on an upper surface of two pillar portions 2045a separated into two legs facing upward, a recess 2045b accommodating IC chip 2004. An interval of pillar portions 2045a (recesses 2045b) is inconformity with the tabletting machine in the next stage, and is set to be longer than an arrangement pitch of IC chips 2004 in accommodation tape 2007 (an arrangement interval of first suction nozzle portion 2022b and second suction and hold member 2023). Moreover, a bottom surface of recess 2045b communicates with suction passage 2045c formed within pillar portion 2045a and is connected to an unillustrated suction pump. Accordingly, IC chip 2004 set within recess 2045b is suctioned and held within recess 2045b. Even when first receiving portion 2045 moves forward, IC chip 2004 moves forward with first receiving portion 2045 while being set within recess 2045b.

Similarly, second receiving portion 2046 includes, on an upper surface of two pillar portions 2046a separated into two legs facing upward, recess 2046b for accommodating IC chip 2004. An interval of pillar portions 2046a (recesses 2046b) is in conformity with a tabletting machine in the next stage, and is set to be longer than an arrangement pitch of IC chips 2004 in accommodation tape 2007 (an arrangement interval of first suction nozzle portion 2022b and second suction and hold member 2023). Moreover, a bottom surface of recess 2046b communicates with suction passage 2046c formed within pillar portion 2046a and is connected to an unillustrated suction pump. Accordingly, IC chip 2004 set within recess 2046b is suctioned and held within recess 2046b. Even when second receiving portion 2046 moves forward, IC chip 2004 moves forward with second receiving portion 2046 while being set within recess 2046b.

A drive mechanism 2047 for first receiving portion 2045 and second receiving portion 2046 includes a drive motor 2050, and a rack 2051 and a pinion 2052 which receive an output of drive motor 2050 and converts it into a reciprocating linear motion. First receiving portion 2045 and second receiving portion 2046 cooperate with corresponding rack 2051 respectively through coupling plates 2053, 2054 and move in a reverse direction. In other words, when first receiving portion 2045 moves forward, second receiving portion 2046 moves backward. When first receiving portion 2045 moves forward, second receiving portion 2046 moves backward. In other words, for example, when first receiving portion 2045 is at a conveying-in position, second receiving portion 2046 is at a conveying-out position. Moreover, for example, when first receiving portion 2045 is at a conveying-out position, second receiving portion 2046 is at a conveying-in position. Moreover, sliders 2055 are coupled to a lower surface of coupling plate 2053 and an upper surface of coupling plate 2054. Sliders 2055 are mounted respectively to corresponding guide rails 2056 and guides forward and backward movement of rack 2051 and each of receiving portions 2045, 2046 along with rotation of pinion 2052.

Second suction and hold member 2023 having received IC chip 2004 moves within a horizontal plane by means of arm 2044 of the SCARA robot, and is positioned above first receiving portion 2045 or second receiving portion 2046 positioned at a conveying-in position. As described above, since first receiving portion 2045 and second receiving portion 2046 move forward and backward in reverse directions with each other, first robot 2049 controls an operation of arm 2044 of the SCARA robot to position second suction and hold member 2023 alternately above the conveying-in position of first receiving portion 2045 and above the conveying-in position of second receiving portion 2046.

As described above, since intervals of pillar portions 2045 (recesses 2045b) of first receiving portion 2045 and pillar portions 2046a (recesses 2046b) of second receiving portion 2046 are widened, first robot 2049 performs a control of separating first main body 2023a and second main body 2023b of second suction and hold member 2023 each other and widening an interval of second suction nozzle portions 2023c during the horizontal movement of second suction and hold member 2023 by arm 2044 of the SCARA robot or at the time of being positioned above the conveying-in position. This widened interval of second suction nozzle portion 2023c is set to be equal to an interval of recesses 2045b, 2046b.

Then, when support rod 2043 is moved downward in a state where first main body 2023a and second main body 2023b are separated from each other, as shown in FIG. 50A, a lower end of second suction nozzle portion 2023c of second suction and hold member 2023 enters into recess 2045b of first receiving portion 2045, so that IC chip 2004 suctioned and held in a downward manner is set within recess 2045b. Then, when suction on the side of second suction and hold member 2023 is released at an appropriate timing, IC chip 2004 is transferred to recess 2045b of first receiving portion 2045. Moreover, first receiving portion 2045 starts suction in advance or at an appropriate timing to suction and hold IC chip 2004 within recess 2045b.

Second suction and hold member 2023 having completed a supply of IC chip 2004 to first receiving portion 2045 returns to a passing position within cylindrical guide 2040 by an operation of first robot 2049 and supplies a next passed IC chip to recess 2046b of second receiving portion 2046.

On the other hand, first receiving portion 2045 having received a supply of IC chip 2004 moves forward and is positioned at a conveying-out position. IC chip 2004 within recess 2045b of first receiving portion 2045 having reached the conveying-out position is suctioned and held by a second robot 2070, and transferred to tabletting machine 2002. Second robot 2070 includes an arm 2071 of the SCARA robot moving within the horizontal plane, a support member 2072 attached movably upward and downward on a leading end lower surface of arm 2071, and a pair of third suction nozzle portions 2073 attached to a lower end of support member 2072.

A leading end of third suction nozzle portions 2073 is opened, and the opened part communicates with suction passages 2073a formed within third suction nozzle portion 2073 and is connected to an unillustrated suction pump. Then, by the horizontal movement of arm 2071 of the SCARA robot and the upward and downward movement of support member 2072, third suction nozzle portions 2073 can move to a desired position within the three dimensional space. Further, an interval of the pair of third suction nozzle portions 2073 is in conformity with arrangement intervals of pillar portions 2045a (recesses 2045b9 of first receiving portion 2045 and pillar portions 2046a (recesses 2046b) of second receiving portion 2046.

Accordingly, suction by the suction pump is performed when the lower end of third suction nozzle portions 2073 has reached recess 2045b of first receiving portion 2045 or recess 2046b of second receiving portion 2046 at the conveying-out position by the operation of second robot 2070. When the suction by the vacuum pump on the side of first receiving portion 2045 or second receiving portion 2046 is released, IC chip 2004 is suctioned and held on the side of third suction nozzle portion 2073 (refer to FIG. 50B).

Figure 51A:
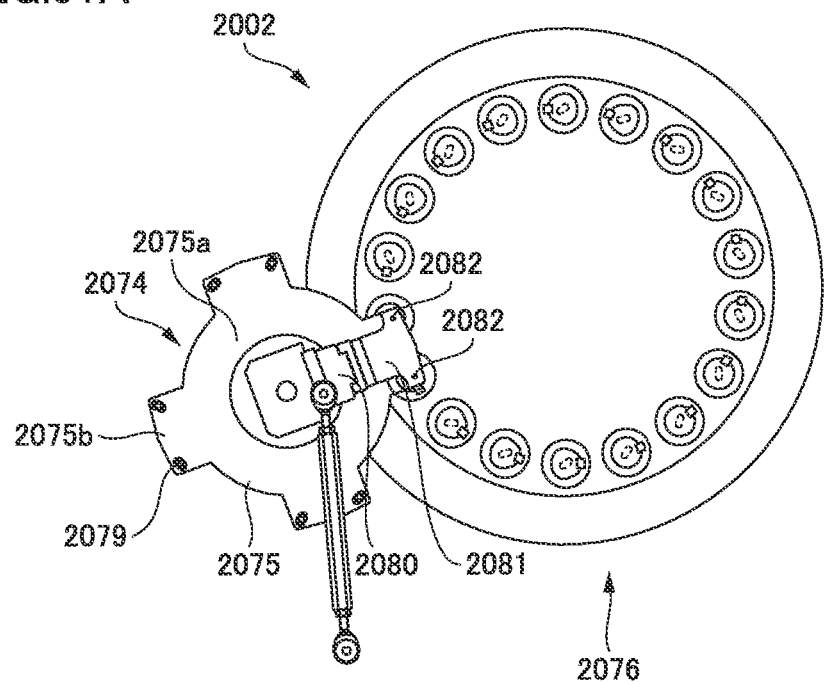
FIG. 51A is a plan view representing a tabletting machine.
Figure 51B:
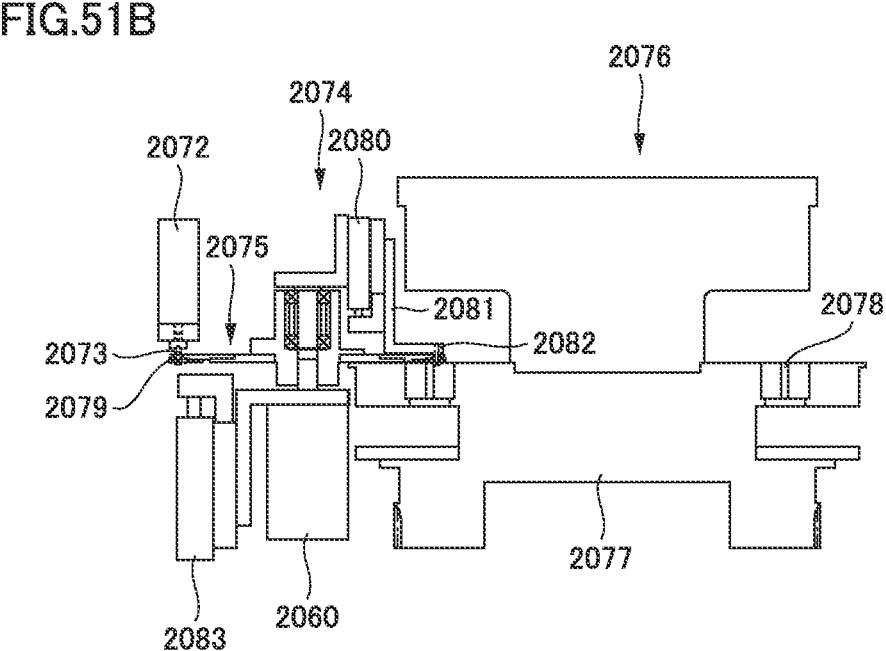
FIG. 51B is a front view representing a tabletting machine.

Next, when third suction nozzle portion 2073 suctioning and holding IC chip 2004 moves upward, horizontally, and downward by the operation of second robot 2070, as shown in FIGS. 42 and 51B, it is positioned within IC chip receiving portion 2079 of rotary table 2075 of IC chip supply apparatus 2074 arranged on a conveying-in side of tabletting machine 2002. When the suction by third suction nozzle portion 2073 is released in this state, IC chip 2004 is supplied to IC chip receiving portion 2079.

Tabletting machine 2002 includes IC chip supply apparatus 2074 described above and a tabletting machine main body 2076. Tabletting machine main body 2076 is similar to a conventionally existing tabletting machine, and it fills pharmaceutical powder into a plurality of die holes 2078 provided at predetermined intervals on a circumference along an outer edge portion of rotating plate 2077, and compresses and shapes the filled pharmaceutical powder with a lower pestle and an upper pestle to manufacture a tablet. In the present embodiment, in order to manufacture an IC chip-containing tablet, a function of firstly supplying IC chip 2004 by means of IC chip supply apparatus 2074 onto a predetermined amount of pharmaceutical powder supplied into die hole 2078, further filing pharmaceutical powder onto IC chip 2004, and compressing and shaping these pharmaceutical powder and the IC chip from above and below is provided. Details of the manufacturing processes for a tablet will be described later.

IC chip supply apparatus 2074 as a main part of the present invention includes rotary table 2075 described above, and supplies and aligns IC chips 2004 supplied to rotary table 2075 within die holes 2078 of tabletting machine main body 2076. Rotary table 2075 is rotated by a rotational force received from drive motor 2060. In the present embodiment, it is controlled to rotate intermittently at 90 degrees intervals. Moreover, rotary table 2075 includes protruding parts 2075b protruding outward on an outer circumference of plate-like main body 2075a at 90 degrees intervals. An IC chip receiving portion 2079 is provided at this protruding part 2075b. Since IC chips 2004 are supplied in two-pieces unit from the side of supply apparatus 2003, two IC chip receiving portions 2079 are provided at each protruding part 2075b. In the present embodiment, a position rotated by 180 degrees from supply apparatus 2003 on an upstream side is a position of supplying IC chip 2004 to tabletting machine main body 2076. Then, it is temporarily stopped at a position rotated by 90 degrees from the IC chip receiving position. However, at this time, it is favorable to provide, for example, an inspection apparatus for performing an inspection on whether or not an IC chip is correctly supplied to IC chip receiving portion 2059.

Figure 52:
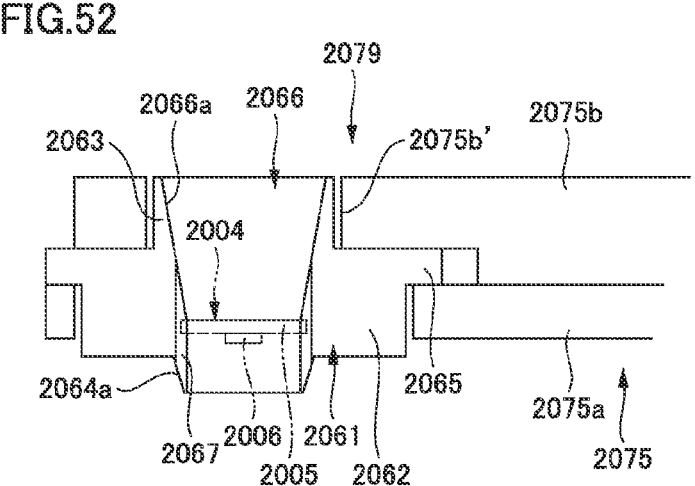
FIG. 52 is an enlarged view representing a main part of an IC chip supply apparatus 2074.
Figure 53A:
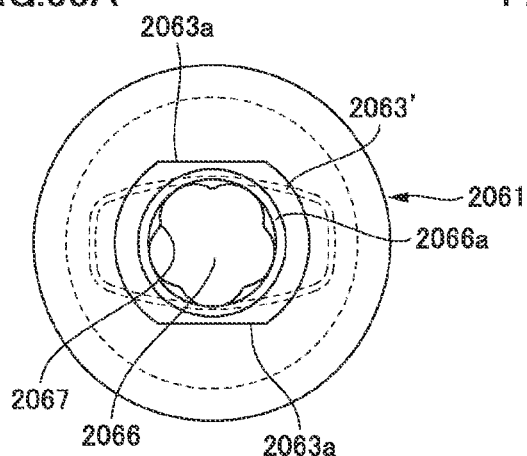
FIG. 53A is a plan view representing a positioning guide 2061.
Figure 53C:
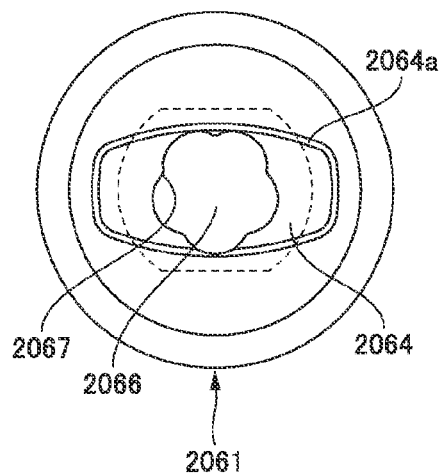
FIG. 53C is a bottom view representing a positioning guide 2061.
Figure 53B:
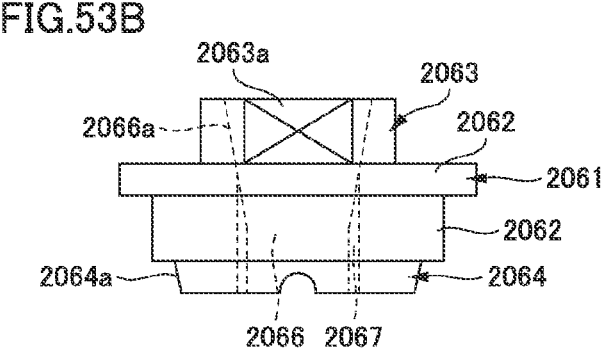
FIG. 53B is a front view representing a positioning guide 2061.

As shown in FIG. 52 by enlargement, through-hole 2075b' penetrating up and down at a specified position of protruding part 2075b of rotary table 2075 is provided, and positioning guide 2061 is mounted to through-hole 2075b'. This positioning guide 2061 constitutes IC chip receiving portion 2059. As shown in FIGS. 53A to 53C, positioning guide 2061 has a ring-like basic shape having a through-hole penetrating up and down.

Positioning guide 2061 includes a flange portion 2065 protruding radially outward on an upper circumferential side surface of a cylindrical main body 2062, and a convex portion 2063 protruding upward is provided at a center of an upper surface of main body 2062. Convex portion 2063 includes on its side surface a flat surface 2063a. Convex portion 2063 is inserted into through-hole 2075b' of protruding part 2075b, and flange portion 2065 is sandwiched and held by protruding part 2075b and main body 2075a. Accordingly, movement of positioning guide 2061 in an axial direction, in other words, an up/down direction is suppressed, so that separation of positioning guide 2061 from rotary table 2075 is prevented. Further, the inner circumferential surface shape of through-hole 205b' of protruding part 2075b is set to be substantially matching with the outer circumferential surface shape of convex portion 2063 of positioning guide 2061. Accordingly, rotation of positioning guide 2061 about an axis is prevented. Accordingly, positioning guide 2061 is held by rotary table 2075 at a correct position and in a correct manner.

Through-hole 2066 provided at positioning guide 2061 is a tapered surface 2066a in which a cross section in an upper region is circular and has a larger diameter as it goes upward. This upper region is a region in which convex portion 2063 is mainly formed. An inner diameter of through-hole 2066 at an upper end of convex portion 2063 is larger than an outer diameter of IC chip 2004, and IC chip 2004 suctioned and held by third suction nozzle portions 2073 enters through-hole 2066 of positioning guide 2061 along with lowering of third suction nozzle portion 2073. The entering is guided by tapered surface 2066a to promote a smooth downward movement.

Moreover, the inner circumferential surface in a portion of main body 2062 of through-hole 2066 has a plurality of protrusions 2067 formed to protrude toward a center. In the present embodiment, five protrusions 2067 are provided. However, the number may be three for example, or any other number may be used. A leading end position of protrusion 2067 is positioned on an imaginary circumference which is concentric with through-hole 2066 and has a predetermined diameter. This predetermined diameter may be equal to or slightly narrower than a diameter of IC chip 2004. Accordingly, a circumferential edge of IC chip 2004 inserted to through-hole 2066 of positioning guide 2061 is supported by protrusions 2067, and held in a state where a center of IC chip 2004 matches with a center of positioning guide 2061 (through-hole 2066). Accordingly, positioning is performed with a high accuracy. Moreover, it is preferable to manufacture positioning guide 2061 with an elastic body such as rubber since it holds IC chip 2004 more firmly. Furthermore, protrusions 2067 are preferably arranged at equal intervals in the circumferential direction. It is preferable since IC chip 2004 is evenly supported.

Further, in the present embodiment, a push-in portion 2064 is provided on a lower surface of main body 2062. A planar shape of this push-in portion 2064 is substantially elliptical as shown in FIG. 53C. In this example, it has a flat collapsed shape on both ends of elliptical shape on the long diameter side. The planar shape of this push-in portion 2064 is based on a shape of a tablet to be manufactured, and is slightly smaller than the tablet. In other words, it has a shape slightly smaller than a cross-sectional shape of die hole 2078 formed in tabletting machine main body 2076. Moreover, push-in portion 2064 has a tapered surface 2064a having a peripheral surface becoming smaller as it goes downward. Further, in the present embodiment, protrusions 2067 formed on the inner circumferential surface of through-hole 2066 is formed to a lower end of this push-in portion 2064.

Figure 54A:
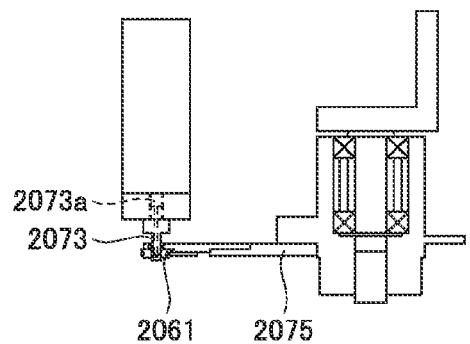
FIG. 54A is a diagram for explaining an operation of an IC chip supply apparatus 2074.
Figure 55A:
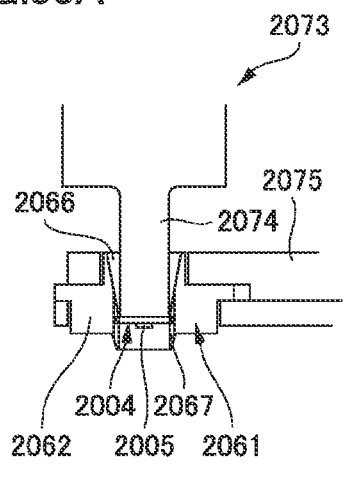
FIG. 55A is an enlarged view representing a main part of FIG. 54A.

Next, a supply of IC chip 2004 from supply apparatus 2003 to IC chip supply apparatus 2074 and a supply operation of IC chip 2004 to tabletting machine will be described, and a configuration of IC chip supply apparatus 2074 will be described. FIGS. 54A and 55A show a state where a leading end of third suction nozzle portion 2073 of supply apparatus 2003 is inserted into positioning guide 2061 constituting IC chip receiving portion 2059. As shown in the drawings, second suction and hold member 2023 moves downward, and a leading end of third nozzle portion 2073 in a state of suctioning and holding IC chip 2004 enters through-hole 2066 of positioning guide 2061, and stops at an appropriate position of main body 2062. At this appropriate position, IC chip 2004 is supported by protrusions 2067. Since suction by third suction nozzle portion 2073 is performed until reaching this stopped position, IC chip 2004 moves downward while maintaining a horizontal state in a downward manner having chip main body 2006 below, and at the lower stopping position of third suction nozzle portion 2073, IC chip 2004 comes into contact with a plurality of protrusions 2067 in a horizontal manner.

Next, suction by third suction nozzle portion 2073 is released, and third suction nozzle portion 2073 moves upward and separates from positioning guide 2061, and goes on to take next IC chip. On the other hand, IC chip 2004 in a downward manner remaining in positioning guide 2061 is supported in a state of maintaining a horizontal manner by means of protrusions 2067 of positioning guide 2061. Further, as described above, a centering of IC chip 2004 is also performed with a high accuracy.

Figure 54B:
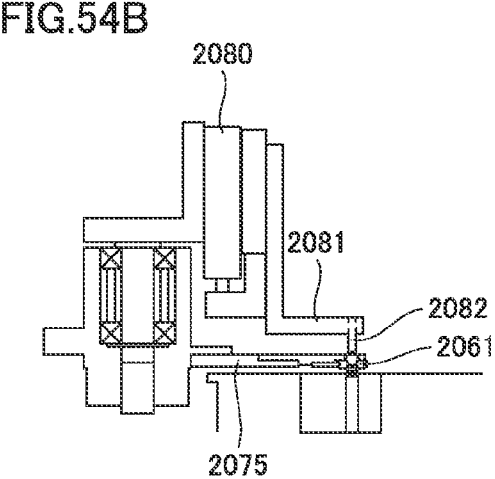
FIG. 54B is a diagram for explaining an operation of an IC chip supply apparatus 2074.
Figure 55B:
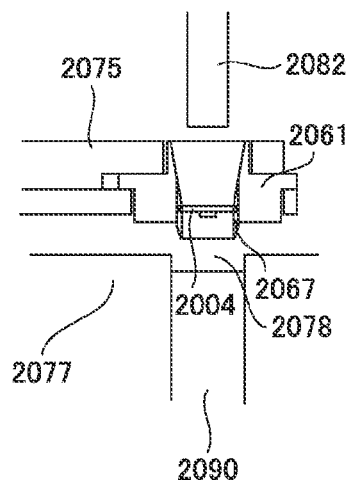
FIG. 55B is an enlarged view representing a main part of FIG. 54B.

Drawings subsequent to FIGS. 54B and 55B show a supply position to tabletting machine 2002 in which rotary table 2075 is rotated by 180 degrees from the state of FIGS. 54A and 55A. At this supply position, two pushes 2082 are suspended and formed at a leading end lower surface of an L-shaped plate 2081 moving upward and downward with a driving of first cylinder 2080. Two pushers 2082 are in conformity with an arrangement pitch of two positioning guides 2061 adjacent to each other in a circumferential direction, and are adjusted so that an axis center of each positioning guide 2061 and an axis center of pusher 2082 matches when the rotary table is temporarily stopped.

Further, first cylinder 2080, L-shaped plate 2081, pushers 2082, and rotary table 2075 are movable upward and downward integrally. Then, the upward and downward movement is performed by receiving driving of second cylinder 2083.

Therefore, by appropriately switching the reciprocating operation of first cylinder 2080 and second cylinder 2083, positions of rotary table 2075 and pushers 2082 can be changed. For example, FIGS. 54B and 55B shows a state in which second cylinder 2083 allows first cylinder 2080, L-shaped plate 2081, pushers 2082, and rotary table 2075 to be positioned at a lifted position, and first cylinder 2080 further allows pushers 2082 to be positioned at a lifted position. In this state, rotary table 2075 separates apart from an upper surface of rotating plate 2077 of tabletting machine main body 2076, and positioning guide 2061 also separates apart from an upper surface of rotating plate 2077. Moreover, a lower surface of pusher 2082 is positioned on an upper side of positioning guide 2061, and IC chip 2004 in a downward manner supported by pushers 2082 and positioning guide 2061 is in a non-contact state. This state is an initial state in which rotary table 2075 is rotated to reach a supply position and temporarily stopped.

Figure 54C:
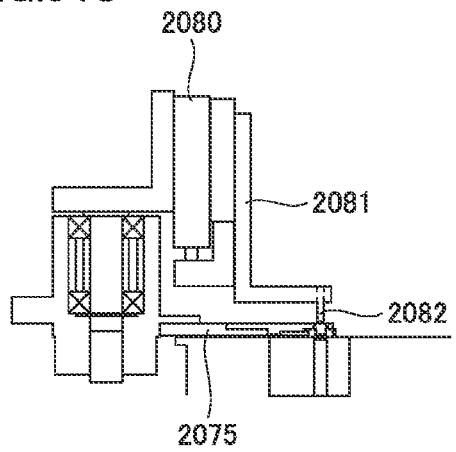
FIG. 54C is a diagram for explaining an operation of an IC chip supply apparatus 2074.
Figure 55C:
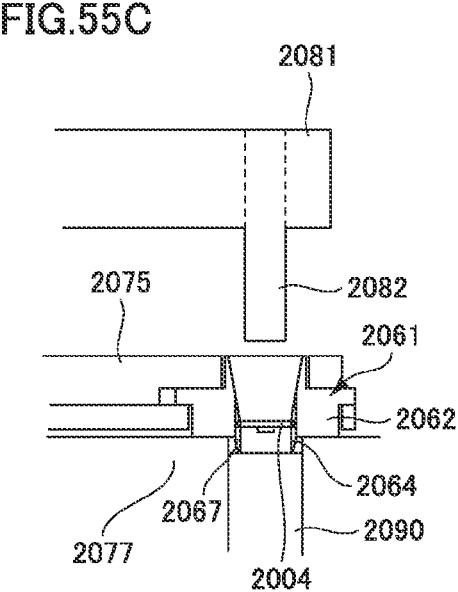
FIG. 55C is an enlarged view representing a main part of FIG. 54C.

Next, only second cylinder 2083 is operated to allow first cylinder 2080, L-shaped plate 2081, pushers 2082, and rotary table 2075 to be positioned at a lowered position. Accordingly, as shown in FIGS. 54C and 55C, rotary table 2075 comes close to an upper surface of rotating plate 2077 of tabletting machine main body 2076, so that a lower surface of main body 2062 of positioning guide 2061 comes into contact with an upper surface of rotating plate 2077. Further, push-in portion 2064 enters die hole 2078, and comes into contact with pharmaceutical powder filled in die hole 2078. Moreover, at this time, since first cylinder 2080 remains in the initial state, a relative positional relationship between pushers 2082 and positioning guide 2061 does not change, and a lower surface of pusher 2082 is positioned on an upper side of positioning guide 2061, and pusher 2082 and IC chip 2004 in a downward manner supported by positioning guide 2061 are in a non-contact state.

Figure 54D:
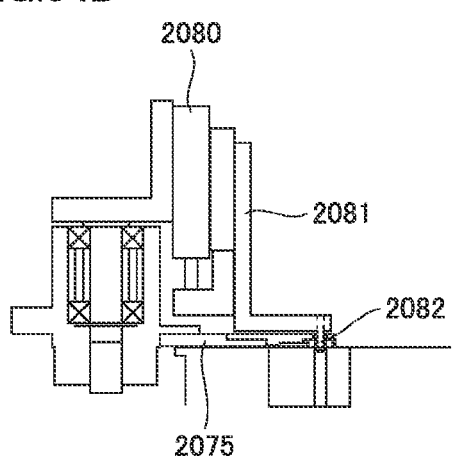
FIG. 54D is a diagram for explaining an operation of an IC chip supply apparatus 2074.
Figure 55D:
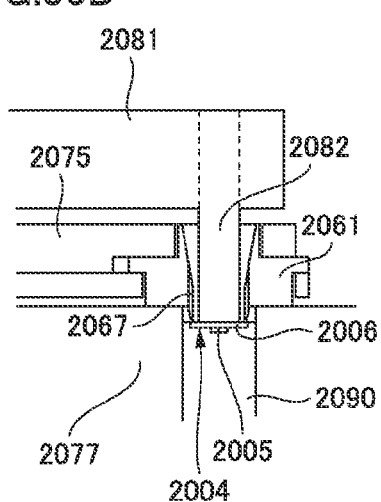
FIG. 55D is an enlarged view representing a main part of FIG. 54D.

After that, first cylinder 2080 moves while second cylinder 2083 maintaining the above-described state, and pusher 2082 moves downward. Accordingly, as shown in FIGS. 54D and 55D, a lower end of pusher 2082 reaches a lower end of positioning guide 2061, in other words, a lower end of push-in portion 2064, and IC chip 2004 is forced downward by pusher 2082 and pushed out from positioning guide 2061, and pushed into pharmaceutical powder 2090. Also during this downward movement of IC chip 2004 by pusher 2082, IC chip 2004 moves while maintaining a horizontal state and centering by protrusions 2067 of positioning guide 2061. Accordingly, when being pushed out of positioning guide 2061 and finally pushed in and supplied to pharmaceutical powder 2090, it is supplied with a high accuracy to a center of a surface of pharmaceutical powder 2090 filled in die hole 2078. Moreover, since IC chip 2004 is pushed by pusher 2082 into pharmaceutical powder 2090 before being compressed by the tabletting machine main body, the positional displacement is suppressed.

Further, since IC chip 2004 is pushed into pharmaceutical powder 2090 in a downward manner in which chip main body 2006 is positioned below, chip main body 2006 is further inserted into pharmaceutical powder 2090 with respect to a surface of pharmaceutical powder 2090 to which, for example, base film 2005 comes into contact. Therefore, even when IC chip 2004 attempts to move in a horizontal direction, chip main body 2006 serves as a wedge, so that the positional displacement due to lateral movement can be suppressed assuredly.

Further, in the present embodiment, as described above, the horizontal state and centering can be maintained with a high accuracy by protrusions 2067 of positioning guide 2061. Thus, since it can be supplied to a center of pharmaceutical powder 2090 assuredly, positioning is ensured without performing an inspection after the supply on whether or not a supply to a correct position is performed. Accordingly, even in a case where an inspection apparatus is provided, it may be, for example, a simple sensor which confirms presence of a supply, and it can be applied to an apparatus for which a space cannot be reserved for installation.

FIGS. 56A to 56K shows an operation of tabletting machine main body 2076. As shown in FIG. 56A, in a lower side of die hole 2078, a lower pestle 2092 is fitted from below so as to be slidable up and down. As shown in FIG. 56I, in an upper side of die hole 2078, an upper pestle 2093 is provided movably upward and downward. As shown in FIG. 56A, firstly, in a state where lower pestle 2092 is lowered within die hole 2078, pharmaceutical powder 2094 is filled in die hole 2078 by means of pharmaceutical powder filling apparatus 2094. Next, as lower pestle 2092 is lifted, a supply by means of pharmaceutical powder filling apparatus 2094 is cut, so that a predetermined amount of pharmaceutical powder 2090 is filled in a leveled state in a space of die hole 2078 formed on an upper side of lower pestle 2092 (FIG. 56B). After that, lower pestle 2092 is lowered by a predetermined quantity, so that a surface of pharmaceutical powder 2090 is slightly lowered from an upper surface of rotating plate 2077 (FIG. 56C).

In this state, by IC chip supply apparatus 2074 described above, positioning guide 2061 in which IC chip 2004 in a downward manner is set enters die hole 2078 (FIG. 56D), pushes out IC chip 2004 by means of pusher 2082, and pushes it into pharmaceutical powder 2090 (FIG. 56E).

Next, rotating plate 2077 rotates so that a die hole at the supply positions proceeds to the next step (FIG. 56F). In a state where lower pestle 2092 is lowered within die hole 2078, pharmaceutical powder 2090 is filled and supplied into die hole 2078 by means of pharmaceutical powder filling apparatus 2094 (FIG. 56G). Next, lower pestle 2092 is lifted, and a supply by means of pharmaceutical powder filling apparatus 2094 is cut, so that a predetermined amount of pharmaceutical powder 2090 is filled in a leveled state in a space of die hole 2078 formed on an upper side of lower pestle 2092 (FIG. 56H).

Next, upper pestle 2093 moves downward, and pharmaceutical powder 2090 is compressed between upper pestle 2093 and lower pestle 2092 (FIG. 56I). Accordingly, pharmaceutical powder 2090 is solidified to manufacture IC chip-containing tablet 2095 (FIG. 56J). After that, lower pestle 2092 further moves upward, so that manufactured tablet 2095 is discharged.

Modified Example

Push-in portion 2064 is not always necessary. Without providing push-in portion 2064, in a state where a lower surface of main body 2062 is in contact with an upper surface of rotating plate 2077, IC chip 2004 may be pushed out with a pusher. In this case, pharmaceutical powder in the die hole may be filled to an upper end of the die hole to be in a leveled state.

Further, when push-in portion 2064 is provided as in the above-described embodiment, push-in portion 2064 may enter die hole 2078 to further push in the pharmaceutical powder filled in die hole 2078. Accordingly, a recess having an inner shape in conformity with an outer shape of push-in portion 2064 is formed on a surface of the pharmaceutical powder. Accordingly, since IC chip 2004 is set within the recess, the positional displacement due to the lateral movement can be suppressed assuredly.

Moreover, even in the case where push-in portion 2064 is provided, push-in portion 2064 may be set so as not to come into contact with pharmaceutical powder. For example, depending on a material of pharmaceutical powder, pharmaceutical powder may be attached to a surface of push-in portion 2064 by contact, or pharmaceutical powder may be dispersed to a periphery at the time of contact. In such a case, providing push-in portion 2064 at a position not in contact with pharmaceutical powder may avoid the problem.

Moreover, in the above-described embodiment, IC chip 2004 is pushed into pharmaceutical powder 2090. However, the present invention is not limited to this. For example, IC chip 2004 may remain on the surface of pharmaceutical powder 2090 by a dropping supply. For example, when IC chip 2004 is pushed into pharmaceutical powder 2090, the force of pushing-in may cause pharmaceutical powder 2090 to fly, so that it may affect the detection of presence of an IC chip in the subsequent step. By not pushing in the IC chip, the influence can be suppressed as soon as possible. Moreover, when the dropping supply is performed, it is favorable that the falling distance is small.

Even in the case of providing protrusions, positioning guide 2061 may be omitted at the lower end rather than forming it to the lower end. In such a case, for example, protrusions may be formed only at the main body portion, and the protrusions may be omitted entirely or partially at the portion corresponding to the push-in portion.

It should be noted that, in the above-described embodiment, positioning guide 2061 including at its inner circumferential surface protrusions 2067 is provided, and it is pushed by a pusher in a state where IC chip 2004 is set within positioning guide 2061. However, the present invention is not limited to this. For example, suction means may be used in place of the pusher, and the IC chip suctioned by suction means may be pushed into the pharmaceutical powder within the die hole to supply the same.

Furthermore, in the above-described embodiment, a lower end of positioning guide 2061 (push-in portion 2064) enters die hole 2078 by upward and downward movement. However, positioning guide 2061 and rotary table 2075 may be not moved upward and downward. By omitting the step of moving upward and downward, a cycle time is shortened, and the process can be speeded up. In this case, IC chip 2004 is supplied by dropping it into die hole 2078.

Moreover, in the above-described embodiment, the IC chip is supplied into pharmaceutical powder in a downward manner. However, it may be supplied in an upward manner.

The tablet manufacturing apparatus is (1) a tablet manufacturing apparatus, which manufactures an IC chip-containing tablet by supplying an IC chip on pharmaceutical powder filled in a die hole, further filling pharmaceutical powder onto the IC chip, and compressing these pharmaceutical powder and the IC chip from above and below, and it includes supply means which performs a supply of the IC chip by pushing in the IC chip into pharmaceutical powder in a state where the IC chip is positioned above pharmaceutical powder within a die hole before being compressed.

Since the IC chip is supplied by pushing into pharmaceutical powder before being compressed, it can be supplied to a desired position with a high accuracy, so that the positional displacement can be suppressed.

(2) The IC chip includes a convex portion on one surface, and it is favorable to supply the IC chip by pushing the convex portion into pharmaceutical powder in a downward manner with the convex portion provided on a lower side. The convex portion corresponds to chip main body 6 in the embodiment. It is not limited to attach chip main body 6 to base film 6 as in the embodiment. For example, it can be applied to various forms such as having a convex portion on a surface of the chip main body of the embodiment. According to the present invention, the convex portion is further inserted into pharmaceutical powder. Accordingly, for example, the convex portion serves as a wedge even when the IC chip attempts to move in the horizontal direction, and the positional displacement due to the lateral movement can be suppressed assuredly.

(3) The IC chip is set in the accommodation portion provided on a carrier tape in an upward manner with the convex portion on an upper side, and is accommodated in an accommodation tape having an opening side of the accommodation portion covered with a top tape, and it may be configured such that the IC chip in an upward manner is taken out from the accommodation portion, and the taken out IC chip may be reversed upside down to be in a downward manner, and may be supplied by supply means. Accordingly, even with the one supplied in an upward manner, it can be converted into a downward manner and supplied to the pharmaceutical powder.

(4) The supply means may include a position guide holding an IC chip within a through-hole penetrating up and down, and pushing means which is arranged on an upper side of the positioning guide and pushes out the IC chip downward.

Since the IC chip is pushed in and supplied to pharmaceutical powder before being compressed, it can be supplied to a desired position with a high accuracy, so that the positional displacement can be suppressed.

An manner position converting apparatus is (1) an manner converting apparatus which changes an manner of an electronic part by passing an electronic part suctioned and held by a first suction and hold member to a second suction and hold member suctioning the same, and it is configured to perform the passing in a state where a suction portion of the first suction and hold member and a suction portion of the second suction and hold member are inserted into through-holes of a guide member having the through-holes at both ends. The electronic part corresponds to the IC chip of the embodiment. In the embodiment, the IC chip is provided in a tablet. However, the present invention can be applied not only to this but also to various electronic parts. Moreover, the through-holes of the present invention are opened at both ends, and the first suction and hold member and second suction and hold member enter into the through-holes respectively through the openings on both ends. However, for example, a part of the side surface of the through-hole may be opened by a slit or other structure. It should be noted that the manner converting apparatus may be used for any application other than the tablet manufacturing apparatus.

Since the passing of electronic parts between the suction and hold members is performed within the guide members (through-holes), the passing can be performed assuredly without any influence from outside or peripheral atmosphere.

(2) The cylindrical guide is may be configured so that inner shape dimensions of the through-hole is formed to be wide at both ends and narrow at an intermediate position, and passing is performed at the intermediate position. In such a manner, since the both ends are wide, both suction and hold members can smoothly enter at the leading end into the cylindrical guide, and the passing is performed at the narrow space, it is preferable. The narrow space at the intermediate position may be formed to have an inner shape dimension shape corresponding to the outer dimension shape of the electronic part. The corresponding inner shape dimensions shape may be set equal to or larger than the outer dimension shape.

(3) The electronic part is accommodated in an accommodation tape, and the first suction and hold member may be configured to suction and hold the electronic part within the accommodation tape, rotate it by a set angle, and insert the electronic part into a guide member. (4) The set angle may be 180 degrees. It is favorable since a reverse apparatus for reversing an electronic part upside down can be configured in a simple manner.

(5) It is favorable that the guide member is constituted of a fixed cylindrical guide. This cylindrical guide is achieved in the embodiment. It is favorable since it can be achieved with a simple configuration. (6) The guide member includes a plurality of moving guide members and a drive mechanism for allowing the moving guide members to come close to and separate from each other, and it is favorable to form through-holes by allowing the plurality of moving guide members to come close to each other. In this manner, by separating the moving guide members, a space wider than the through-hole is reserved, and for example, even in a case where a positional displacement occurs at the time of suctioning and holding an electronic part by means of the first suction and hold member, when the moving guide members are moved to come close to each other in the state where the first suction and hold member is positioned at the passing position of the electronic part to the second suction and hold member, a leading end of the moving guide members come into contact with a side surface of the electronic part to move to a center and position the same, so that it is favorable.

Accordingly, passing of the electronic part can be performed assuredly. To solve the problem described above, an IC chip supply apparatus of the present invention is (1) an IC supply apparatus in a tablet manufacturing apparatus for manufacturing IC chip-containing tablets by supplying an IC chip onto pharmaceutical powder filled in a die hole, further filling pharmaceutical powder onto the IC chip, and compressing these pharmaceutical powder and the IC chip from above and below, and it includes a positioning guide holding the IC chip within a through-hole penetrating up and down, and pushing-out means arranged on an upper side of the positioning guide and pushing out the IC chip downward, and a plurality of protrusions protruding toward a center is included inside of the through-hole, and the IC chip is held by the protrusions. The pushing-out means corresponds to pusher 2082 in the embodiment.

According to the present invention, by the protrusions of the positioning guide, the IC chip is set and held with a high accuracy at a desired position in a cross section within the through-hole. Thus, the IC chip can be supplied at a desired position within a die hole corresponding to the set position. Accordingly, for example, it can be assuredly supplied to a center of pharmaceutical powder, positioning can be secured without performing an inspection on whether or not a supply is performed to a correct position after the supplying operation. Accordingly, for example, even in the case where the inspection apparatus is provided, it may be a simple sensor which confirms presence of a supply, and an apparatus which cannot reserve a space for installation can be used.

(2) The plurality of protrusion may be convex threads extending along an axial direction of the through-hole. (3) The convex threads may be formed to a lower end of the through-hole. In such a manner, the positioning can be performed until immediately before pushing out from a lower end of the positioning guide, thus it is preferable.

(4) The positioning guide may be provided with a push-in portion protruding downward at a lower surface, and the push-in portion may enter the die hole. In such a manner, since the push-in portion enters the die hole, the IC chip can be supplied to a desired position within the die hole.

(5) The positioning guide may be provided at a rotation member, and may have a function of holding with the protrusions the IC chip by inserting the IC chip from above with respect to the positioning guide located at the receiving position, and the positioning guide holding the IC chip may rotate with the rotation of the rotation member and positioned on an upper side of the die hole of the tabletting machine, and the IC chip held by the pushing-out means may allow an IC chip to be supplied into a die hole. The passing of the IC chip from an apparatus on an upstream side, and a supply of an IC chip to a tabletting machine can be performed simultaneously, so that the productivity is improved.

(6) A tablet manufacturing apparatus of the present invention may include means for filling pharmaceutical powder into a die hole, the IC chip supply apparatus according to any one of (1) to (5) supplying an IC chip onto the pharmaceutical powder, means for filling pharmaceutical powder from above the supplied IC chip, and means for manufacturing an IC chip-containing tablet by compressing these pharmaceutical powder and the IC chip from above and below.

By the plurality of protrusions provided at the positioning guide, the IC chip is held at a desired position, and supplied into the die hole in that state, so that it can be supplied to a desired position with a high accuracy, and the positional displacement can be suppressed.

A manufacturing apparatus for medical tablets is a manufacturing apparatus for medical tablets, which manufactures an IC chip member-containing tablet 95, 1095, 2095 by supplying an IC chip 4, 1004, 2004 as an IC chip member equipped with an IC on pharmaceutical powder filled in a die hole, thereafter filling pharmaceutical powder onto IC chip 4, 1004, 2004, and compressing these pharmaceutical powder and IC chip 4, 1004, 2004 from above and below, and IC chip 4, 1004, 2004 has a base film 5, 1005, 2005 as a base plane, and a chip main body 6, 1006, 2006 as a convex portion protruding more on one side than the other side with respect to base film 5, 1005, 2005, and the manufacturing apparatus for medical tablets includes a supply apparatus 3, 1003, 2003 which holds IC chip 4, 1004, 2004 in a downward manner with chip main body 6, 1006, 2006 facing downward, and supplies IC chip 4, 1004, 2004 on the pharmaceutical powder.

IC chip 4, 1004, 2004 is set in an accommodation recess 8a, 1008a, 2008a as an accommodation portion provided in a carrier tape 8, 1008, 2008 in an upward manner with chip main body 6, 1006, 2006 facing upward, and is accommodated in an accommodation tape 7, 1007, 2007 in which an opening side of accommodation recess 8a, 1008a, 2008a is covered with a top tape 9, 1009, 2009, and IC chip 4, 1004, 2004 in an upward manner is taken out of accommodation recess 8a, 1008a, 2008a, and taken-out IC chip 4, 1004, 2004 is reversed upside down and changed to the downward manner, and there after supply apparatus 3, 1003, 2003 supplies IC chip 4, 1004, 2004.

A first suction and hold member 22, 1022, 2022 which suctions and holds IC chip 4, 1004, 2004, a second suction and hold member 23, 1023, 2023 which suctions IC chip 4, 1004, 2004 held by first suction and hold member 22, 1022, 2022, from a side opposite to first suction and hold member 22, 1022, 2022, and a cylindrical guide 40, 1040, 2040 as a guide member provided with a through-hole 41, 1041, 2041 into which IC chip 4, 1004, 2004 is inserted, a suction portion of first suction and hold member 22, 1022, 2022 is inserted from one side of through-hole 41, 1041, 2041, and a suction portion of second suction and hold member 23, 1023, 2023 is inserted from the other side of through-hole 41, 1041, 2041, and IC chip 4, 1004, 2004 is passed from first suction and hold member 22, 1022, 2022 to second suction and hold member 23, 1023, 2023 within through-hole 41, 1041, 2041.

Inner shape dimensions of through-hole 41, 1041, 2041 are formed to be wide at end portions in inlet region 41a, 1041a, 2041a and outlet region 41c, 1041c, 2041c, and to be narrow at a center region 41b, 1041b, 2014b as an intermediate position (intermediate region), and IC chip 4, 1004, 2004 is passed at center region 41b, 1041b, 2041b.

IC chip 4, 1004, 2004 is accommodated in a carrier tape 8, 1008, 2008, and first suction and hold member 22, 1022, 2022 suctions and holds IC chip 4, 1004, 2004 within carrier tape 8, 1008, 2008, rotates by a set angle, and inserts IC chip 4, 1004, 2004 into through-hole 41, 1041, 2041 in cylindrical guide 40, 1040, 2040.

Guide member 1098 includes a plurality of moving guide members 1096, and a cylinder 1097 as a drive mechanism which causes the plurality of moving guide members 1096 to come close to or separate from each other, and the plurality of moving guide members 1096 come close to form the through-hole.

A manufacturing apparatus for medical tablets is a manufacturing apparatus for medical tablets, which manufactures an IC chip 4, 1004, 2004-containing tablet 95, 1095, 2095 by supplying an IC chip 4, 1004, 2004 on pharmaceutical powder filled in a die hole, further filling pharmaceutical powder onto IC chip 4, 1004, 2004, and compressing these pharmaceutical powder and IC chip 4, 1004, 2004 from above and below, and it includes a positioning guide 61, 1061, 2061 which has a through-hole 66, 1066, 2066 penetrating up and down, and holds IC chip 4, 1004, 2004 within through-hole 66, 1066, 2066, and a pusher 82, 1082, 2082 as a push-out portion arranged above positioning guide 61, 1061, 2061 for pushing out IC chip 4, 1004, 2004 downward, and a plurality of protrusions 67, 1067, 2067 protruding toward a center are provided on an inside of through-hole 66, 1066, 2066, and IC chip 4, 1004, 2004 is held by protrusions 67, 1067, 2067.

The plurality of protrusions 67, 1067, 2067 are convex threads extending along an axial direction of the through-hole. The convex threads are formed to a lower end of through-hole 66, 1066, 2066.

Positioning guide 61, 1061, 2061 is provided to a rotary table 75, 1075, 2075 as a rotation member, and IC chip 4, 1004, 2004 is pushed from above into positioning guide 61, 1061, 2061 at a receiving position and IC chip 4, 1004, 2004 is held by protrusions 67, 1067, 2067, and, in a state where positioning guide 61, 1061, 2061 holding IC chip 4, 1004, 2004 rotates and moves together with rotation of rotary table 75, 1075, 2075 and is located above the die hole of a tabletting machine, hold IC chip 4, 1004, 2004 is supplied into the die by pusher 82, 1082, 2082.

A manufacturing method for medical tablets includes the steps of holding an IC chip 4, 1004, 2004, which has a base film 5, 1005, 2005 and a chip main body 6, 1006, 2006 protruding more on one side than on the other side with respect to base film 5, 1005, 2005, in a downward manner with the convex portion facing downward, and supplying the IC chip in the downward manner on pharmaceutical powder, and manufacturing a tablet 95, 1095, 2095 containing IC chip 4, 1004, 2004 by filling pharmaceutical powder onto IC chip 4, 1004, 2004, and compressing these pharmaceutical powder and IC chip 4, 1004, 2004 from above and below.

A manufacturing method for medical tablet includes the steps of a first suction and hold member 22, 1022, 2022 suctioning and holding an IC chip 4, 1004, 2004, inserting a suction portion of first suction and hold member 22, 1022, 2022 from one side of a through-hole 41, 1041, 2041, inserting a suction portion of second suction and hold member 23, 1023, 2023 from the other side of through-hole 41, 1041, 2041, passing IC chip 4, 1004, 2004 from first suction and hold member 22, 1022, 2022 to second suction and hold member 23, 1023, 2023 within through-hole 41, 1041, 2041 to hold IC chip 4, 1004, 2004 in a downward manner.

A manufacturing method for medical tablets includes the steps of holding an IC chip 4, 1004, 2004 with a plurality of protrusions 67, 1067, 2067 protruding toward a center provided on an inside of a through-hole 66, 1066, 2066 in a positioning guide 61, 1061, 2061, supplying IC chip 4, 1004, 2004 held within through-hole 66, 1066, 2066 on pharmaceutical powder filled in a die hole, and manufacturing a tablet 95, 1095, 2095 containing IC chip 4, 1004, 2004 by filling pharmaceutical powder onto IC chip 4, 1004, 2004, and compressing these pharmaceutical powder and IC chip 4, 1004, 2004 from above and below.

The manufacturing method further includes the step of pushing IC chip 4, 1004, 2004 from above into positioning guide 61, 1061, 2061 located at a receiving position, and the step of supplying IC chip 4, 1004, 2004 includes supplying IC chip 4, 1004, 2004 into the die hole by a push-out portion, in a state where positioning guide 61, 1061, 2061 holding IC chip 4, 1004, 2004 rotates and moves together with rotation of rotary table 75, 1075, 2075 and is located above the die hole of a tabletting machine.

REFERENCE SIGNS LIST 2, 1002, 2002 tabletting machine; 3, 1003, 2003 supply apparatus; 4, 1004, 2004 IC chip; 5, 1005, 2005 base film; 6, 1006, 2006 chip main body; 13, 1013, 2013 accommodation tape opening portion; 20, 1020, 2020 IC chip take-out apparatus; 21, 1021, 2021 conveying apparatus; 22, 1022, 2022 first suction and hold member; 23, 1023, 2023 second suction and hold member; 40, 1040, 2040 cylindrical guide; 61, 1061, 2061 positioning guide; 1096 moving guide member; 1098 guide member; 2074 IC chip supply apparatus.

The invention claimed is:

1. An apparatus, comprising:
an integrated circuit (IC) chip member having a base plane, and a convex portion protruding more on one side than the other side with respect to the base plane;
a supply portion configured to supply the IC chip member equipped with an IC on first pharmaceutical powder in a die hole, said supply portion configured to hold the IC chip member in a downward manner such that the convex portion faces downward when said supply portion supplies the IC chip member on the first pharmaceutical powder;
a pharmaceutical powder filling apparatus configured to fill second pharmaceutical powder onto the IC chip member; and
a set of pestles configured to compress the first pharmaceutical powder, the second pharmaceutical powder and the IC chip member from above and below.

2. The apparatus according to claim 1, further comprising:
a carrier tape having an accommodation portion configured to hold the IC chip member in an upward manner where the convex portion faces upward, an opening side of said accommodation portion is covered with a top tape,
the IC chip member in said upward manner is configured to be removed from said accommodation portion, reversed upside down and changed to said downward manner, prior to said supply portion supplying the IC chip member.

3. The apparatus according to claim 1, further comprising:
a first suction member configured to suction and hold the IC chip member;
a second suction member configured to suction the IC chip member held by said first suction member, from a side opposite to said first suction member; and
a guide member defining a through-hole into which the IC chip member is configured to be inserted, wherein
a suction portion of said first suction member is configured to be inserted from one side of said through-hole, and a suction portion of said second suction member is configured to be inserted from the other side of said through-hole, and
said first suction member is configured to pass the IC chip member to said second suction member within said through-hole.

4. The apparatus according to claim 3, wherein
inner shape dimensions of said through-hole are wider at end portions on said one side and the other side than at an intermediate position, and
said first suction member is configured to pass the IC chip member to said second suction member at said intermediate position.

5. The apparatus according to claim 3, wherein
said first suction member is configured to suction and remove the IC chip member from within a carrier tape, rotate the IC chip member by a set angle, and insert the IC chip member into said through-hole in said guide member.

6. The apparatus according to claim 3, wherein
said guide member includes a plurality of moving guide members, and a drive mechanism configured to cause the plurality of moving guide members to come close to or separate from each other, and
the plurality of moving guide members come close to each other to form said through-hole.

7. The apparatus according to claim 1, wherein the supply portion includes:
a positioning guide defining a through-hole penetrating up and down, the positioning guide configured to hold the IC chip member within the through-hole;
a plurality of protrusions on an inside of said through-hole and protruding toward a center of said through-hole, the plurality of protrusions configured to hold said IC chip member in the downward manner where the convex portion faces downward; and
a push-out portion arranged above the positioning guide configured to push said IC chip member out of the positioning guide downward.

8. The apparatus according to claim 7, wherein said plurality of protrusions are convex threads extending along an axial direction of said through-hole.

9. The apparatus according to claim 8, wherein said convex threads are formed at a lower end portion of said through-hole.

10. The apparatus according to claim 8, wherein
said positioning guide is configured to be provided to a rotation member, and
the IC chip member is configured to be pushed from above and into said positioning guide located at a receiving position such that the IC chip member is held by said plurality of protrusions,
the push-out portion configured to supply the IC chip member into said die hole after said positioning guide holding the IC chip member rotates and moves together with rotation of said rotation member and is located above said die hole of a tabletting machine.

11. An apparatus, comprising:
an integrated circuit (IC) chip member (1) equipped with an IC and (2) having a base plane and a convex portion protruding more on one side than the other side with respect to the base plane;
a supply portion configured to hold the IC chip member in a downward manner where the convex portion faces downward, the supply portion configured to supply the IC chip member on first pharmaceutical powder such that the convex portion contacts the first pharmaceutical powder;
a pharmaceutical powder filling apparatus configured to fill second pharmaceutical powder onto the IC chip member; and
a set of pestles configured to compress the first pharmaceutical powder, the second pharmaceutical powder and the IC chip member from above and below to manufacture an IC chip member-containing tablet.

12. The apparatus according to claim 11, further comprising:
a carrier tape having an accommodation portion configured to hold the IC chip member in an upward manner where the convex portion faces upward, an opening side of said accommodation portion is covered with a top tape, the IC chip member in said upward manner is configured to be removed from said accommodation portion, reversed upside down and changed to said downward manner, prior to said supply portion supplying the IC chip member.

13. An apparatus, comprising:
a first suction member configured to suction and hold an integrated circuit (IC) chip member (1) equipped with an IC and (2) having a base plane and a convex portion protruding more on one side than the other side with respect to the base plane;
a second suction member configured to suction the IC chip member held by said first suction member, from a side opposite to said first suction member;
a guide member defining a through-hole into which the IC chip member is configured to be inserted,
a suction portion of said first suction member is configured to be inserted from one side of said through-hole, and a suction portion of said second suction member is configured to be inserted from the other side of said through-hole, and
said first suction member is configured to pass the IC chip member to said second suction member within said through-hole; and
a supply portion configured to hold the IC chip member in a downward manner where the convex portion faces downward, and to supply the IC chip member on first pharmaceutical powder filled in a die hole such that second pharmaceutical powder can be filled onto the IC chip member and the first pharmaceutical powder, the second pharmaceutical powder and the IC chip member can be compressed from above and below to manufacture an IC chip member-containing tablet.

14. The apparatus according to claim 13, wherein
inner shape dimensions of said through-hole are wider at end portions on said one side and the other side than at an intermediate position, and
said first suction member is configured to pass the IC chip member to said second suction member at said intermediate position.

15. The apparatus according to claim 13, wherein
said first suction member is configured to suction and remove the IC chip member from within a carrier tape, rotate the IC chip member by a set angle, and insert the IC chip member into said through-hole in said guide member.

16. The apparatus according to claim 13, wherein
said guide member includes a plurality of moving guide members, a drive mechanism is configured to cause the plurality of moving guide members to come close to or separate from each other,
the plurality of moving guide members come close to each other to form said through-hole.

17. An apparatus, comprising:
a positioning guide defining a through-hole penetrating up and down, the positioning guide configured to hold within the through-hole an integrated circuit (IC) chip member (1) equipped with an IC and (2) having a base plane and a convex portion protruding more on one side than the other side with respect to the base plane;
a plurality of protrusions on an inside of said through-hole and protruding toward a center of said through-hole, the plurality of protrusions configured to hold said IC chip member in a downward manner where the convex portion faces downward; and
a push-out portion arranged above the positioning guide configured to push said IC chip member out of the positioning guide downward to supply the IC chip member on first pharmaceutical powder filled in a die hole such that second pharmaceutical powder can be filled onto the IC chip member and the first pharmaceutical powder, the second pharmaceutical powder and the IC chip member can be compressed from above and below to manufacture an IC chip member-containing tablet.

18. The apparatus according to claim 17, wherein said plurality of protrusions are convex threads extending along an axial direction of said through-hole.

19. The apparatus according to claim 18, wherein said convex threads are formed at a lower end portion of said through-hole.

20. The apparatus according to claim 18, wherein
said positioning guide is configured to be provided to a rotation member, said positioning guide is configured to receive the IC chip member in response to the IC chip member being pushed from above and into said positioning guide located at a receiving position such that the IC chip member is held by said plurality of protrusions,
the push-out portion configured to supply the IC chip member into said die hole after said positioning guide holding the IC chip member rotates and moves together with rotation of said rotation member and is located above said die hole of a tabletting machine.

* * * * *